(12) United States Patent
Abdou

(10) Patent No.: US 10,092,330 B2
(45) Date of Patent: Oct. 9, 2018

(54) SPINOUS PROCESS FIXATION DEVICES AND METHODS OF USE

(71) Applicant: Samy Abdou, San Diego, CA (US)

(72) Inventor: Samy Abdou, San Diego, CA (US)

(*) Notice: Subject to any disclaimer, the term of this patent is extended or adjusted under 35 U.S.C. 154(b) by 195 days.

(21) Appl. No.: 14/981,451

(22) Filed: Dec. 28, 2015

(65) Prior Publication Data
US 2016/0128740 A1 May 12, 2016

Related U.S. Application Data

(63) Continuation of application No. 13/774,905, filed on Feb. 22, 2013, now abandoned.

(60) Provisional application No. 61/634,022, filed on Feb. 22, 2012.

(51) Int. Cl.
A61B 17/70 (2006.01)

(52) U.S. Cl.
CPC ...... *A61B 17/7067* (2013.01); *A61B 17/7065* (2013.01)

(58) Field of Classification Search
CPC ............. A61B 17/7062; A61B 17/7068
USPC ........... 606/246, 248, 249; 623/17.11–17.16
See application file for complete search history.

(56) References Cited

U.S. PATENT DOCUMENTS

| | | | |
|---|---|---|---|
| 7,955,392 B2 | 6/2011 | Dewey et al. | |
| 8,382,801 B2* | 2/2013 | Lamborne | A61B 17/7068 606/246 |
| 8,795,335 B1 | 8/2014 | Abdou et al. | |
| 2007/0173831 A1 | 7/2007 | Abdou | |
| 2010/0234889 A1 | 9/2010 | Hess | |
| 2012/0226313 A1* | 9/2012 | Dace | A61B 17/7068 606/248 |

OTHER PUBLICATIONS

Denis, F., "The Three Column Spine and its Significance in the Classification of Acute Thoracolumbar Spinal Injuries," Spine (Phila Pa 1976), 1983, vol. 8 (8), pp. 817-831.
Ozgur, B.M., et al., "Extreme Lateral Interbody Fusion (XLIF): A Novel Surgical Technique for Anterior Lumbar Interbody Fusion," Spine Journal, 2006, vol. 6 (4), pp. 435-443.

* cited by examiner

*Primary Examiner* — Ellen C Hammond
*Assistant Examiner* — Christina Negrellirodrigue
(74) *Attorney, Agent, or Firm* — Gazdzinski & Associates, PC

(57) ABSTRACT

Orthopedic implant and methods of implantation for fixing adjacent bones. In one embodiment, the implant includes a locking mechanism that is adapted to be advanced by a locking instrument, wherein advancement of the locking mechanism in a first direction produces rotation of a first rigid abutment surface of the implant from a first orientation to a second orientation, and continued advancement of the locking mechanism produces advancement of the first rigid abutment surface towards a second rigid abutment surface of the implant. The continued advancement may also place a compressive load onto the implant sufficient to immobilize the implant relative to a first bony surface and a second bony surface.

34 Claims, 56 Drawing Sheets

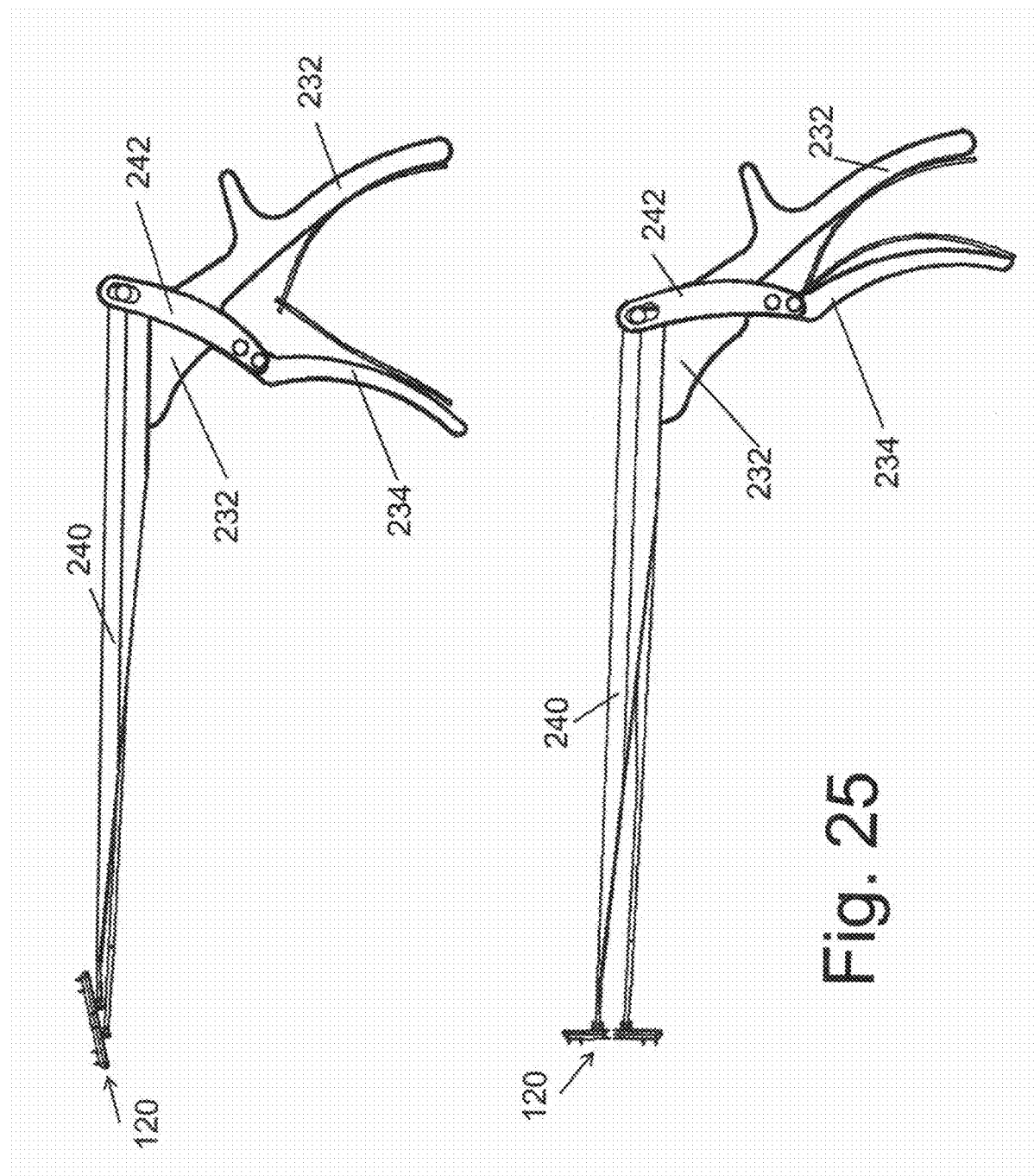

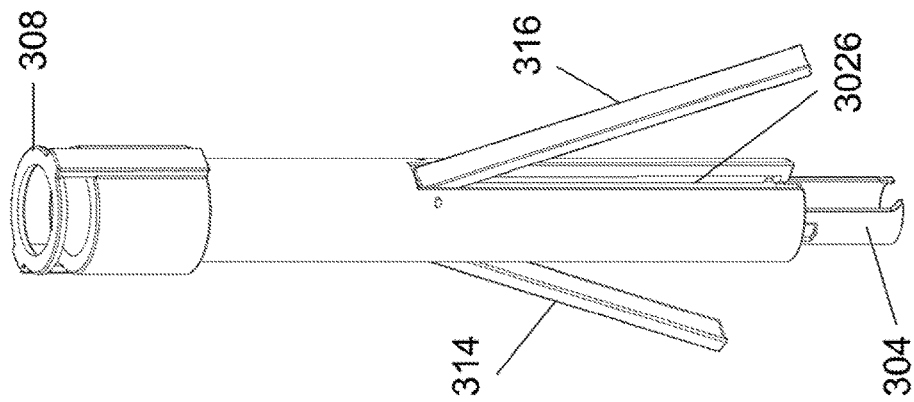
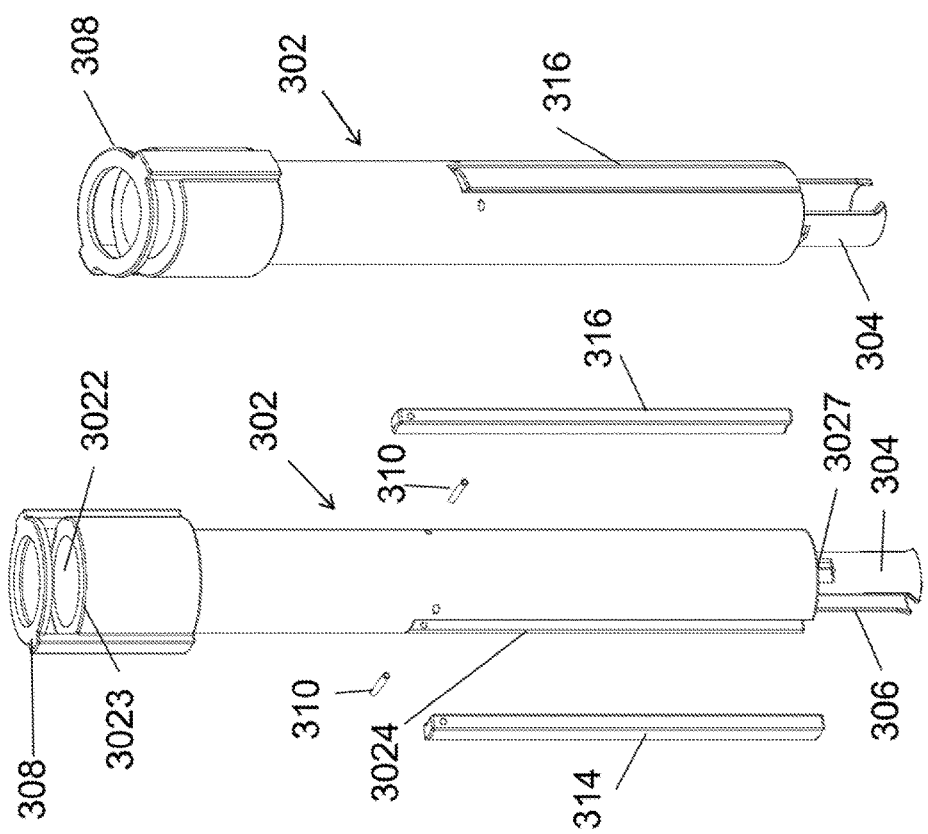
Fig. 26A  Fig. 26B  Fig. 26C

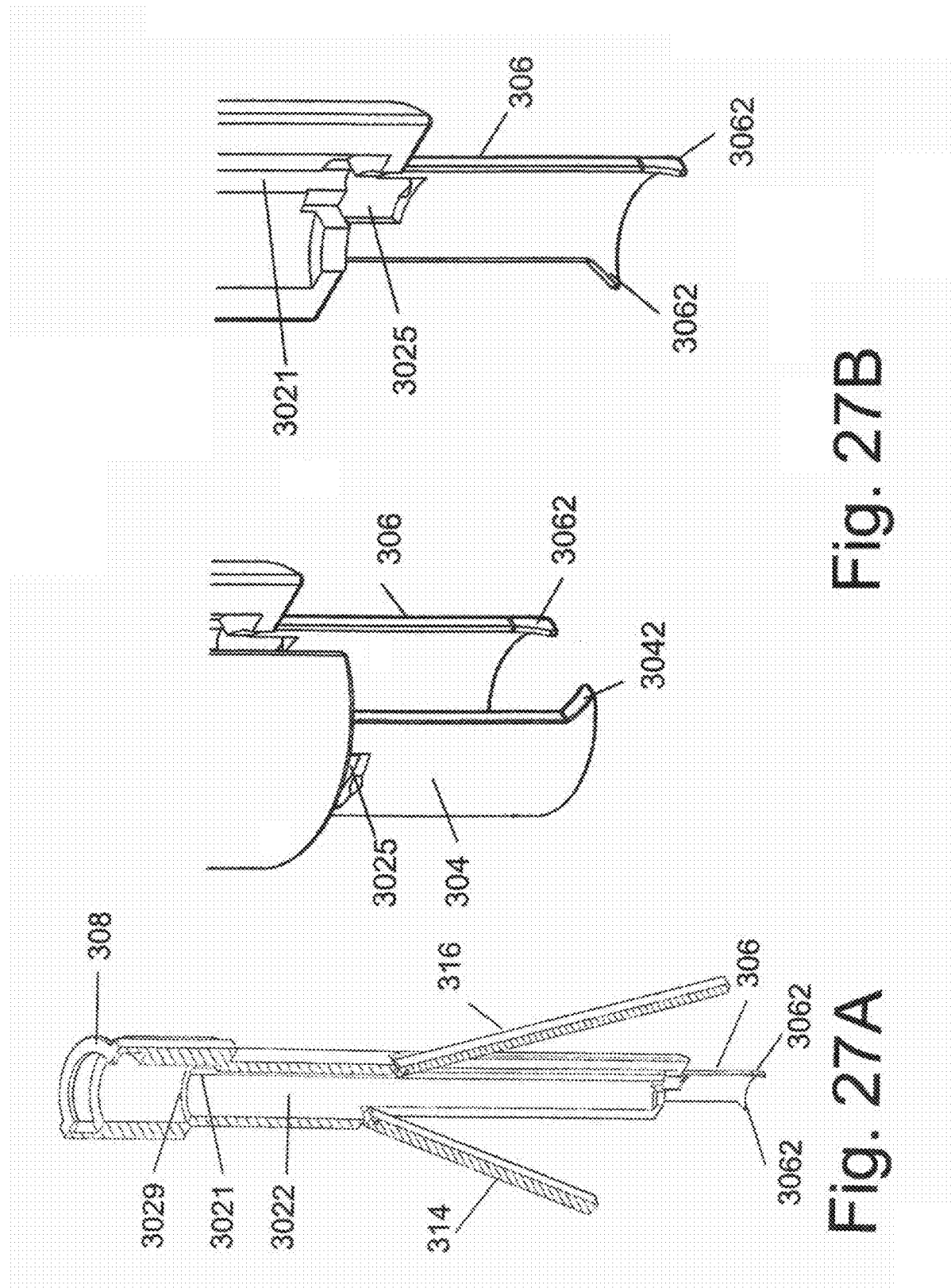

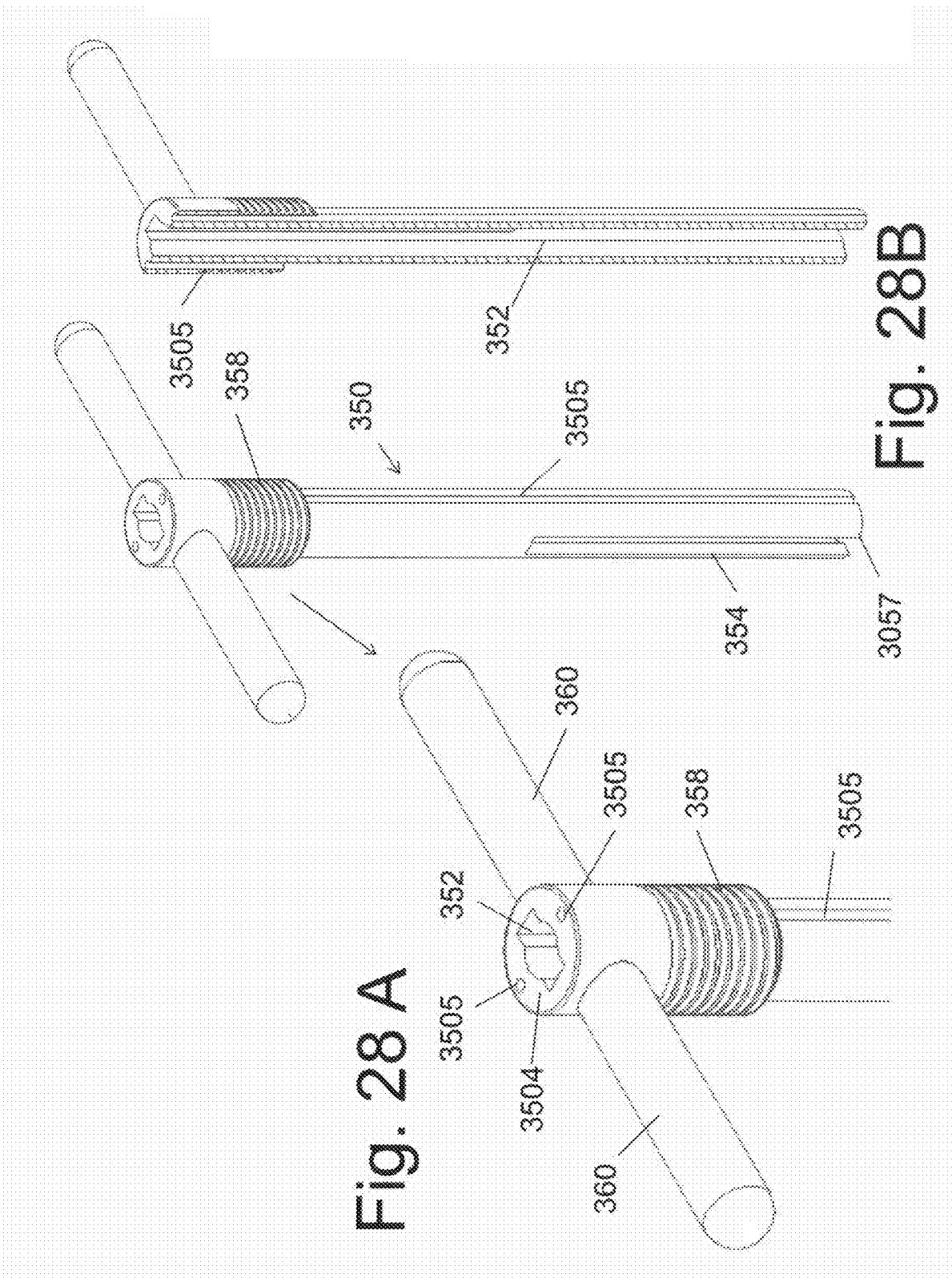

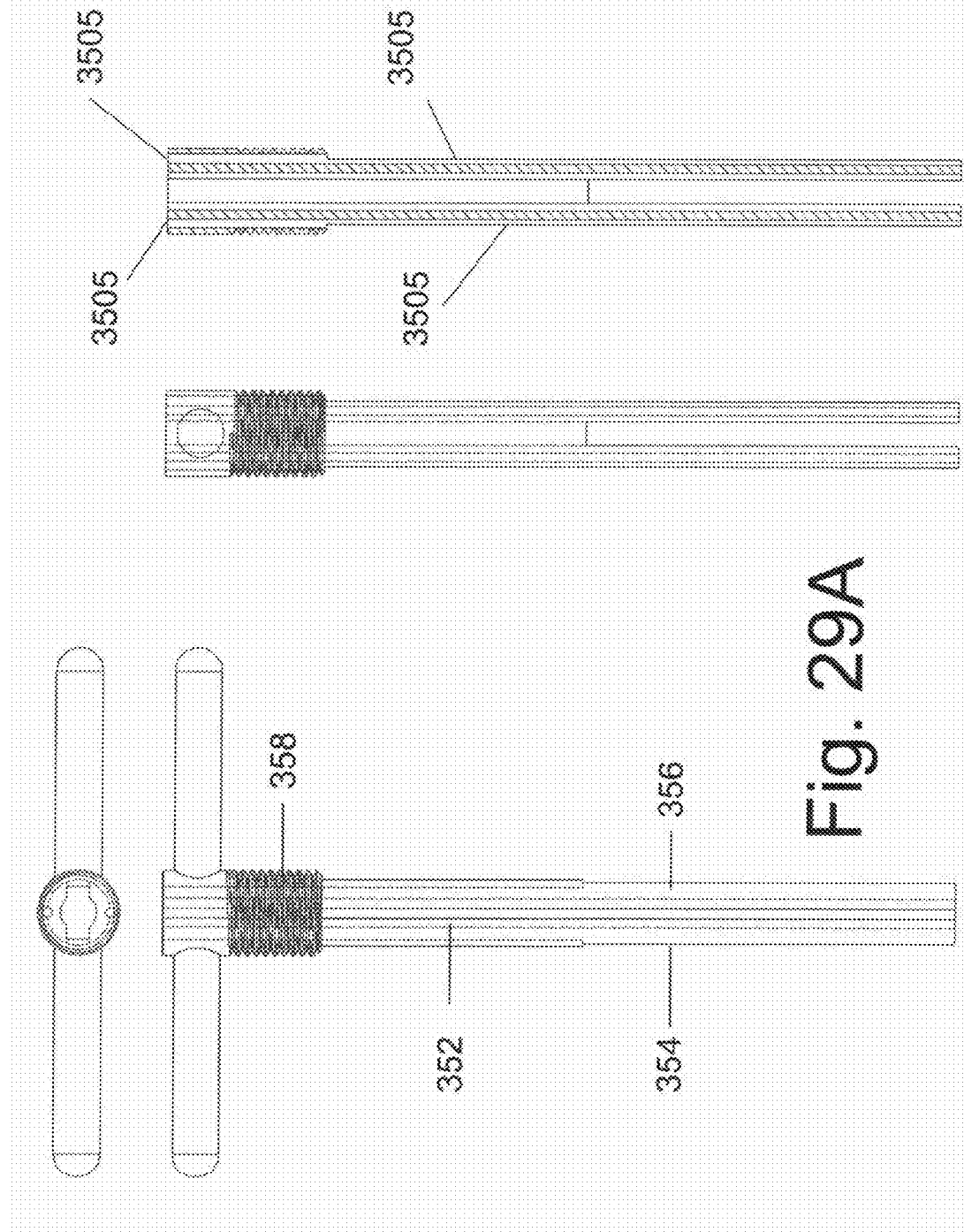

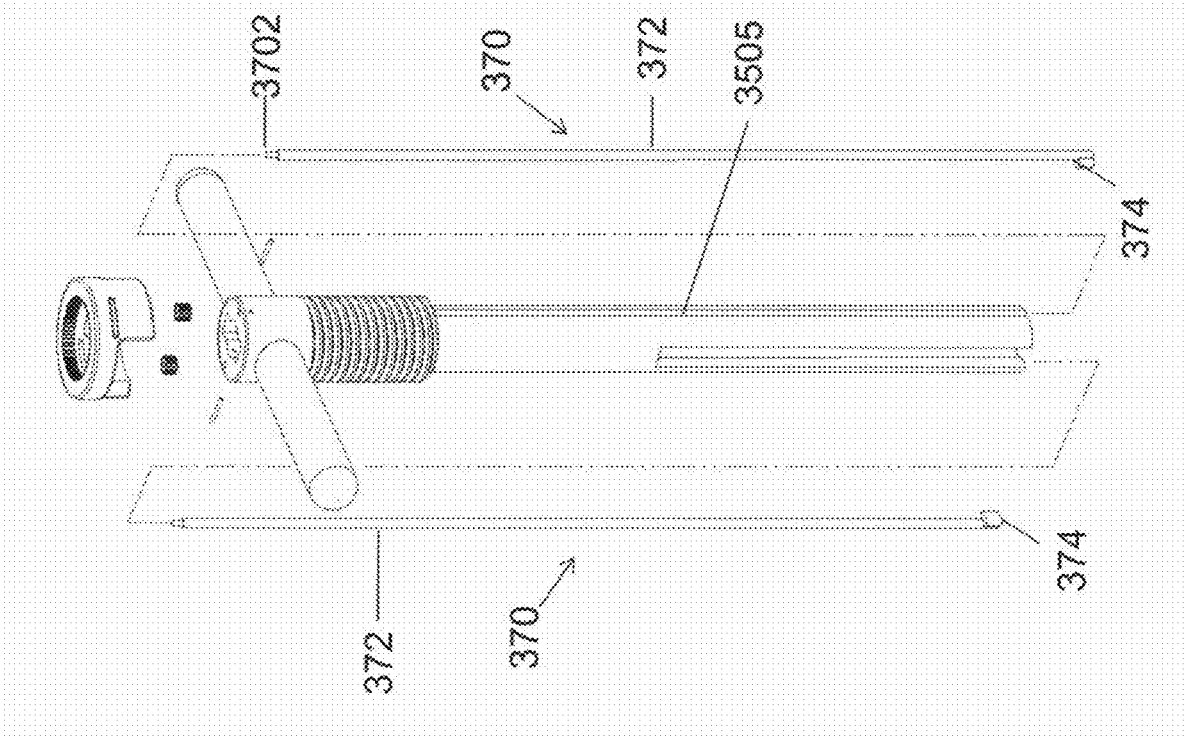

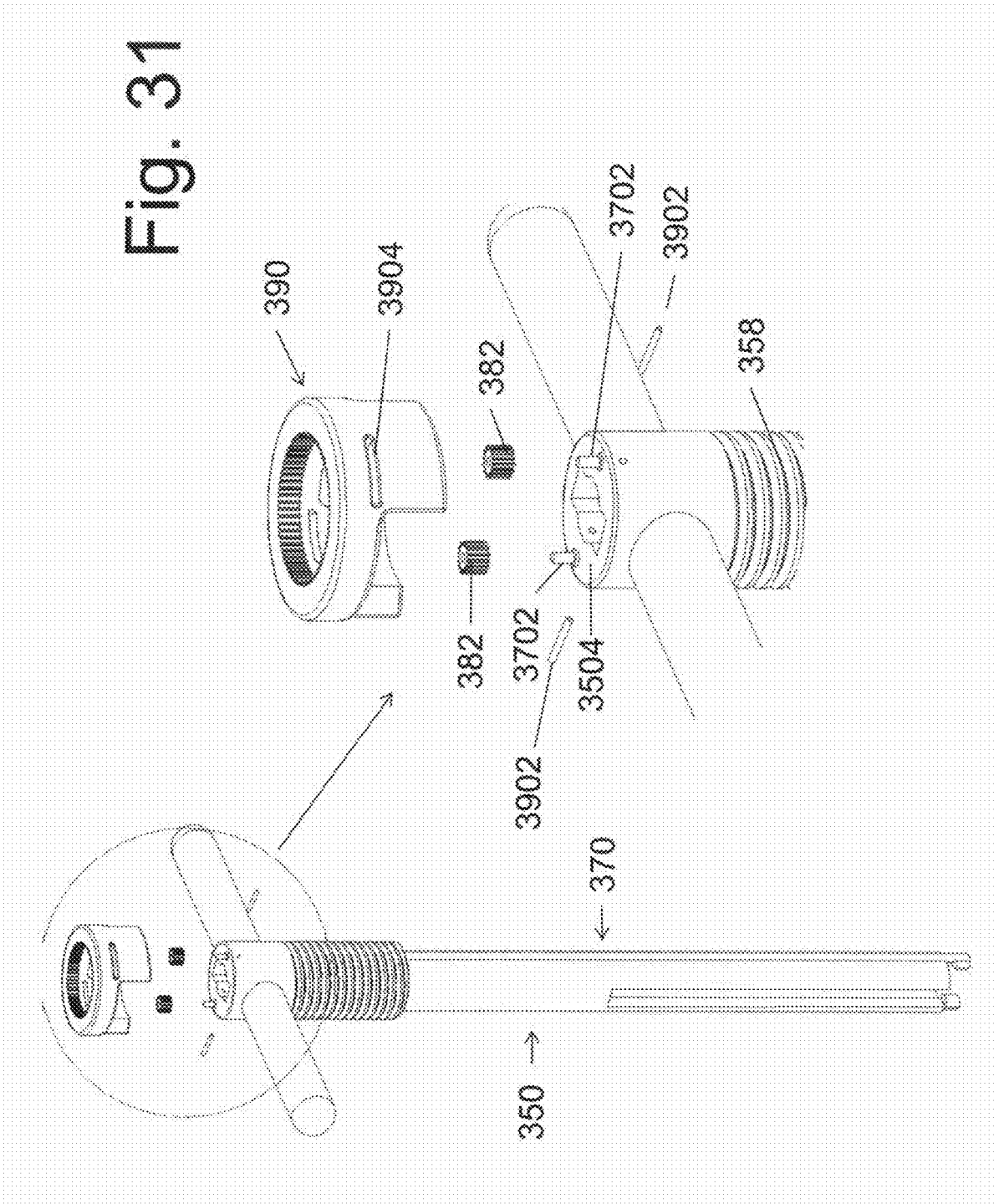

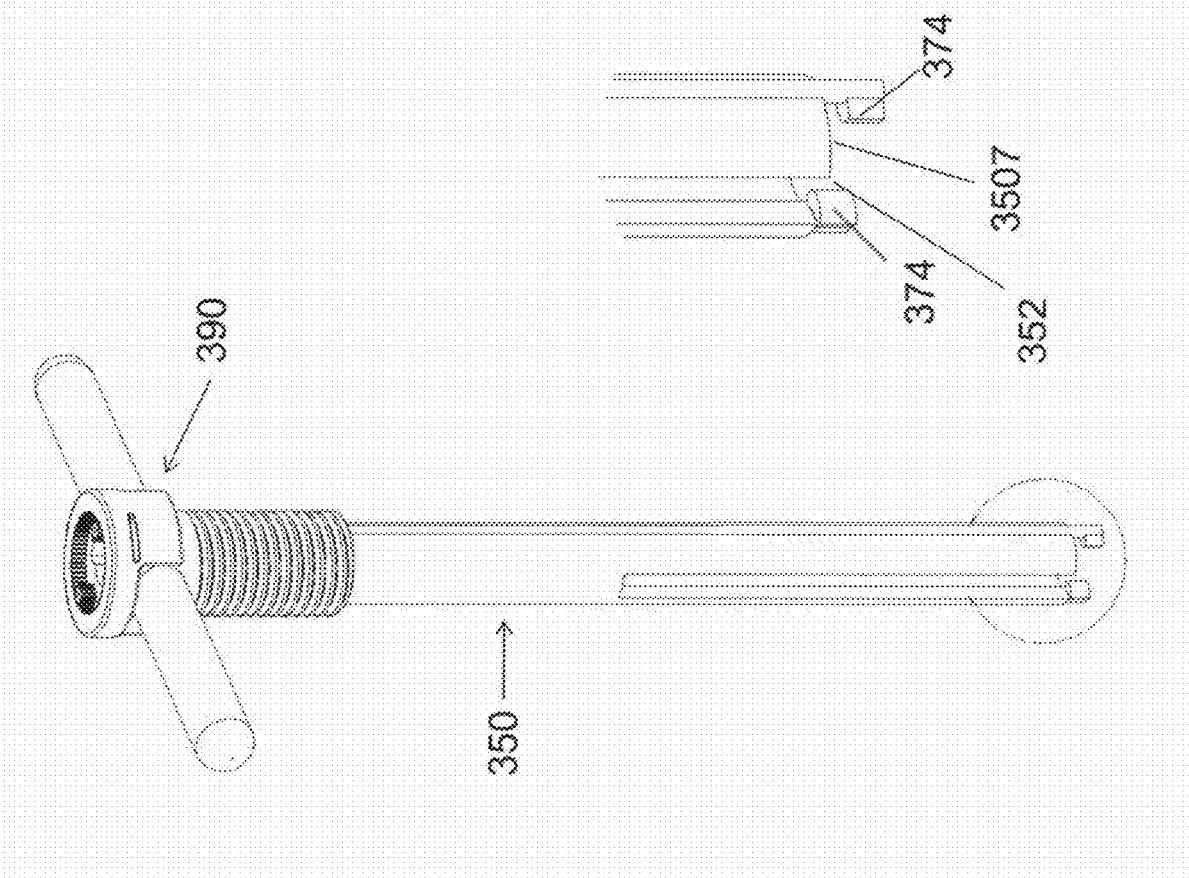

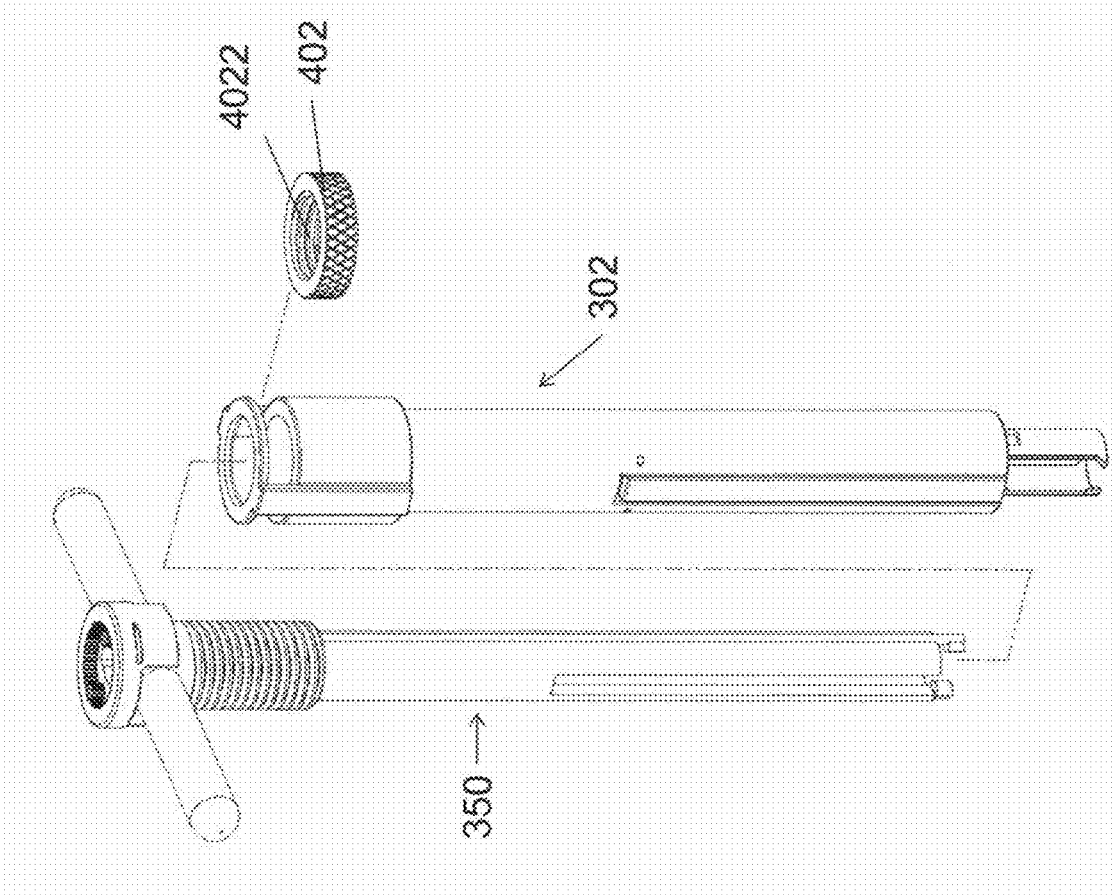

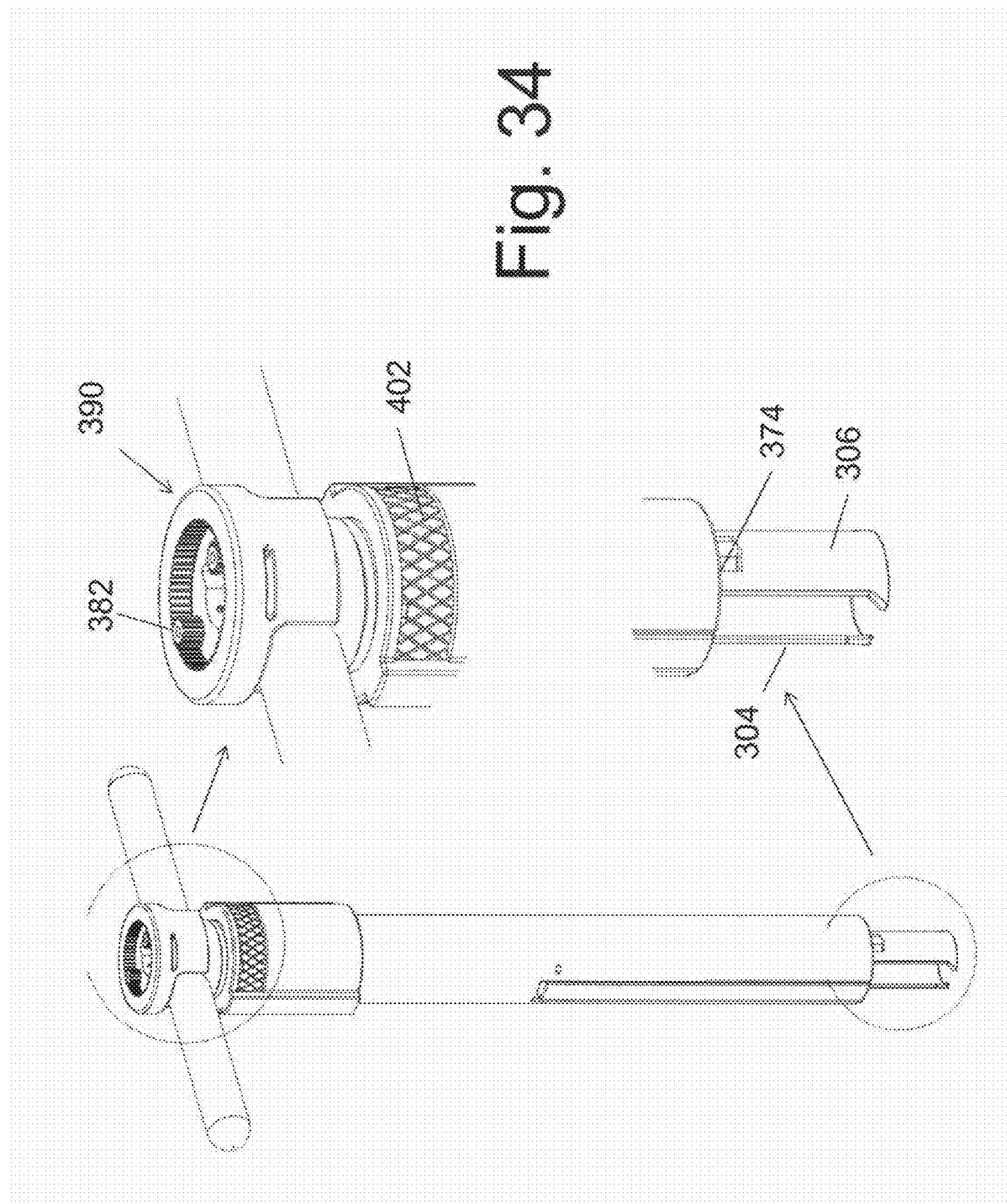

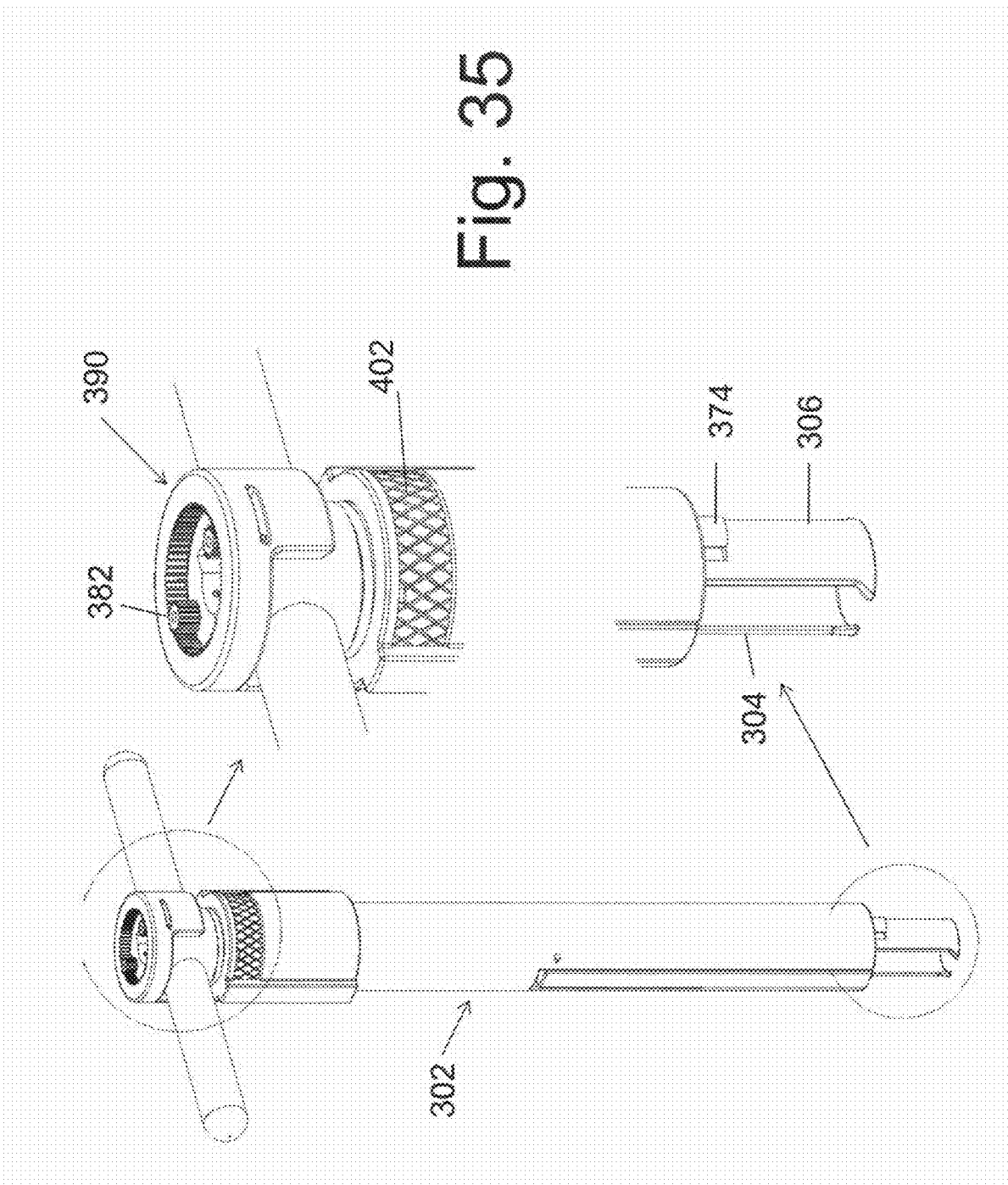

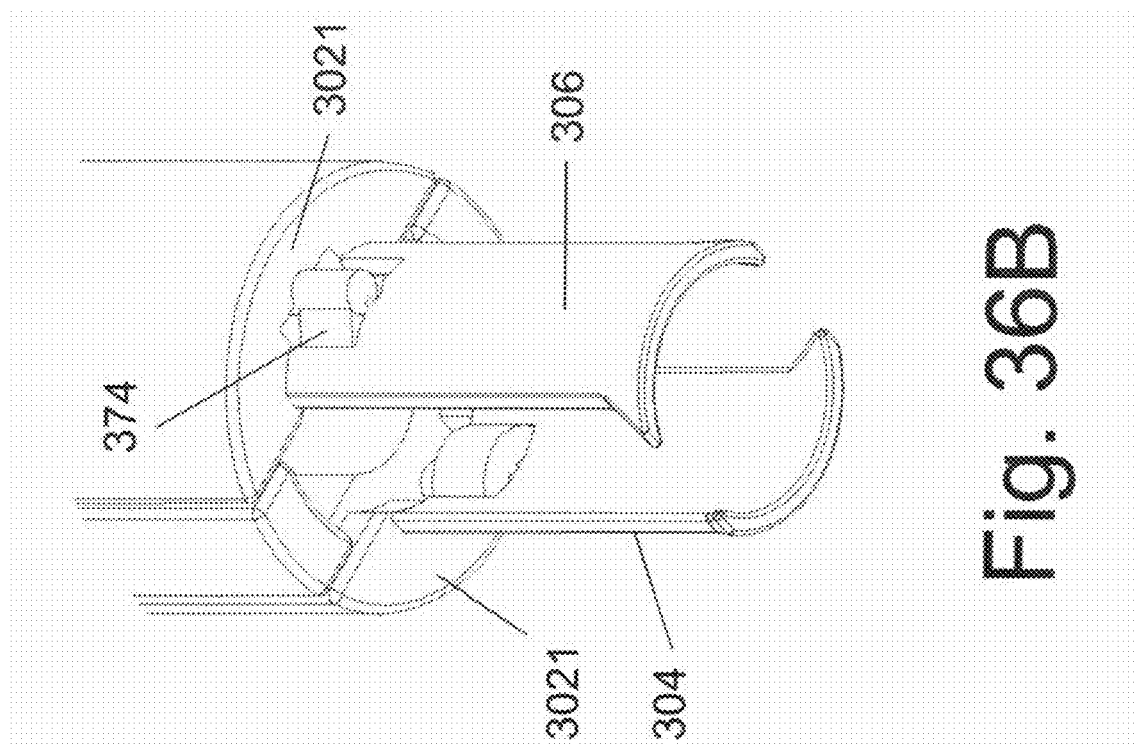
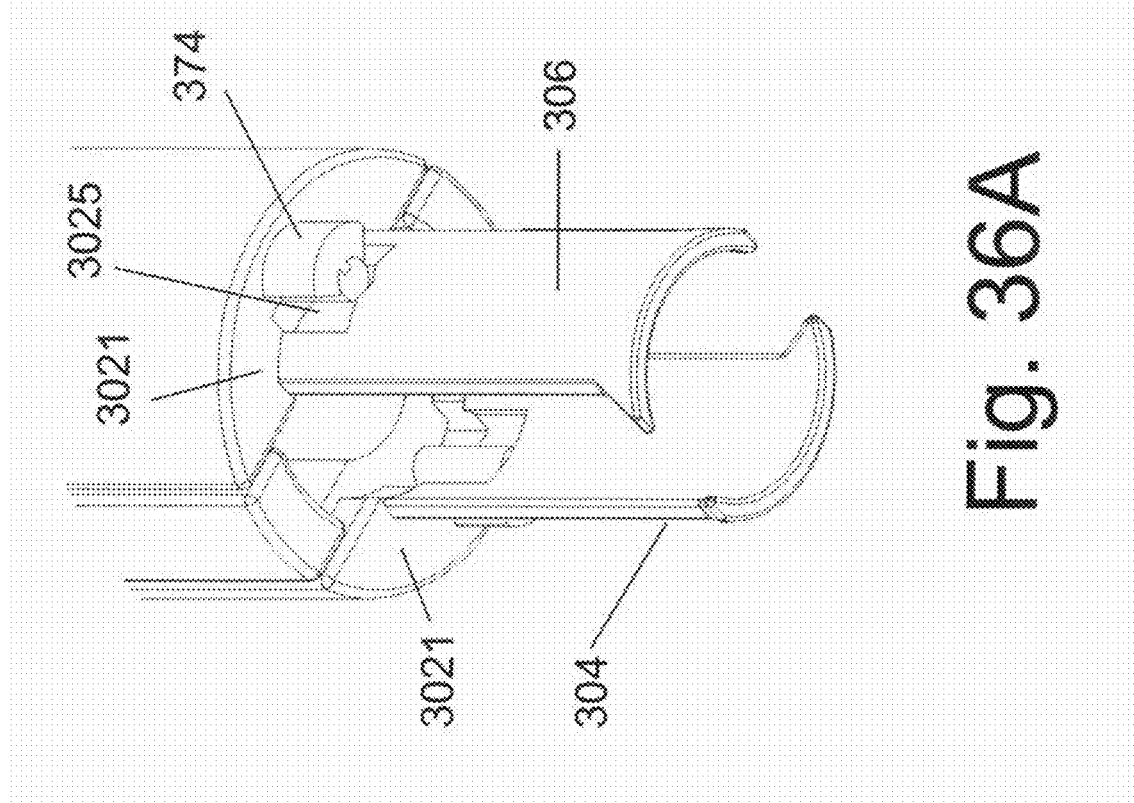

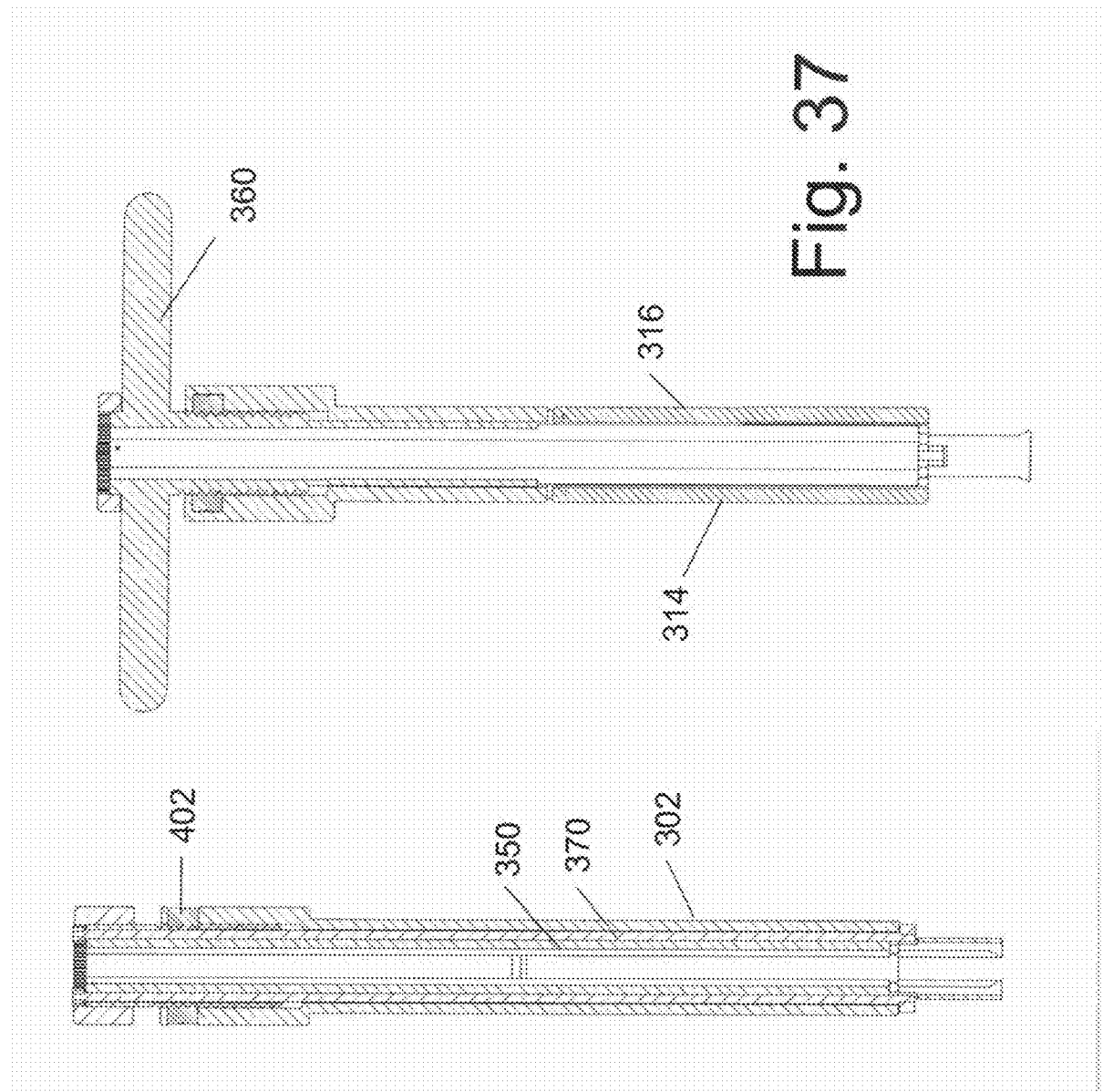

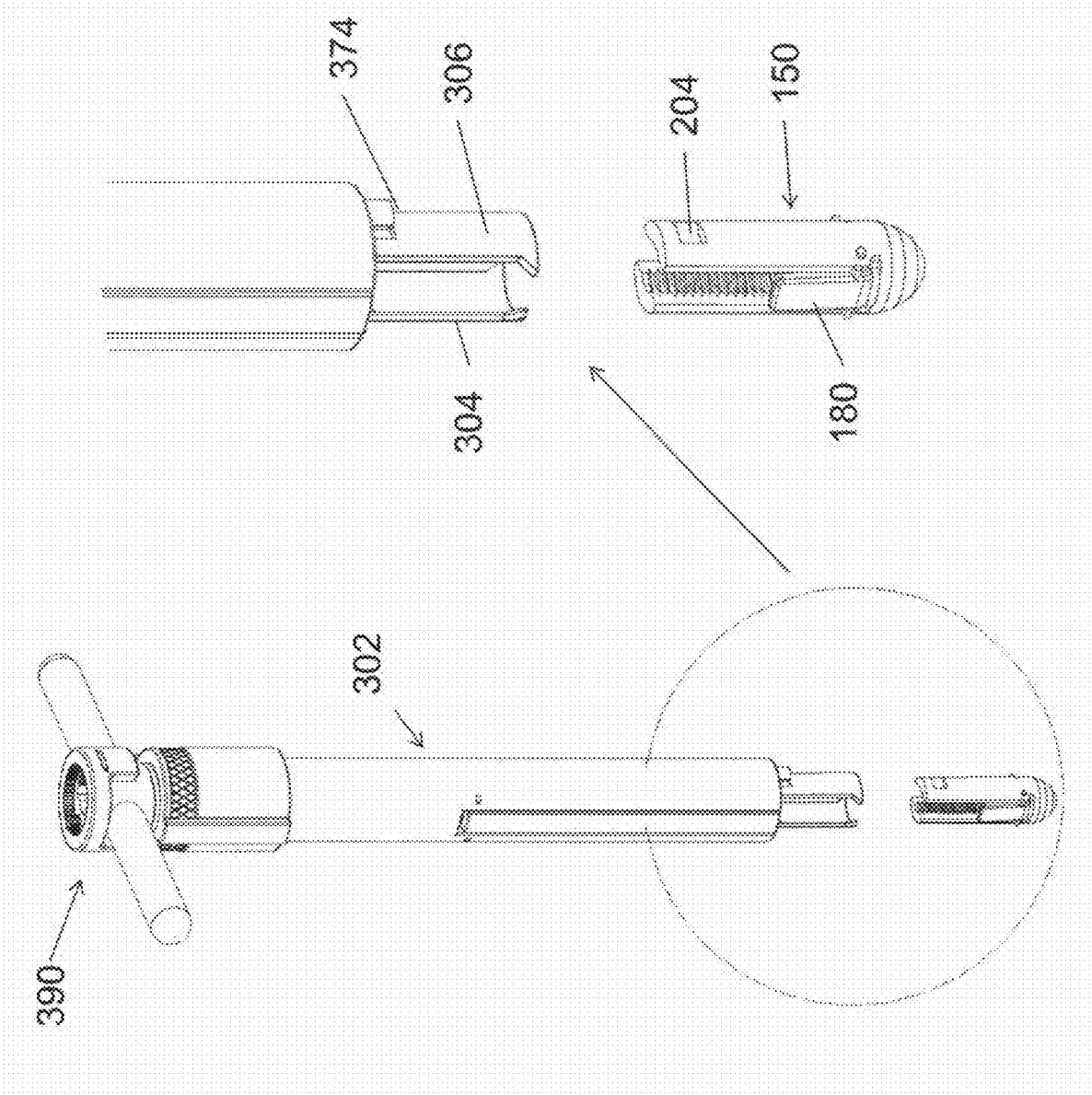

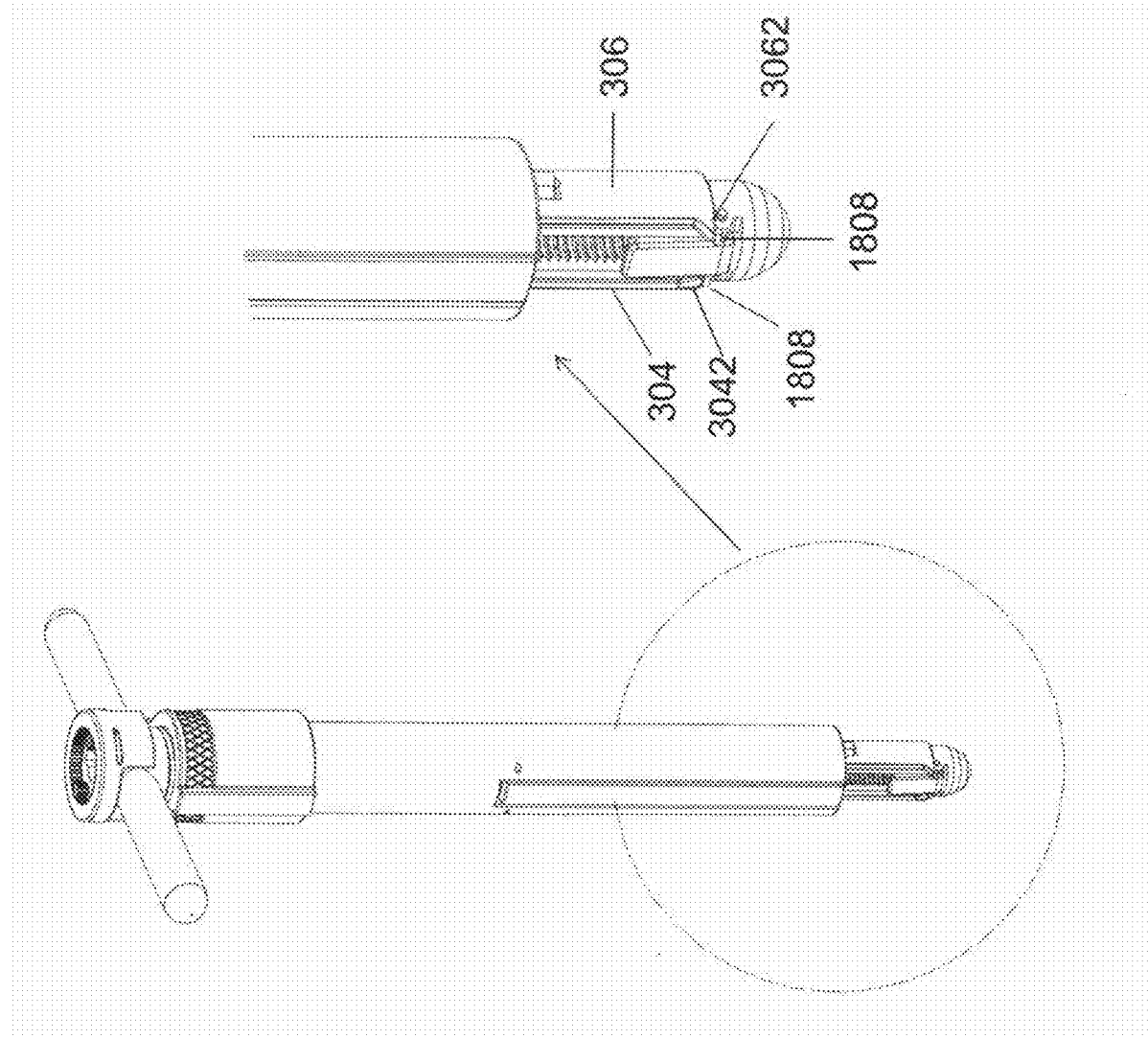

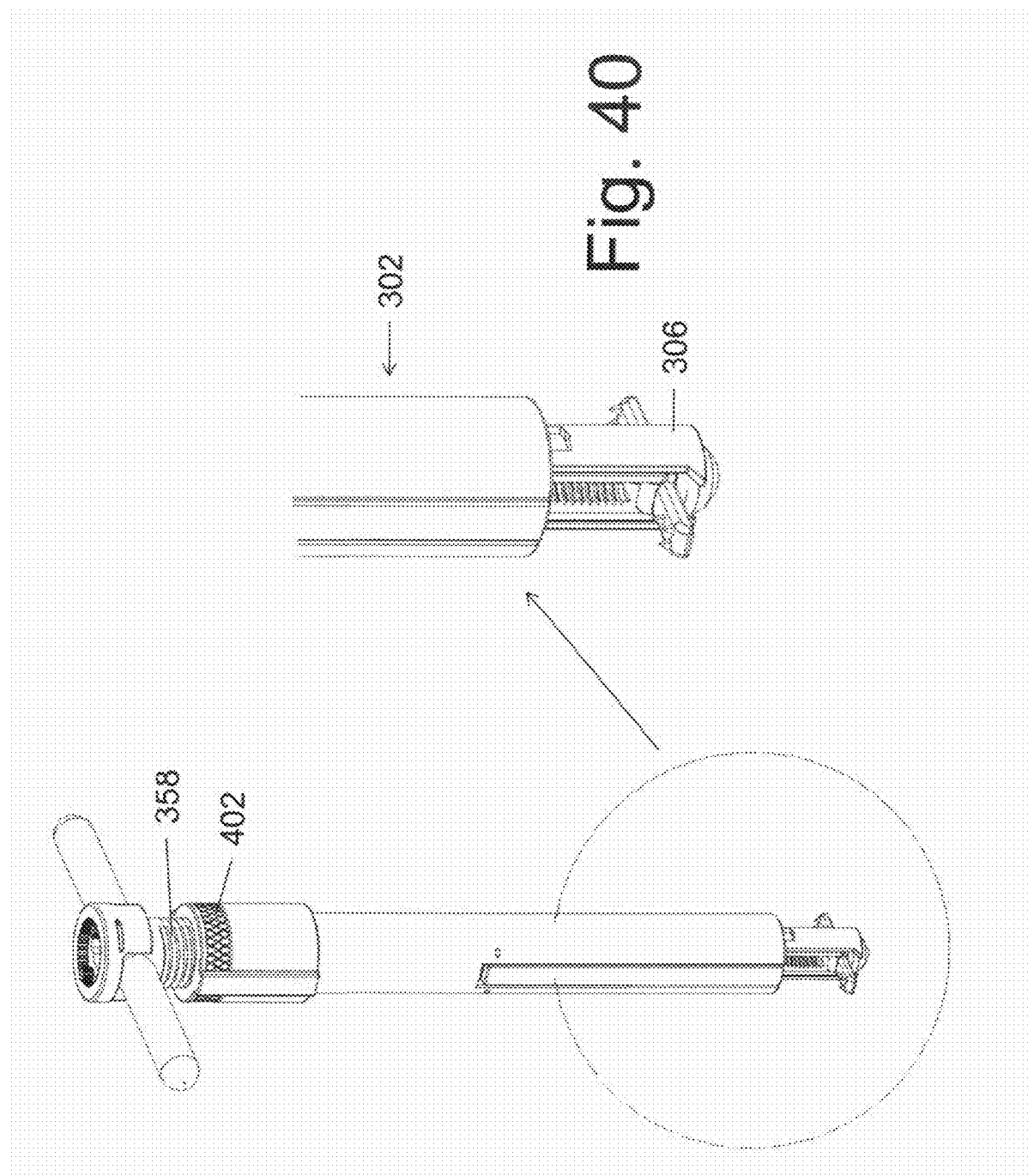

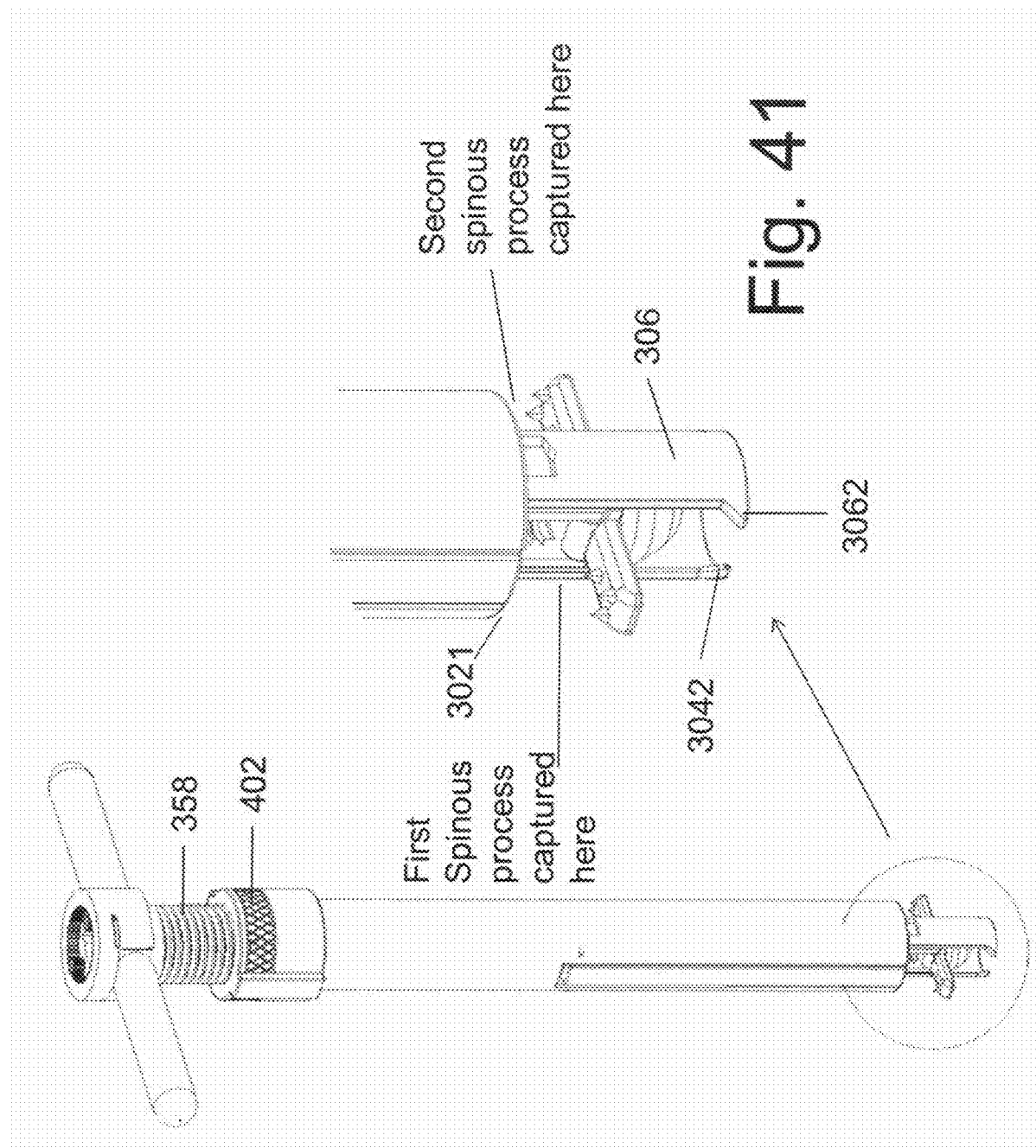

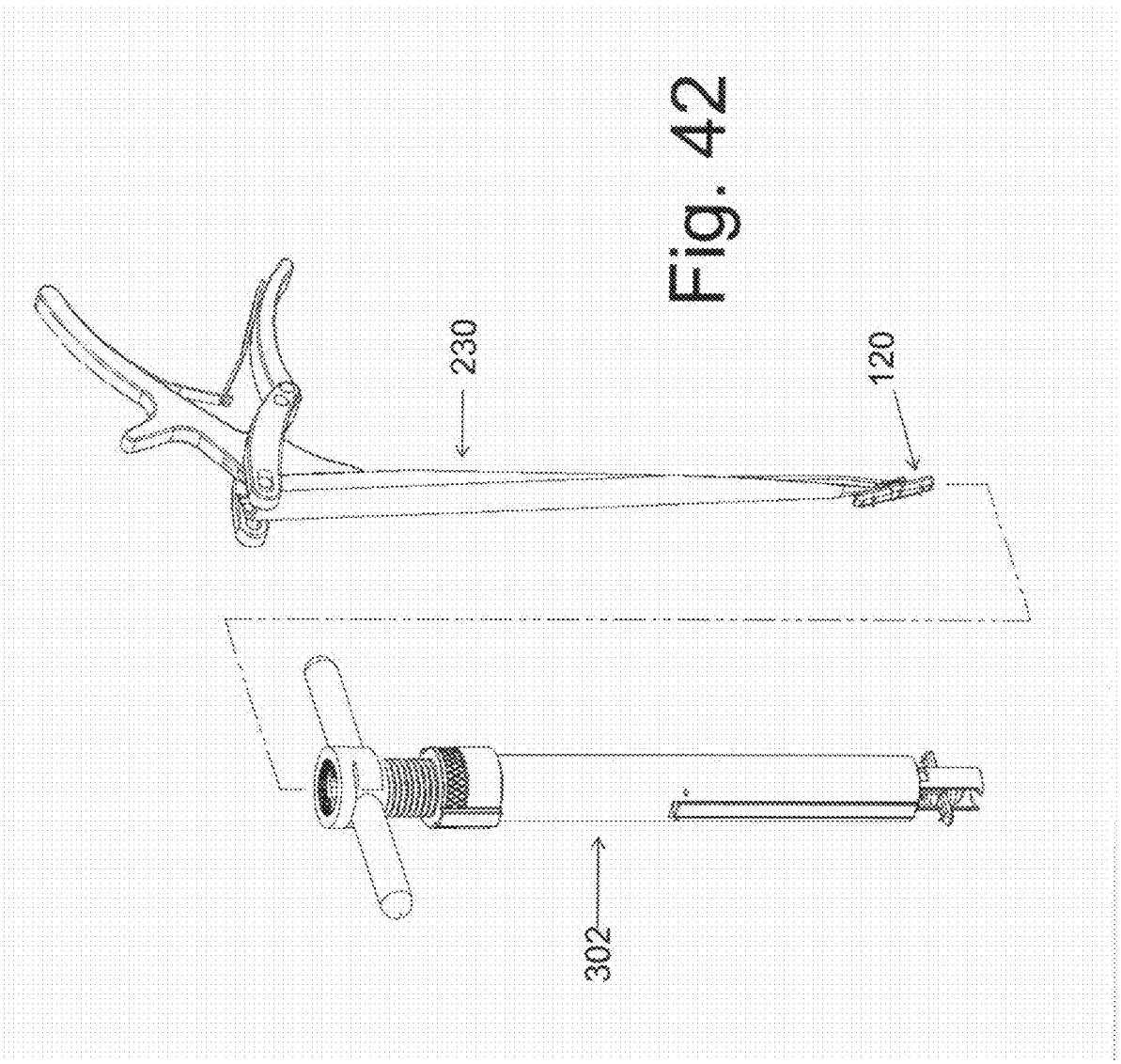

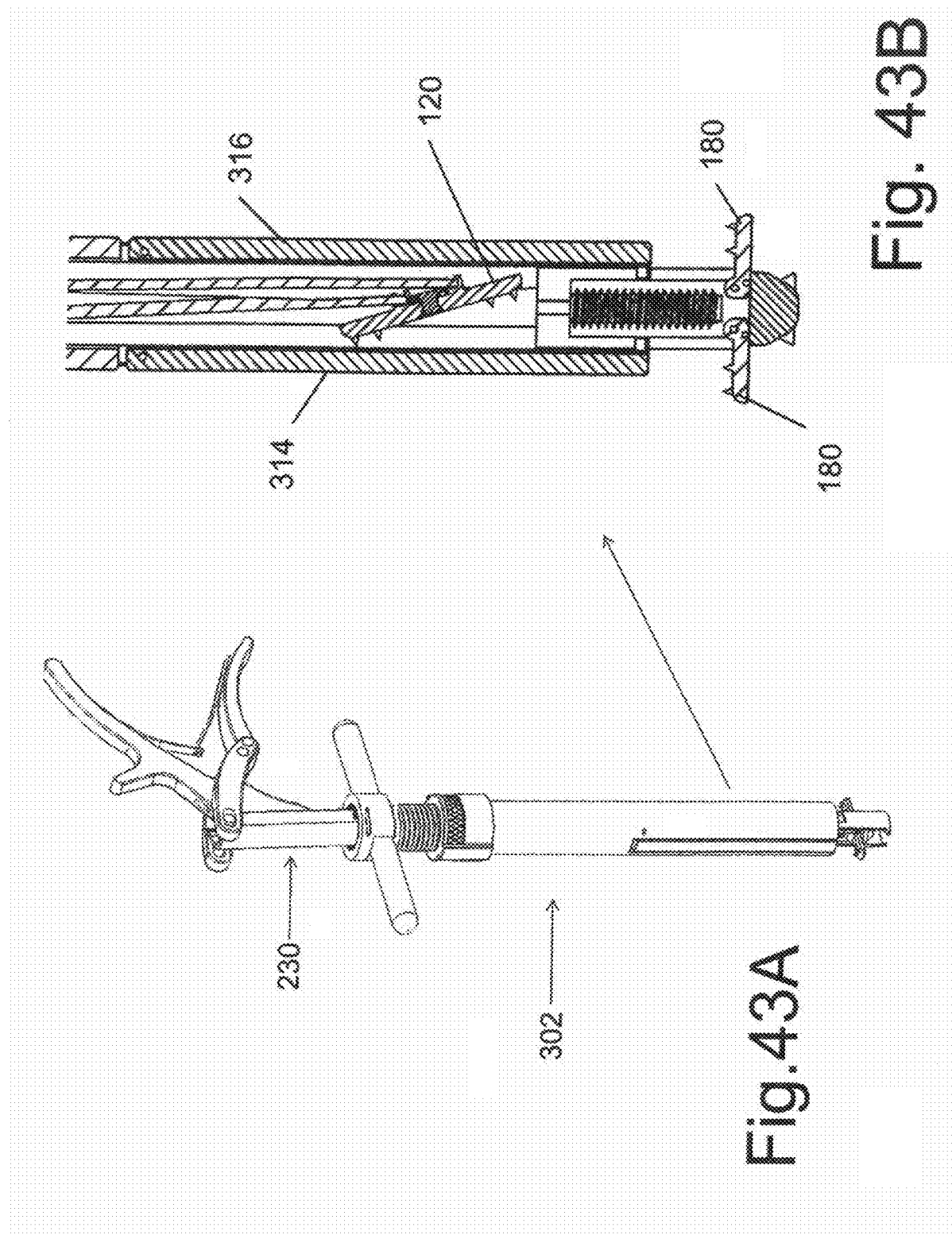

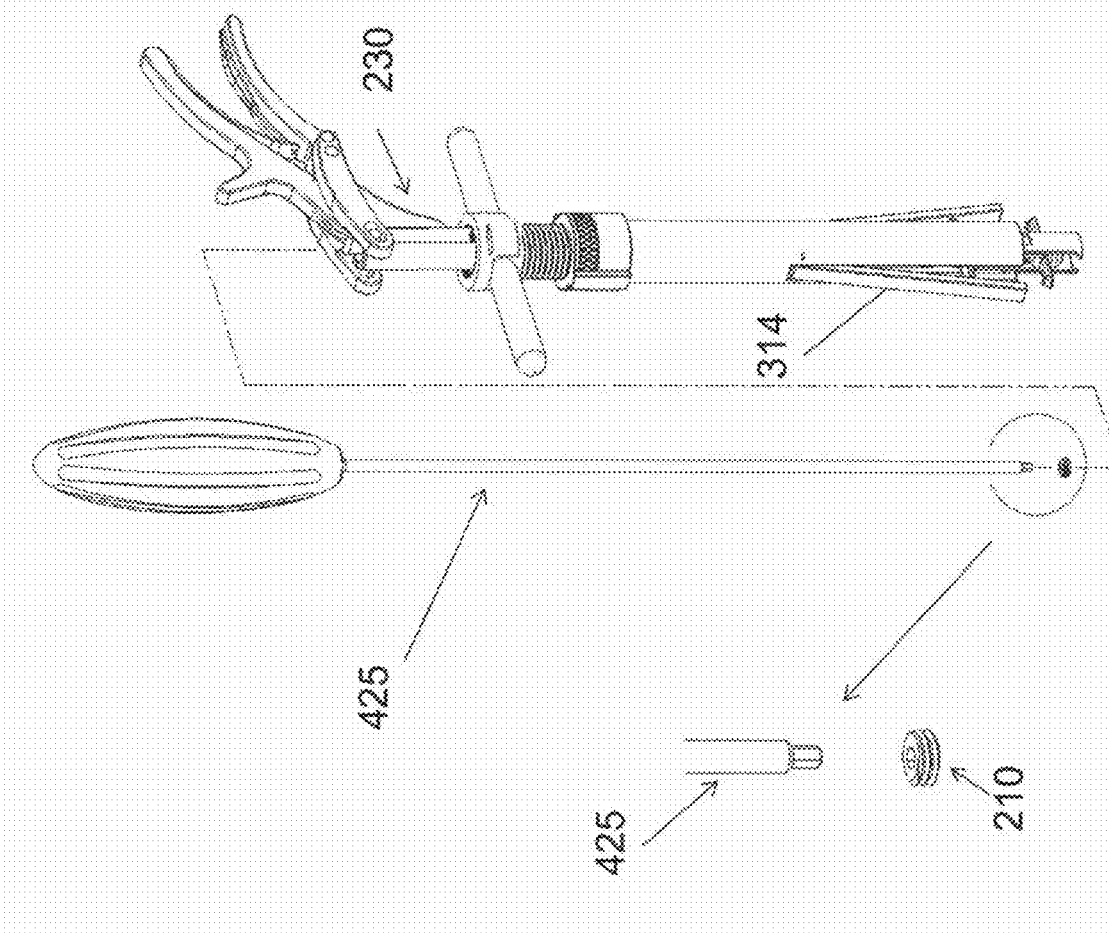

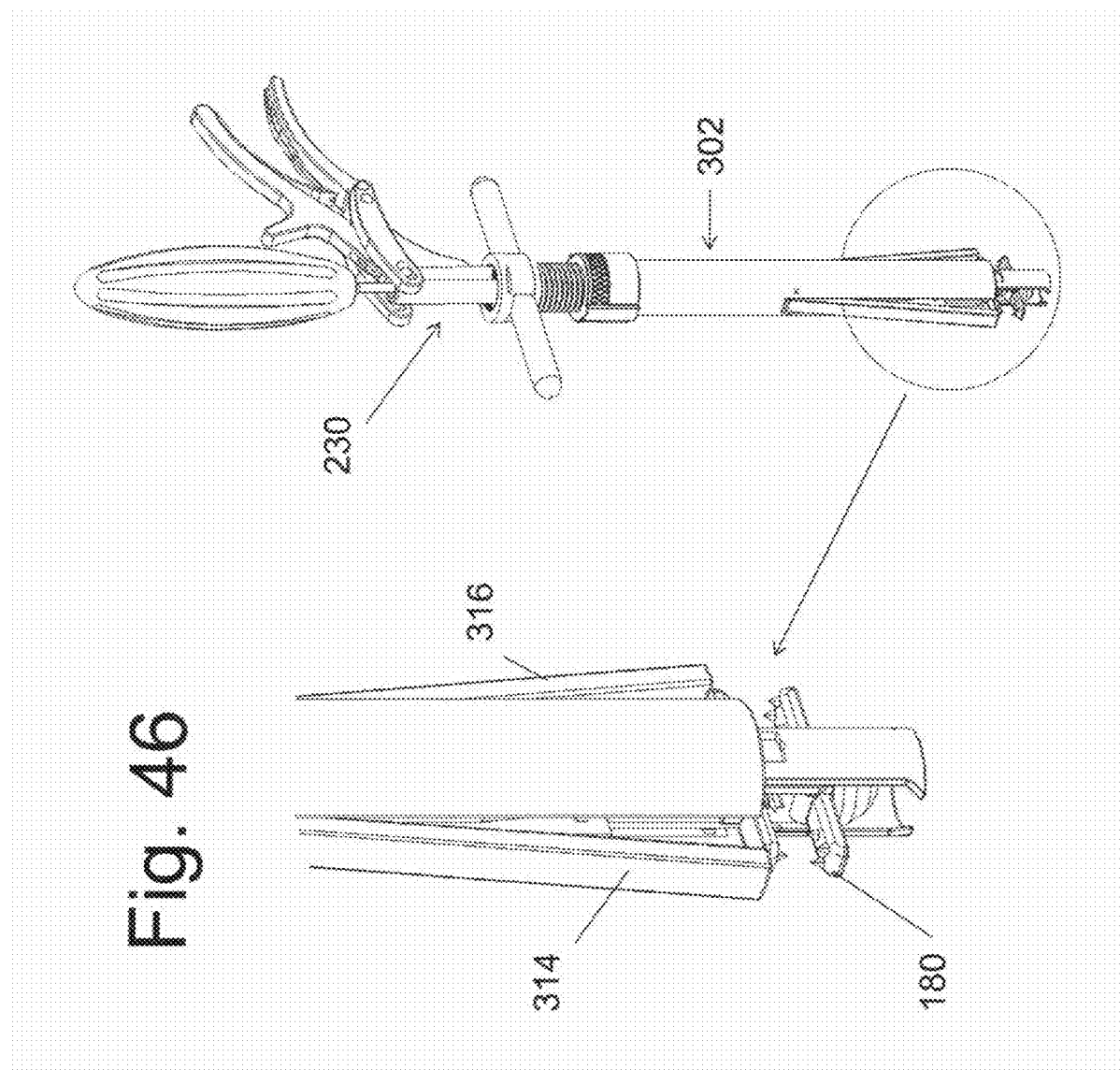

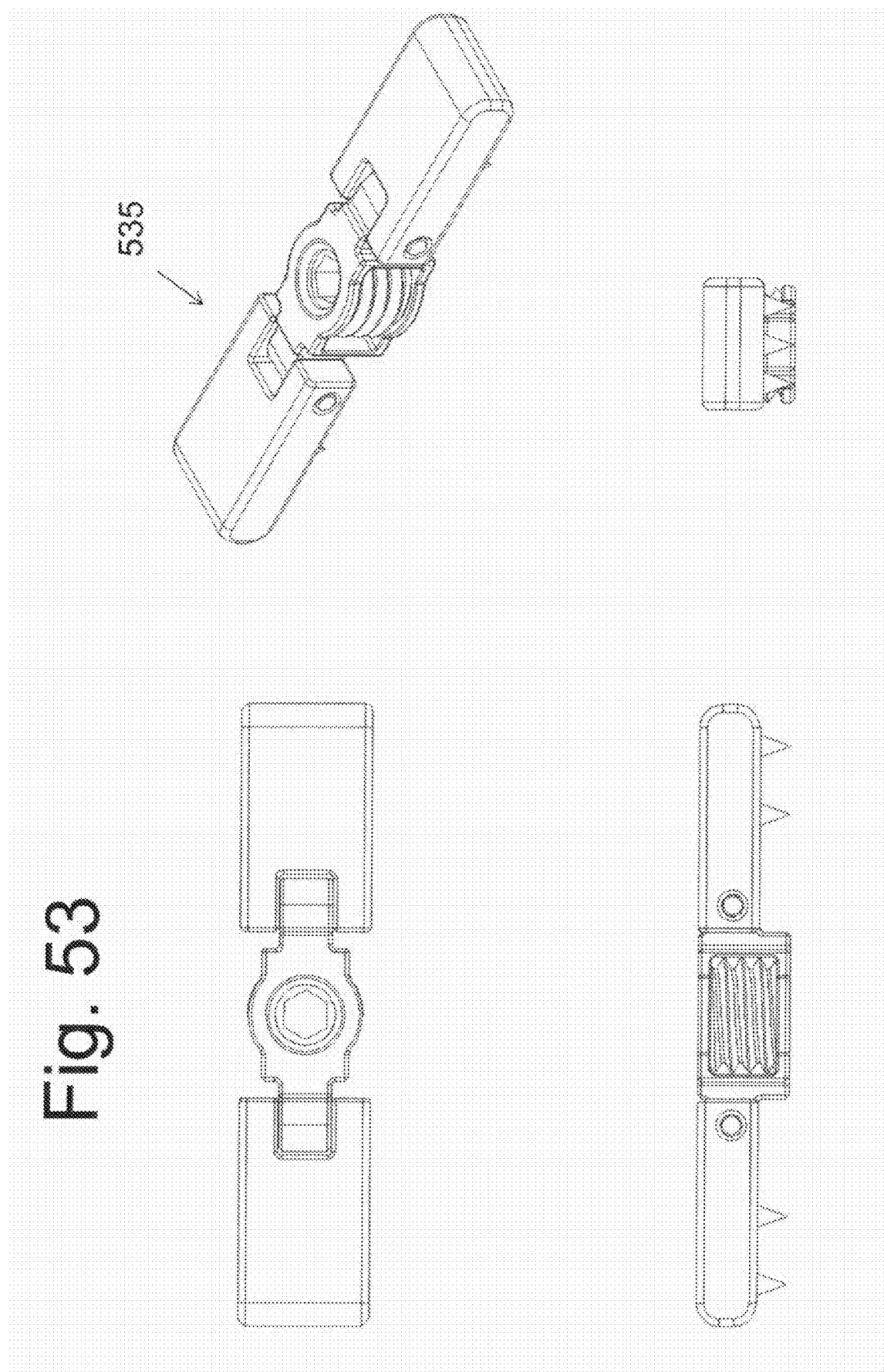

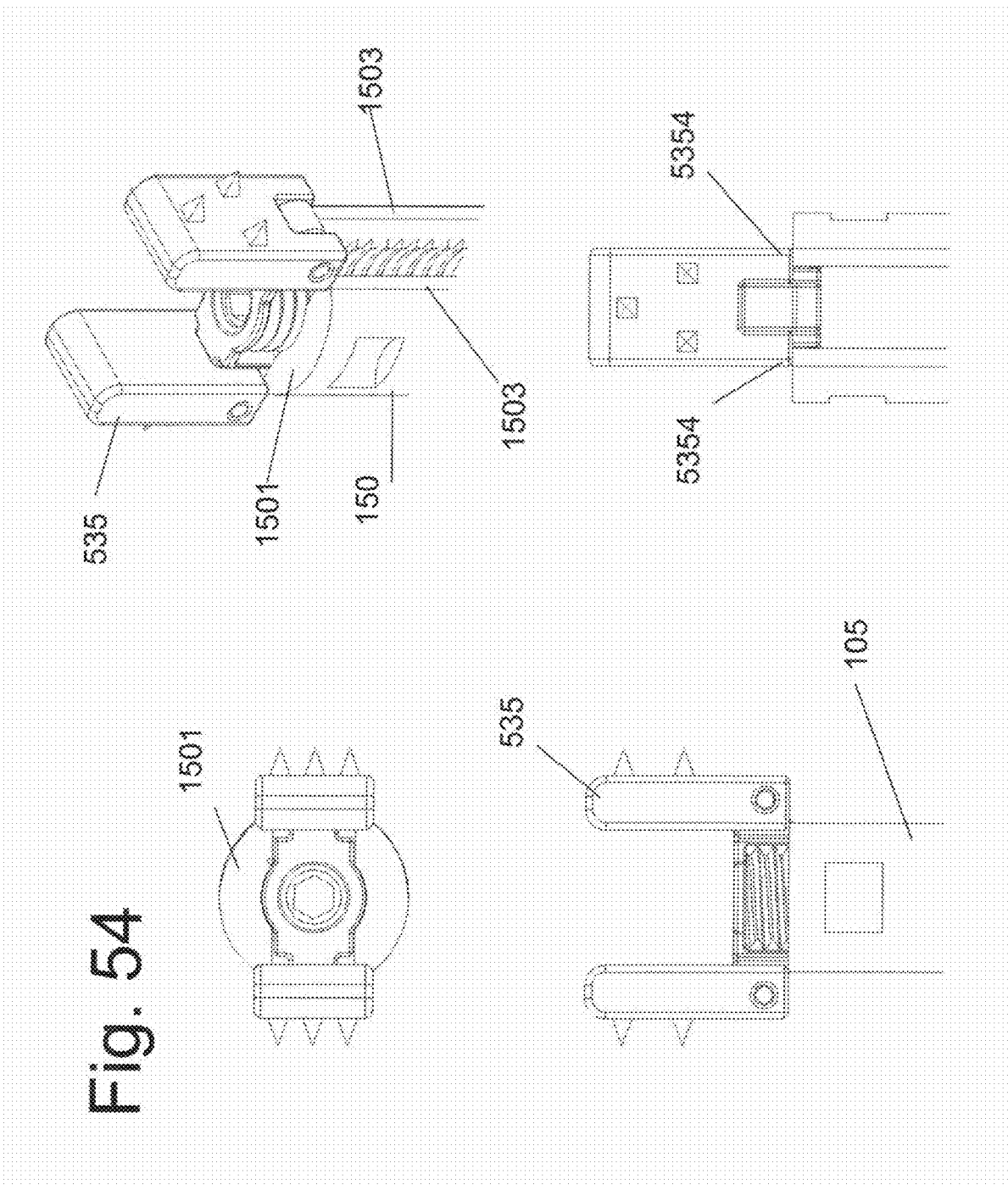

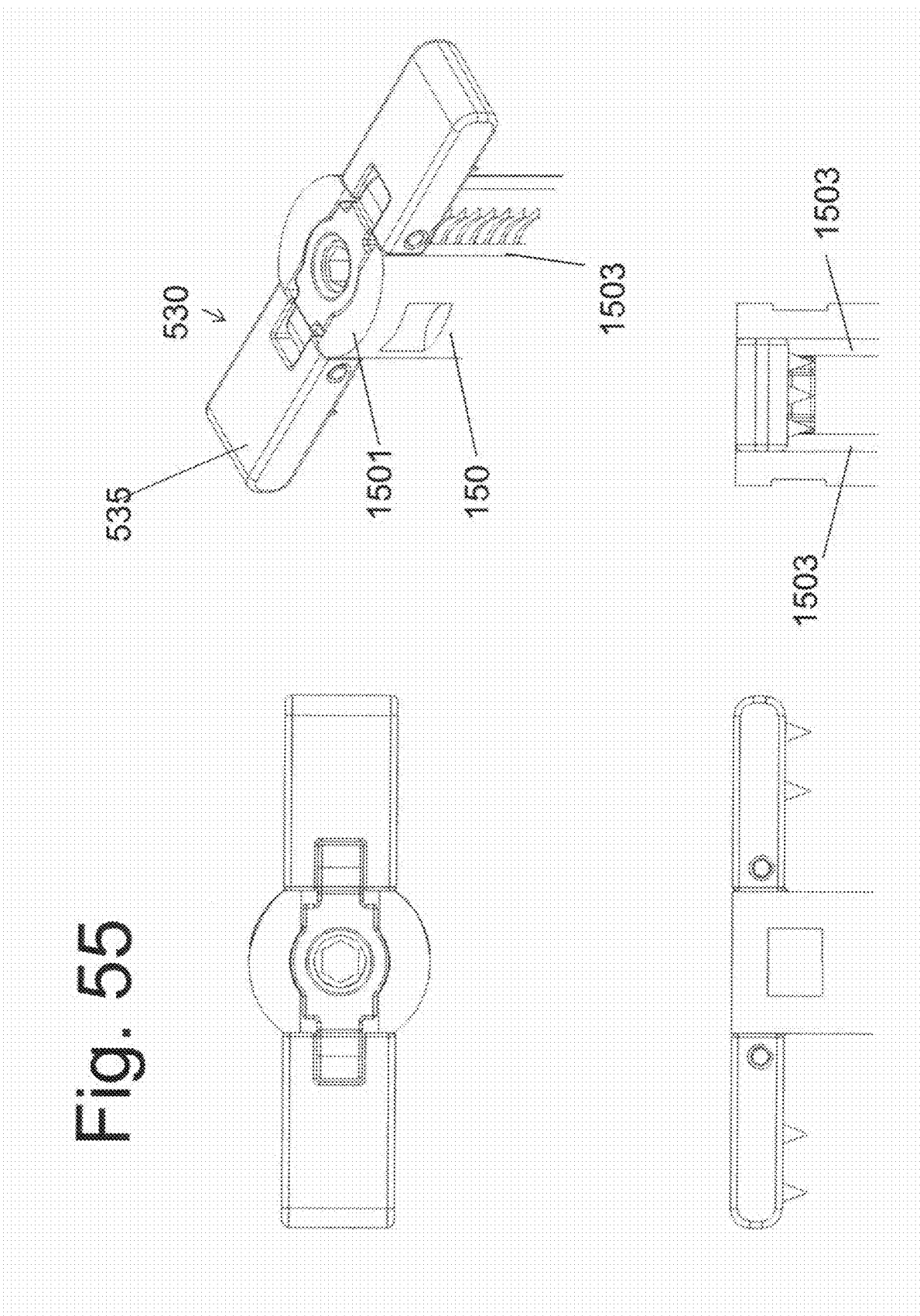

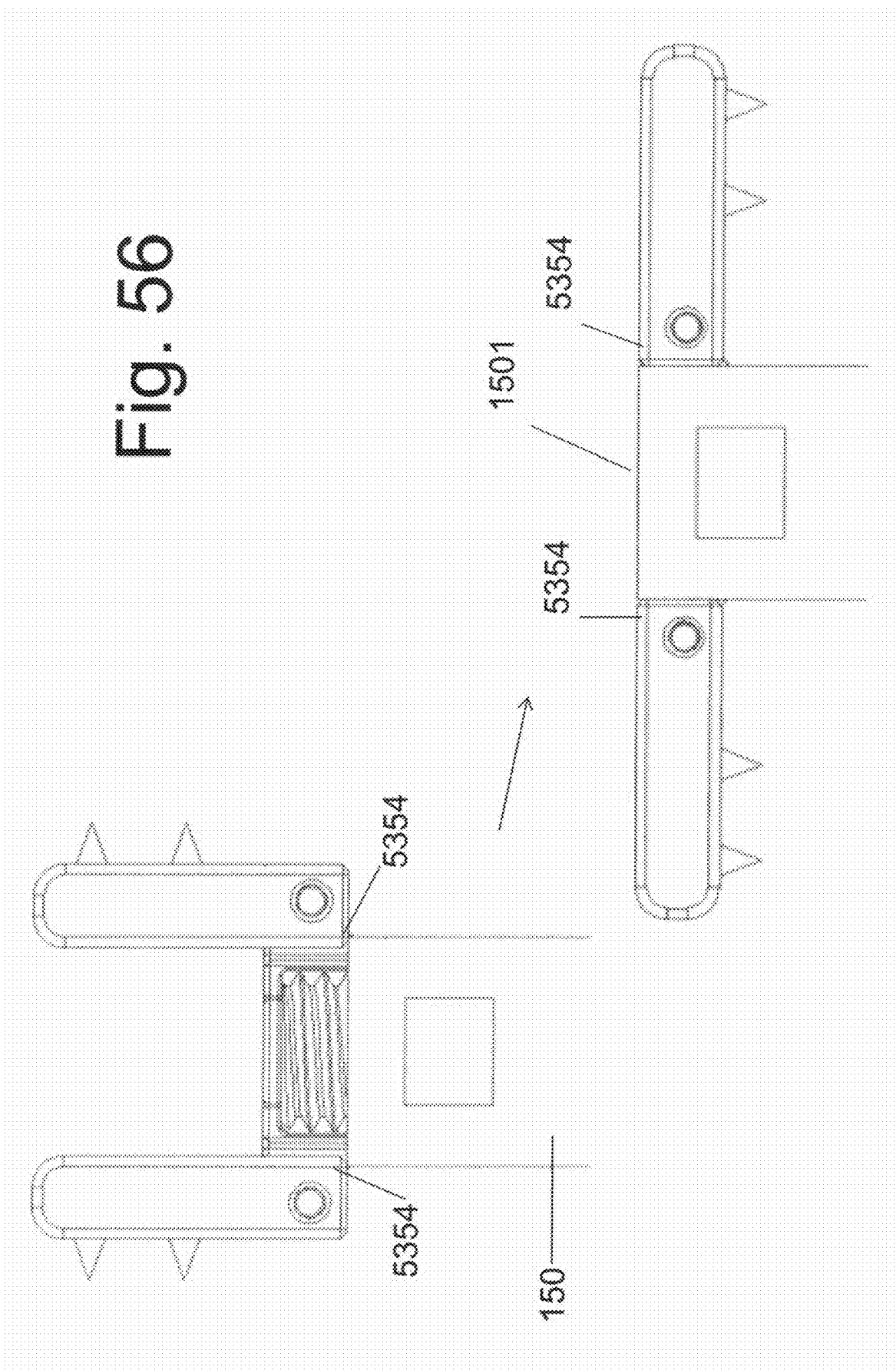

SPINOUS PROCESS FIXATION DEVICES AND METHODS OF USE

PRIORITY

This application is a continuation of and claims priority to co-pending and co-owned U.S. patent application Ser. No. 13/774,905 filed on Feb. 22, 2013 of the same title, and claims priority to U.S. Provisional Patent Application Ser. No. 61/634,022 filed Feb. 22, 2012 of the same title; each of the foregoing is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

This disclosure relates generally to bone fixation systems, components thereof, and methods of implant placement used to adjust, align and maintain the spatial relationship(s) of adjacent bones or bony fragments after surgical reconstruction of skeletal segments. In particular, this disclosure relates to devices that fixate the spinous processes at one vertebral level with the spinous process of another vertebra.

2. Description of Related Technology

Whether from degenerative disease, traumatic disruption, infection or neoplastic invasion, alteration in the anatomical relationships between the spinal vertebras can cause significant pain, deformity and disability. Spinal disease is a major health problem in the industrialized world and the surgical treatment of spinal pathology is an evolving discipline. The traditional surgical treatment of abnormal vertebral motion is the complete immobilization and bony fusion of the involved spinal segment and an extensive array of surgical techniques and implantable devices have been formulated to accomplish the treatment objective.

Regardless of the specific objectives of surgery, many surgeons employ implantable devices that maintain the desired spatial relationship(s) between adjacent vertebral bodies. The effectiveness of theses devices is critically dependant on adequate fixation into the underlying bone. While screw fixation into the pedicle portion of the vertebral body has emerged as a common method of device fixation, it remains a substantial operation with multiple shortcomings.

SUMMARY

The present disclosure satisfies the need for the percutaneous delivery of an implant that can rigidly fixate the spinous process of a first superior bone and a second inferior bone of a functional spinal unit.

In one aspect, a device is disclosed. In one embodiment, the device is adapted to forcibly clamp onto the spinous processes of each of the vertebral bones. The device is sized to permit sufficient space for the implantation of bone forming material (for bone fusion) within the interspinous space adjacent to it.

Additionally, or alternatively, the implant may in another embodiment be adapted to contain a bone forming material within an internal cavity, wherein the bone forming material forms a fusion between the first and the second vertebral bones through at least one opening of the internal cavity.

In another embodiment, the implant comprises: (i) an elongated body configured to extend along a longitudinal axis from a first proximal segment to a second distal segment, the elongated body comprising an internal bore configured to: accept a bone forming material therein, occupy at least a portion of an internal volume of the elongated body, and comprise at least one aperture configured to open onto an outer surface of the elongated body, (ii) at least one rotational bone abutment member configured to attach to the second distal segment of the elongated body and configured to rotate from a first orientation to a second orientation relative to the elongated body, (iii) at least one second bone abutment member configured to attach to the first proximal segment of the elongated body, and (iv) a locking mechanism positioned at the first proximal segment of the elongated body, the locking mechanism configured to be advanced in a first direction to produce movement of the at least one second bone abutment member towards the at least one rotational bone abutment member. Advancement of the locking mechanism in a second direction permits movement of the at least one second bone abutment member away from the at least one rotational bone abutment member.

In another aspect, a method for the percutaneous decompression of a spinal canal is disclosed. In one embodiment, the method comprises: (i) identifying on an imaging technique a spinal level to be implanted, (ii) making an incision lateral to a vertebral midline, (iii) advancing an orthopedic implant into an interspinous space of the spinal level to be decompressed, the orthopedic implant comprising an elongated body having an internal bore configured to accept a bone forming material therein, the internal bore occupying at least a portion of an internal volume of the elongated body and having an aperture opening onto an outer surface of the elongated body, (iv) attaching at least one rotational bone abutment member to a distal segment of the elongated body of the orthopedic implant, the at least one rotational bone abutment member configured to rotate from a first orientation to a second orientation relative to the elongated body, (v) attaching at least one second bone abutment member to a proximal segment of the elongated member, (vi) positioning a locking mechanism at the proximal segment of the elongated body, and (vii) advancing the locking mechanism along a first direction to produce movement of the at least one second bone abutment member towards the at least one rotational bone abutment member and capturing a spinous process of each vertebral bone abutting the implanted interspinous space between the at least one rotational bone abutment member and the at least one second bone abutment member. The advancement of the locking mechanism in a second direction opposing the first direction permits movement of the at least one second bone abutment member away from the at least one rotational bone abutment member.

In another aspect a method for treatment of a spinal segment is disclosed. In one embodiment, the spinal segment comprises first and second adjacent spinous processes, and the method comprises: (i) positioning a bone forming material within an internal bore of an orthopedic implant, the internal bore comprising at least 20% of an internal volume of the orthopedic implant and the bone forming material being configured to fuse with at least one of the first and second spinous processes, (ii) advancing a first segment of the orthopedic implant from a first ipsliateral side to a second contralateral side of an interspinous ligament that interconnects the first and second spinous processes, the first segment comprising a segment of an elongated body and at least a first bone abutment member coupled to the elongated body, (iii) rotating the first bone abutment member relative to the elongated body, the rotated first bone abutment member being at least partially positioned within the second contralateral side of the interspinous ligament, (iv) causing a surface of a second bone abutment member to abut a side surface of at least one of the first and second spinous processes, the second bone abutment member being at least partially positioned within the first ipsilateral side of the interspinous ligament, (v) translating the second bone abutment surface towards the first bone abutment surface by advancement of a locking mechanism of the orthopedic implant, and (vi) causing a forceful immobilization of at least one of the first and second spinous processes between the first and the second one abutment members.

In another aspect, a kit for positioning an orthopedic implant within a subject is disclosed. In one embodiment, the kit comprises: (i) an orthopedic implant comprising an elongated body extending along a longitudinal axis from a first proximal segment to a second distal segment, the elongated body comprising an external surface and an internal bore configured to occupy at least twenty percent of an internal volume of the elongated body, the internal bore further comprising an aperture configured to open onto the external surface, (ii) at least one rotatable bone abutment member attached to the second distal segment of the elongated member and configured to rotate from a first orientation to a second orientation relative to the elongated body, the at least one rotatable bone abutment member comprising an external surface positioned along the external surface of the orthopedic implant, and (iii) at least one elongated implant placement device configured to reversibly couple to the first proximal segment of the orthopedic implant, the at least one elongated implant placement device further configured to forcibly rotate the at least one rotatable bone abutment member from the first to the second orientation relative to the elongated body through an application of a force transmitted directly from the at least one elongated implant placement device to the external surface of the at least one rotatable bone abutment member.

The details of one or more embodiments are set forth in the accompanying drawings and description below. Other features, objects, and advantages will be apparent from the following description, the accompanying drawings and from the claims.

BRIEF DESCRIPTION OF THE DRAWINGS

FIG. 25 illustrates perspective views of the "open" and "closed" grip positions of the exemplary instrument of FIG. 18 producing translation of the two ends of the instrument.

FIG. 26A is an exploded view of an outer member of an exemplary instrument used to position the exemplary implant of FIG. 1 at the target interspinous space.

FIG. 26B illustrates the outer member of the exemplary instrument used to position the exemplary implant of FIG. 1 at the target interspinous space with side doors in a closed position.

FIG. 26C illustrates the outer member of the exemplary instrument used to position the exemplary implant of FIG. 1 at the target interspinous space with side doors in an open position.

FIG. 27A is a cross-sectional view of the outer member of the exemplary instrument used to position the exemplary implant of FIG. 1 at the target interspinous space.

FIG. 27B illustrate close-up views of the distal protrusions of the outer member of the exemplary instrument used to position the exemplary implant of FIG. 1 at the target interspinous space.

FIG. 28A is a close-up view of the proximal aspect of an inner member of the exemplary instrument used to position the exemplary implant of FIG. 1 at the target interspinous space.

FIG. 28B illustrate an oblique and a cross-sectional view of the inner member of the exemplary instrument used to position the exemplary implant of FIG. 1 at the target interspinous space.

FIG. 29A is an orthogonal view of the inner member of the exemplary instrument used to position the exemplary implant of FIG. 1 at the target interspinous space.

FIG. 29B is a cross-sectional view through the inner member of the exemplary instrument used to position the exemplary implant of FIG. 1 at the target interspinous space.

FIG. 30 is an exploded view of the inner member of the exemplary instrument used to position the exemplary implant of FIG. 1 at the target interspinous space illustrating the locking members positioned within the bores.

FIG. 31 is a close-up view of the projection of a top surface of the inner member of the exemplary instrument used to position the exemplary implant of FIG. 1 at the target interspinous space after advancement of a portion of a locking member thereof within a bore.

FIG. 32 is a perspective view of the assembled exemplary instrument used to position the exemplary implant of FIG. 1 at the target interspinous space FIG. 33 illustrates a coupling of the inner and outer members of the exemplary instrument used to position the exemplary implant of FIG. 1 at the target interspinous space.

FIG. 34 illustrates an assembled exemplary instrument used to position the exemplary implant of FIG. 1 at the target interspinous space in a locked position.

FIG. 35 illustrates an assembled exemplary instrument used to position the exemplary implant of FIG. 1 at the target interspinous space in an unlocked position.

FIG. 36A is a close-up view of the distal end of the assembled exemplary instrument of FIG. 34 in the locked position.

FIG. 36B is a close-up view of the distal end of the assembled exemplary instrument of FIG. 35 in the unlocked position.

FIG. 37 illustrates cross-sectional views of the assembled exemplary instrument used to position the exemplary implant of FIG. 1 at the target interspinous space.

FIG. 38 illustrates a perspective and close-up view of the positioning of the exemplary implant of FIG. 1 for coupling to the exemplary instrument for positioning the implant at the target interspinous space.

FIG. 39 illustrates a perspective and close-up view of the coupling of the exemplary implant of FIG. 1 within the exemplary instrument for positioning the implant at the target interspinous space.

FIG. 40 is a perspective view of rotation of the rotational members of the exemplary implant of FIG. 1 while within the exemplary instrument for positioning the implant at the target interspinous space.

FIG. 41 is a perspective view of positioning of the rotational members of the exemplary implant of FIG. 1 to capture the two spinous processes that border the target interspinous space while the implant is within the exemplary instrument for positioning the implant at the target interspinous space.

FIG. 42 illustrates a coupling of the exemplary instrument of FIG. 18 with the plate assembly of FIG. 14 attached thereto to the exemplary instrument of FIG. 32 for positioning the implant at the target interspinous space.

FIG. 43A illustrates another view of the coupling of the exemplary instrument of FIG. 18 with the plate assembly of FIG. 14 attached thereto to the exemplary instrument of FIG. 32 for positioning the implant at the target interspinous space.

FIG. 43B is a cross-sectional view of the coupling of the exemplary instrument of FIG. 18 with the plate assembly of FIG. 14 attached thereto to the exemplary instrument of FIG. 32 for positioning the implant at the target interspinous space.

FIG. 45 illustrates a coupling of an exemplary screw driver for attaching a locking nut to the implant assembly within the exemplary instrument of FIG. 18 and the exemplary instrument of FIG. 32 for positioning the implant at the target interspinous space.

FIG. 46 illustrates a perspective and close-up view of the coupling of the exemplary screw driver of FIG. 45 within the exemplary instrument of FIG. 18 and the exemplary instrument of FIG. 32.

FIG. 53 illustrates side, top, and perspective views of the alternative plate member of FIG. 51 in an "open" position.

FIG. 54 illustrates side, top, and perspective views of the alternative plate member of FIG. 51 in the "closed" position and attached to the fixation device of FIG. 1.

FIG. 55 illustrates side, top, and perspective views of rotation of the alternative plate member of FIG. 51 to the "open" position.

FIG. 56 illustrates side views of the transition of the alternative plate member of FIG. 51 from the "closed" to the "open" position.

Figure 1:
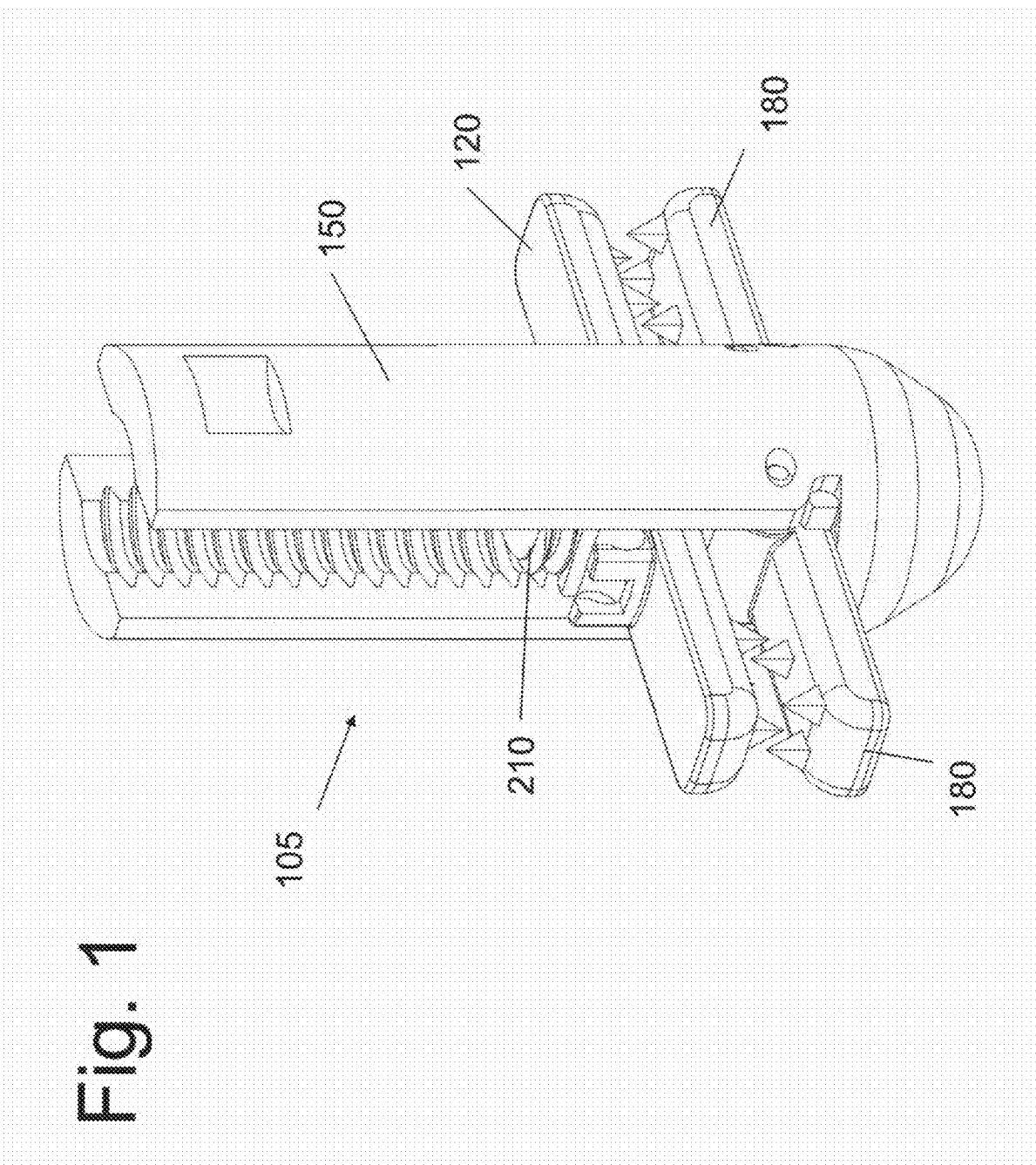
FIG. 1 is a perspective view of an embodiment of a fixation device in an assembled state according to the disclosure.

All Figures © Copyright 2013. Samy Abdou All rights reserved.

DETAILED DESCRIPTION

Described herein are, inter alia, devices and methods for the treatment of abnormal spinal stability and stenosis of the spinal canal by the implantation of orthopedic devices between skeletal segments. In an embodiment, a device is disclosed that rigidly fixates the spinous processes of two adjacent vertebral bones relative to one another. In one embodiment of device use, the implant is percutaneously placed into the interspinous space and may be used to provide decompression of spinal stenosis by retaining the spinous process in the distracted position. The implant also affixes the spinous processes of the vertebral bones on either side of the implanted interspinous space in order to retain and immobilize the vertebral bones relative to one another.

The device is inserted from a skin incision that is on a first side of the target interspinous. Rotatable members of the implant are advanced across the interspinous space from the first side (ipsilateral to site of skin incision) to a second contalateral side. The long axis of the implant is positioned substantially parallel to the trajectory used for implantation. After at least a distal segment of the rotatable members is positioned on the contralateral side of the interspinous space, at least one rotatable member is made to rotate, wherein, after rotation, the rotatable members had been substantially rotated by ninety degrees so that its long axis is now substantially along the long axis of the spinal column and perpendicular to the trajectory used for device implantation. In the rotated position, at least a distal segment of the rotated rotatable member is positioned to overly a segment of the lateral side surface of one of said first or the second spinous processes.

A second member is positioned on the side of the spinous process that is ipsilateral to the site of skin incision. A locking member is used to retain the second member attached to the device. As the locking member is advanced further, the spinous processes are forcibly captured between the rotatable members on the contralateral side of the spinous processes and the separate member positioned on the ipsilateral side of the spinous processes.

In another embodiment, the mechanisms for rotation of the rotatable arms as well as the locking mechanism are engaged and actuated through deployment instruments that are substantially positioned parallel to the trajectory of device implantation. Further, the engagble segments of these mechanisms are located on the ipsilateral side of the spinous processes at the time of engagement by the deployment instrument (whereas the rotatable members are located on the contralateral side of the spinous processes).

In an embodiment of implant use, the implant is percutaneously advanced into the posterior column of a spinal segment under radiographic guidance. The implant may be used at any spinal level but is particularly suited for implantation into the lumbar spine. While the disclosed implant may be used by itself to fuse the superior vertebral bone and the inferior vertebral bone that abut the implanted interspinous space, in other embodiments, the disclosed implant may be used with other orthopedic implants. The implant is particularly suited for use in the lumbar spine wherein another orthopedic implant is placed (at the same or at another operation) into the anterior column of the same spinal segment using a lateral approach to the anterior column. (The lateral-approach lateral fusion operations are collectively known as XLIF, DLIF and the like. An example of this method is disclosed in "Extreme Lateral Interbody Fusion (XLIF): a novel surgical technique for anterior lumbar interbody fusion" by Ozgur, Aryan et al. in *Spine J.* 2006 July-August; 6(4):435-43, which is hereby incorporated by reference in its entirety.)

In this way, both the anterior column implant (i.e., the one XLIF, DLIF and the like implant as well the other implant of the current application) may be placed through a single lateral skin incision or two closely adjacent skin incisions to provide a truly percutaneous or minimally invasive approach. Further, this method provides circumferential (i.e., anterior and posterior) expansion and decompression of the spinal canal so as to treat spinal stenosis though anterior and posterior decompression of the spinal canal. That is, placement of an anterior column implant (via XLIF, DLIF and the like) provides anterior decompression of the spinal column, whereas placement of the disclosed implant into the posterior column (between the spinous processes) provides posterior decompression of the spinal column—and both can be performed through a common flank approach (see FIG. 5).

Figure 7:
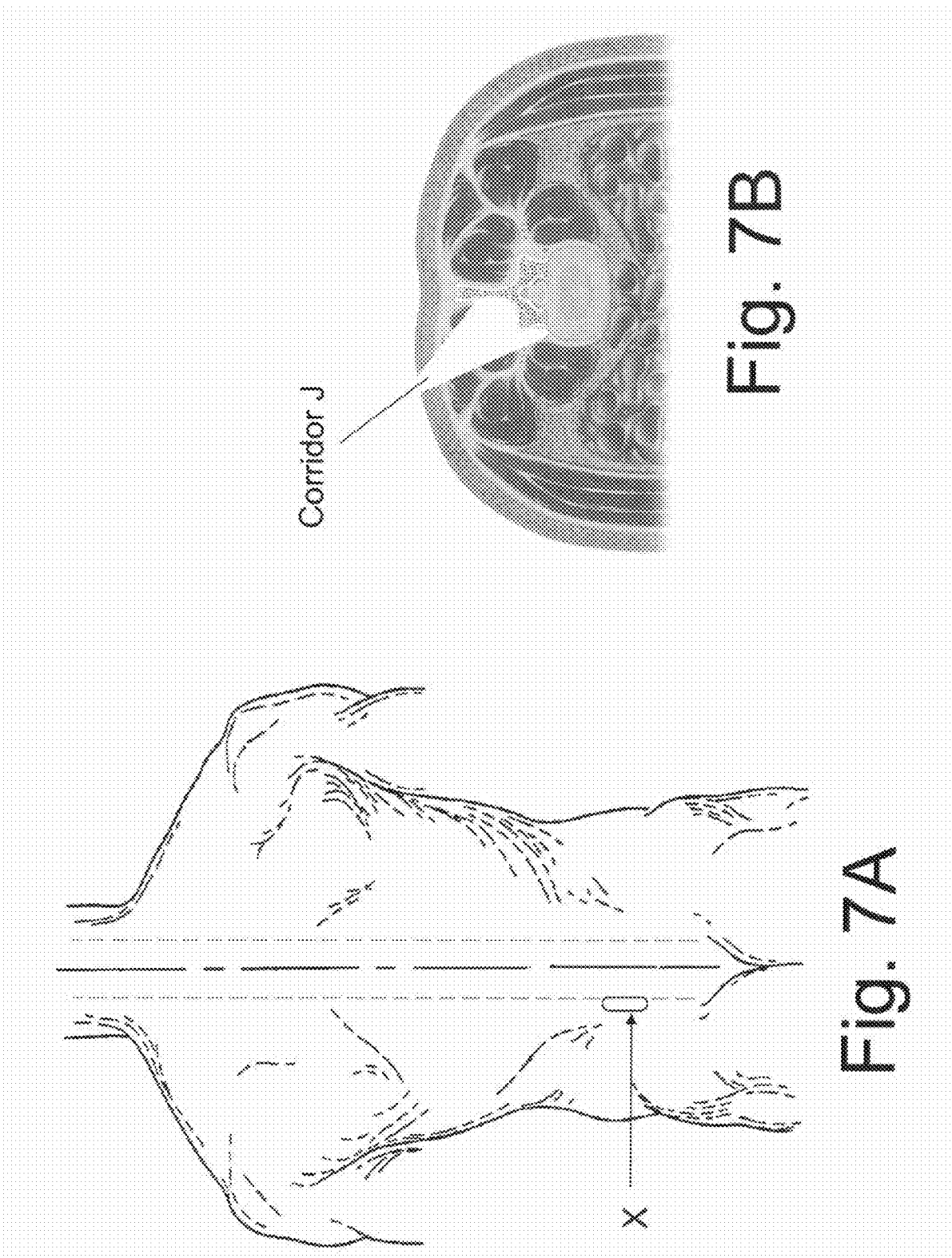
FIG. 7A is a schematic representation of the posterior aspect of a patient illustrating a TLIF incision location.
FIG. 7B is a cross sectional view of the torso at the level of the lumbar spine for use with the single incision approach.

In another embodiment of use, the device may be deployed through a single incision that is posterior and lateral to the transverse processes of the spinal level to be implanted (see FIG. 7). (A surgical procedure that employs a similar incision is known to those of ordinary skill in the art as TLIF.) Bone screws are advanced into the pedicle portion of bone on the side of the vertebrae that is ipsilateral to the incision. The screws are rigidly interconnected with a rod. The device disclosed herein is then placed through the same skin incision into the interspinous space. While contralateral pedicle screws may be also placed by the operating surgeon, the implanted interspinous device obviates the need for contralateral screw placement.

Figure 2:
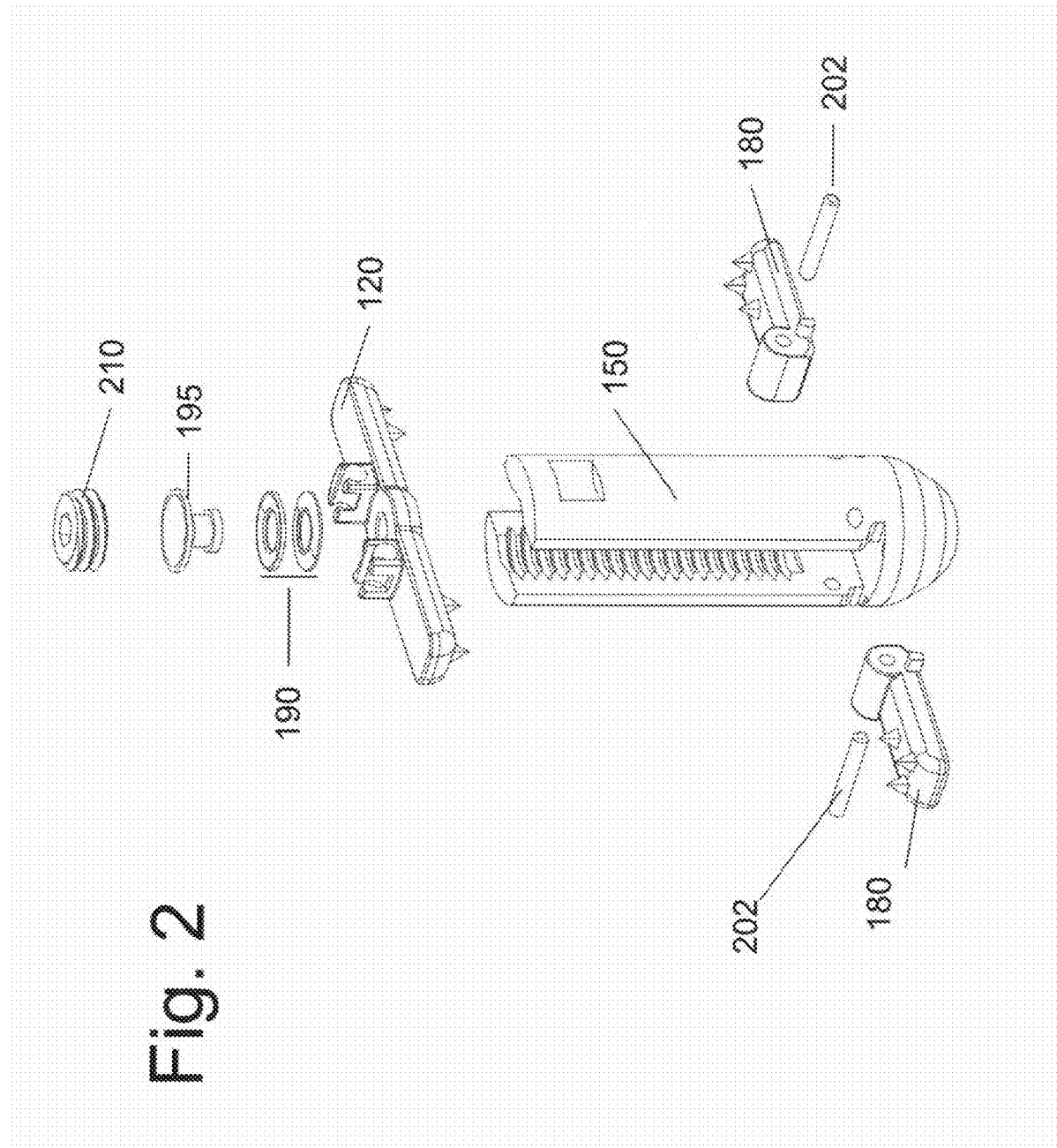
FIG. 2 is an exploded perspective view of the embodiment of the fixation device of FIG. 1.

FIG. 1 is a perspective view of an embodiment of a fixation device 105 in an assembled state. FIG. 2 shows a perspective view of the device 105 in an exploded view. The fixation device 105 is comprised of a plate member 120, rotation arms 180, and housing member 150—each of which will be described in more detail below. The fixation device 105 also includes a locking nut 210, retaining member 195 and spring members 190 (i.e., Belleville washers and the like).

The device 105 can be used to interconnect and fixate the spinous process of a first vertebral bone with the spinous process of a second adjacent vertebral bone. The device permits a surgeon to percutaneously implant it into the posterior column of the spine from a lateral, or flank incision, as will be discussed in more detail below. As previously discussed, the device is particularly useful in the fixation of the posterior spinal column of a target functional spinal unit of a spinal column—in conjunction with a lateral approach fusion of the disc space of the same target functional spinal unit.

As used herein, the anterior column generally designates a portion of the vertebral body and/or Functional Spinal Unit (FSU) that is situated anterior to the posterior longitudinal ligament. Thus, its use in this application encompasses both the anterior and middle column of Denis (see e.g., "The three column spine and its significance in the classification of acute thoracolumbar spinal injuries" by Denis, F. Spine 1983 November-December; 8(8):817 31, which is incorporated by reference in its entirety). The illustrations and definitions of anatomical structures are known to those of ordinary skill in the art. They are described in more detail in Atlas of Human Anatomy, by Frank Netter, third edition, Icon Learning Systems, Teterboro, New Jersey. The text is hereby incorporated by reference in its entirety. It should be appreciated that the directional language and terms regarding orientation such as upper, lower, upward, downward etc. are used merely for convenience of description and are not intended to be limiting.

Figure 3:
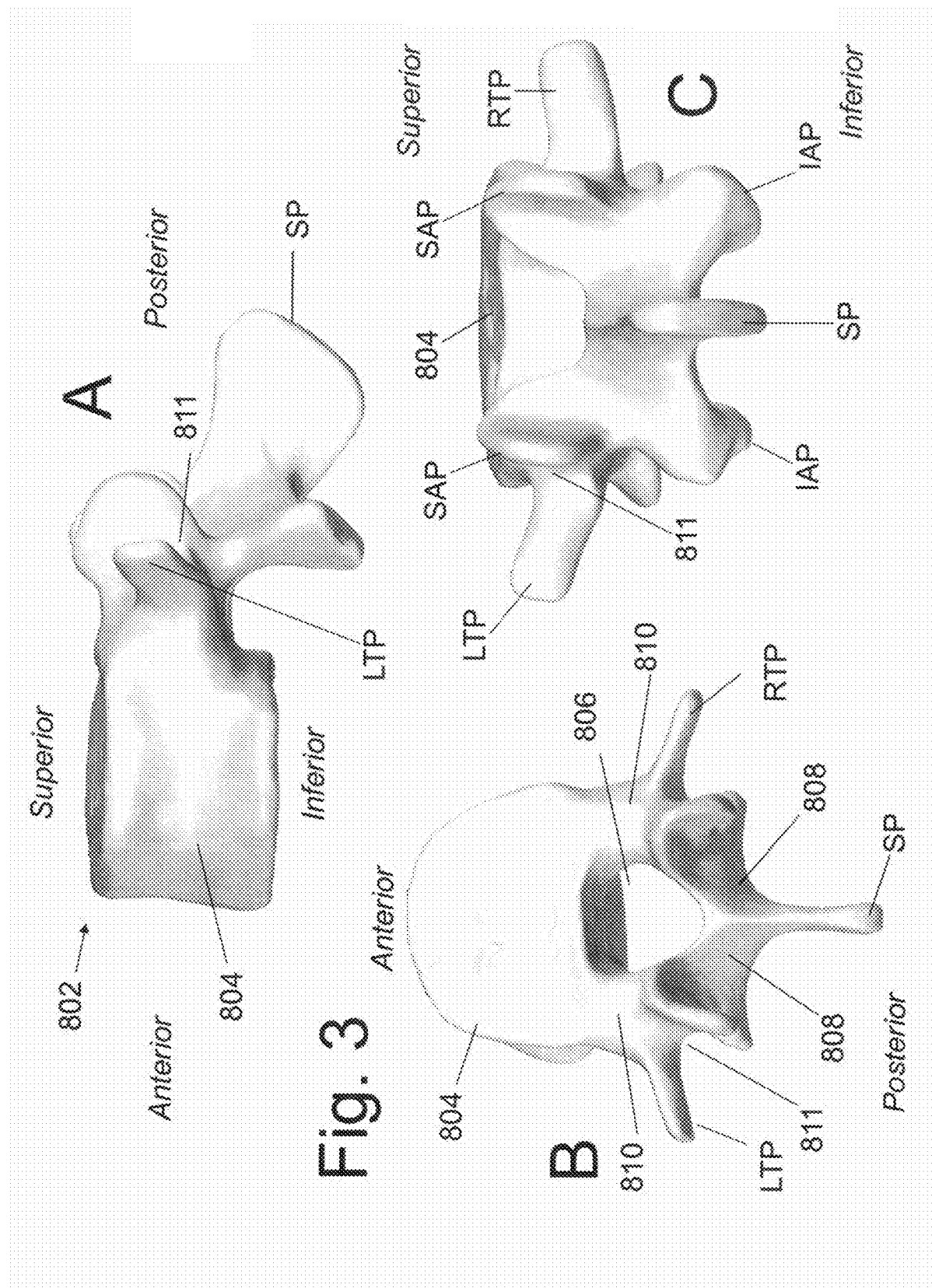
FIG. 3 illustrates diagrammatic representations of a spinal vertebral bone.

FIG. 3 illustrates diagrammatic representations of a spinal vertebral bone 802 in multiple views. For clarity of illustration, the vertebral bone of FIG. 3 and those of other illustrations disclosed herein are represented schematically and it should be appreciated that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. The disclosed devices and methods may be applied at any spinal level.

Vertebral bone 802 contains an anteriorly-placed vertebral body 804, a centrally placed spinal canal 806 and posteriorly-placed lamina 808. The pedicle segments 810 of vertebral bone 802 form the lateral aspect of the spinal canal 806 and connect the laminas 808 to the vertebral body 804. The spinal canal 806 contains neural structures such as the spinal cord and/or nerves. A midline protrusion termed the spinous process SP extends posteriorly from the medial aspect of laminas 808. A protrusion extends laterally from each side of the posterior aspect of the vertebral bone 802 and is termed the transverse process TP. A right transverse process RTP extends to the right and a left transverse process LTP extends to the left. A superior protrusion extends superiorly above the lamina 808 on each side of the vertebral midline and is termed the superior articulating process SAP. An inferior protrusion extends inferiorly below the lamina 808 on each side of the vertebral midline and is termed the inferior articulating process IAP. Note that the posterior aspect of the pedicle 810 can be accessed at an indentation 811 in the vertebral bone 802 between the lateral aspect of the SAP and the medial aspect of the transverse process TP. In surgery, it can be common practice to anchor a bone fastener into the pedicle portion 810 of a vertebral bone 802 by inserting the fastener through indentation 811 and into the underlying pedicle 810.

Figure 4:
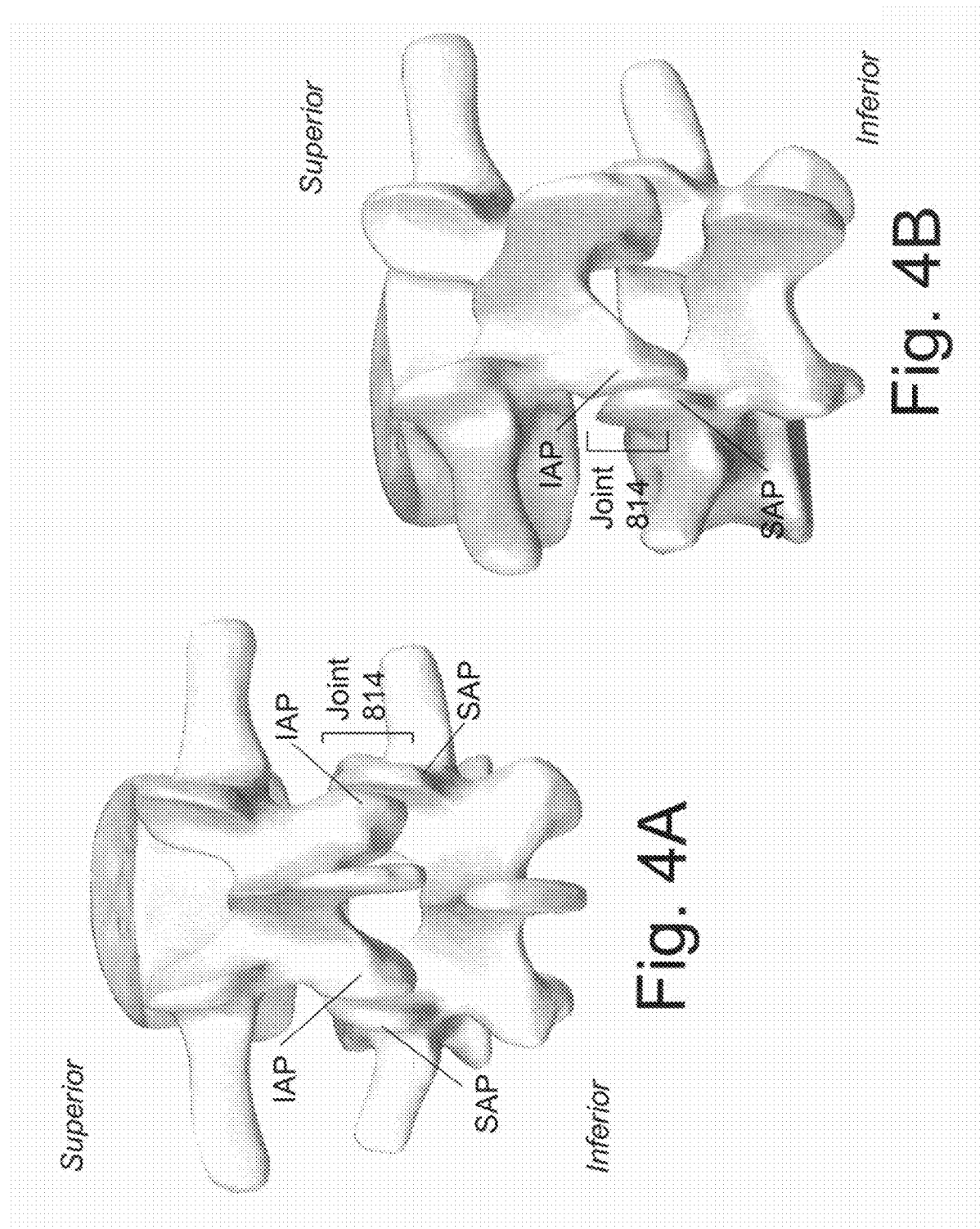
FIG. 4A is a posterior view of an Functional Spinal Unit (FSU) illustrating a posterior surface of the adjacent vertebrae of and the articulations between them.
FIG. 4B is an oblique view of the FSU of FIG. 4A, illustrating a posterior surface of the adjacent vertebrae of and the articulations between them.

FIGS. 4A and 4B illustrate a FSU, which includes two adjacent vertebrae and the intervertebral disc between them. The intervertebral disc resides between the inferior surface of the upper vertebral body and the superior surface of the lower vertebral body, although it is not specifically shown in the figures. FIG. 4A shows the posterior surface of the adjacent vertebrae and the articulations between them. FIG. 4B shows an oblique view. The FSU contains a three joint complex between the two vertebral bones, with the intervertebral disc comprising the anterior joint. The posterior joints include a facet joint 814 on each side of the midline, wherein the facet joint 814 contains the articulation between the IAP of the superior vertebral bone and the SAP of the inferior bone.

The interspinous space is generally defined as the space immediately between the spinous processes of a superior vertebral bone and the spinous process of an immediately adjacent inferior vertebral bone. The interspinous space is limited anteriorly by the spinal canal 806 and posteriorly by the posterior tip of the spinous processes. For the purpose of this application, the right lateral aspect of the interspinous space is limited by the right lateral side of the spinous processes whereas the left lateral aspect of the interspinous space is limited by the left lateral side of the spinous processes. Note that the spinous processes of adjacent vertebral bones may be rotated in the axial plane relative to one another because of biological and/or individual variation (schematically shown in FIG. 4A). The interspinous space would continue to be defined as residing between the spinous processes of the superior and inferior vertebral bones.

Figure 8:
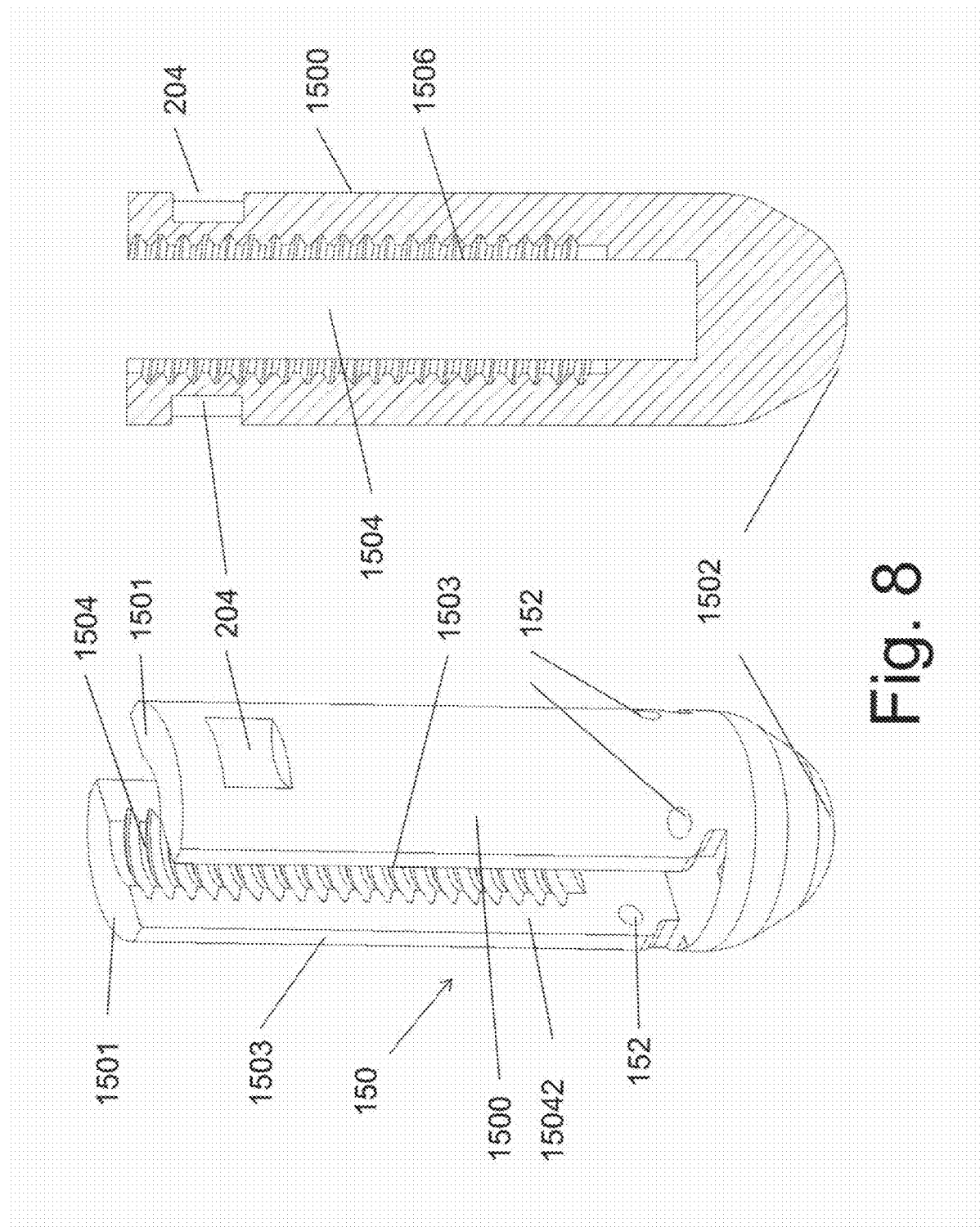
FIG. 8 illustrates perspective and cross-sectional views of the housing member of the fixation device of FIG. 1.
Figure 9:
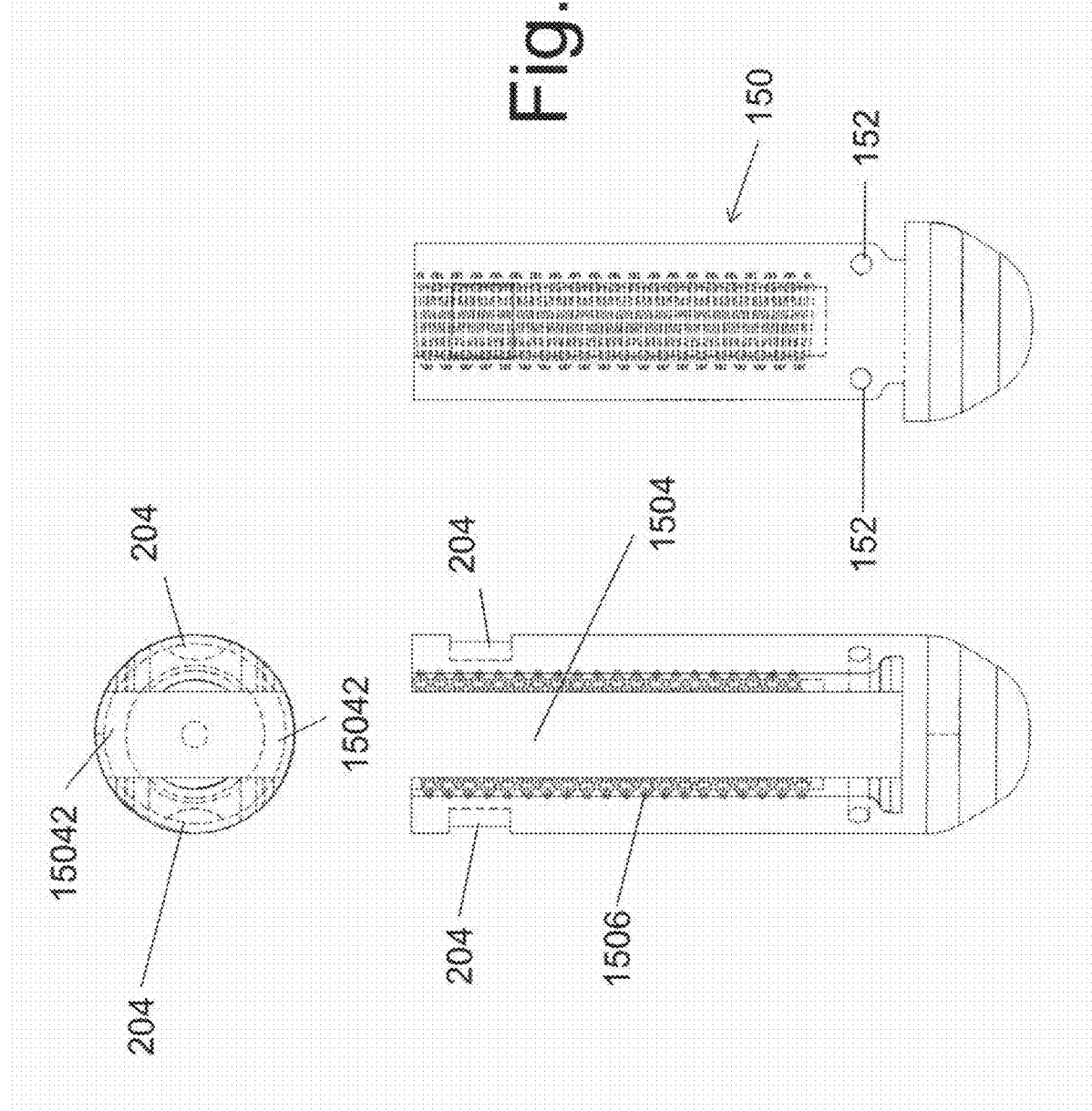
FIG. 9 illustrates additional cross-sectional views of the housing member of the fixation device of FIG. 1.

With respect to FIGS. 8 & 9, the housing member 150 extends from a proximal end to a distal end 1502 along the direction of a longitudinal axis. The housing member is a generally cylindrical device having a tapered, closed end 1502 and an opposing end 1501. Housing member 150 comprises an external surface 1500. The opposing end 1501 contains an internal bore 1504 that extends substantially along the central axis. The wall of bore 1504 contains threads 1506. Bore holes 152 accept pins 202 that retain rotational members 180. Recess 204 accepts a protrusion 374 of locking member 370 of a placement instrument that is used to guide the implant to the implantation side.

As shown in FIG. 8, the internal bore 1504 is open onto the external surface 1500 and the space external to member 150 through at least one side aperture 15042 that emerges between the surfaces 1503. In one embodiment, the bore 1504 is open onto the external surface 1500 through at least two opposing side surfaces (as shown in FIG. 9). In this way, the bore 1504 may accept a bone forming material that is configured to form a bony fusion with a bony surface external to member 150. In one variant, the bony surface is positioned to abut at least a segment of an external surface of member 150. It is appreciated that the bore 1504 may occupy any percentage of the internal volume of member 150. For example, the bore 1504 may occupy at least 80% of the internal volume of member 150. In another particular embodiment, the bore 1504 occupies at least 60% of the internal volume of member 150. In yet another example, the bore 1504 occupies at least 40% of the internal volume of member 150. In another example, the bore 1504 occupies at least 20% of the internal volume of member 150. Side aperture(s) 15042 must be of sufficient size to permit a bony fusion between the bone forming material of bore 1504 and the bony structure positioned outside of member 150. That is, the aperture(s) 15042 are sized to allow enough bone formation to immobilize member 150 relative to the adjacent bony structure. In one embodiment, the aperture has, at its intersection with the external surface 1500, a surface area having bone forming material that is at least 5% of that of the surface area of external surface 1500. That is, aperture(s) 15042 may be of greater surface area than 5% of the surface area of external surface 1500 and may contain other device members within them (such as, for example, a fastener or interconnecting member), but the surface area of aperture(s) 15042 at its intersection with surface 1500 that contains bone forming material alone is not less than 5% of the surface area of external surface 1500. In another embodiment, the surface area of the aperture(s) 15042 at its intersection with surface 1500 that contains bone forming material alone is greater than 15% of the surface area of external surface 1500. In yet another embodiment, the surface area of the aperture(s) 15042 at its intersection with surface 1500 that contains bone forming material alone is greater than 25% of the surface area of external surface 1500.

Figure 10:
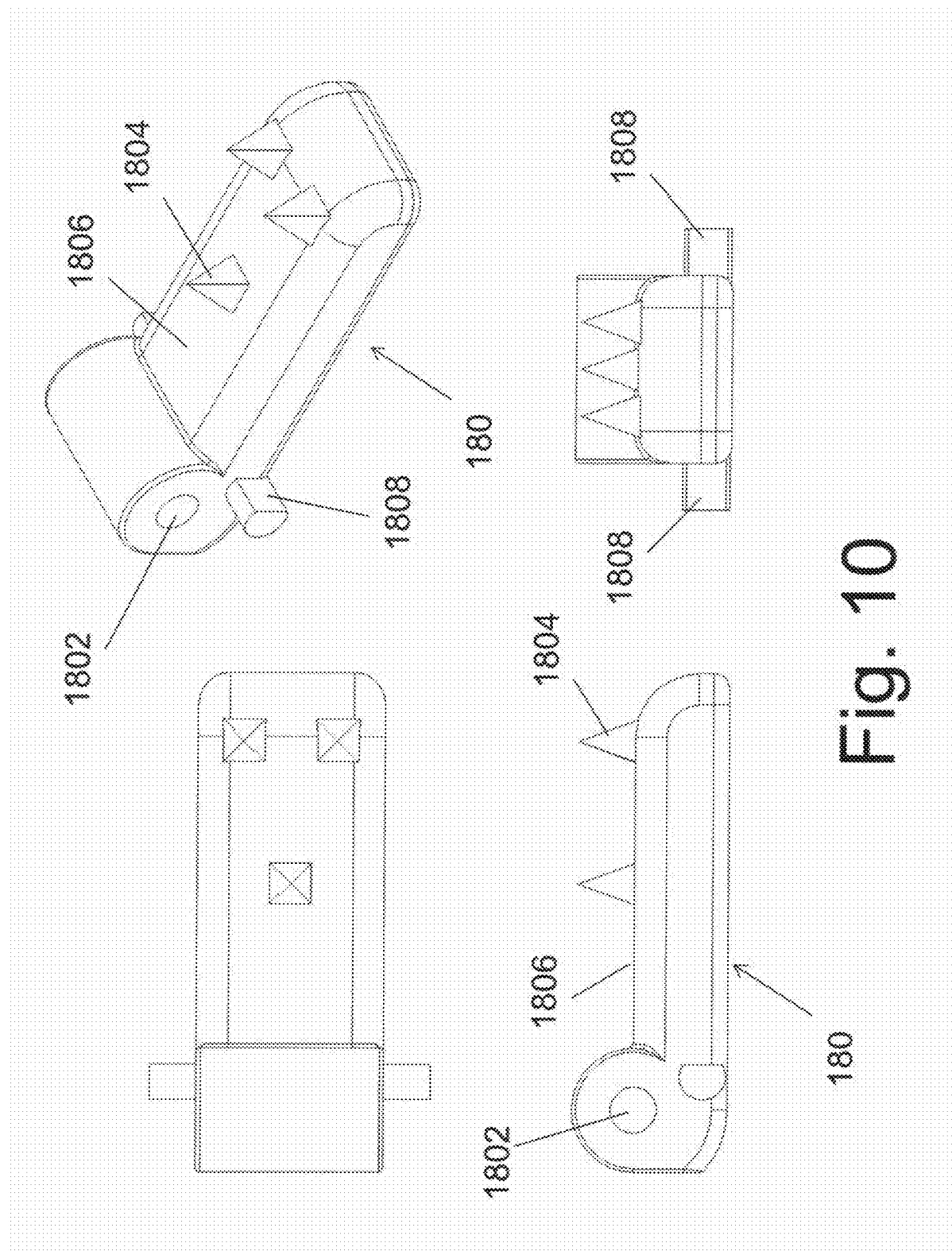
FIG. 10 illustrates side and perspective views of the rotational member of the fixation device of FIG. 1.

Rotational member 180 is shown in FIG. 10. Member 180 contains internal bore 1802 that accepts a pin 202. Projections 1804 extend from bone abutment surface 1806 and contain a sharpened tip that is adapted to penetrate and anchor into bone. Side projections 1808 extend from the side of member 180 and serves to limit the extent of rotation of member 180—as will be discussed below.

Figure 11:
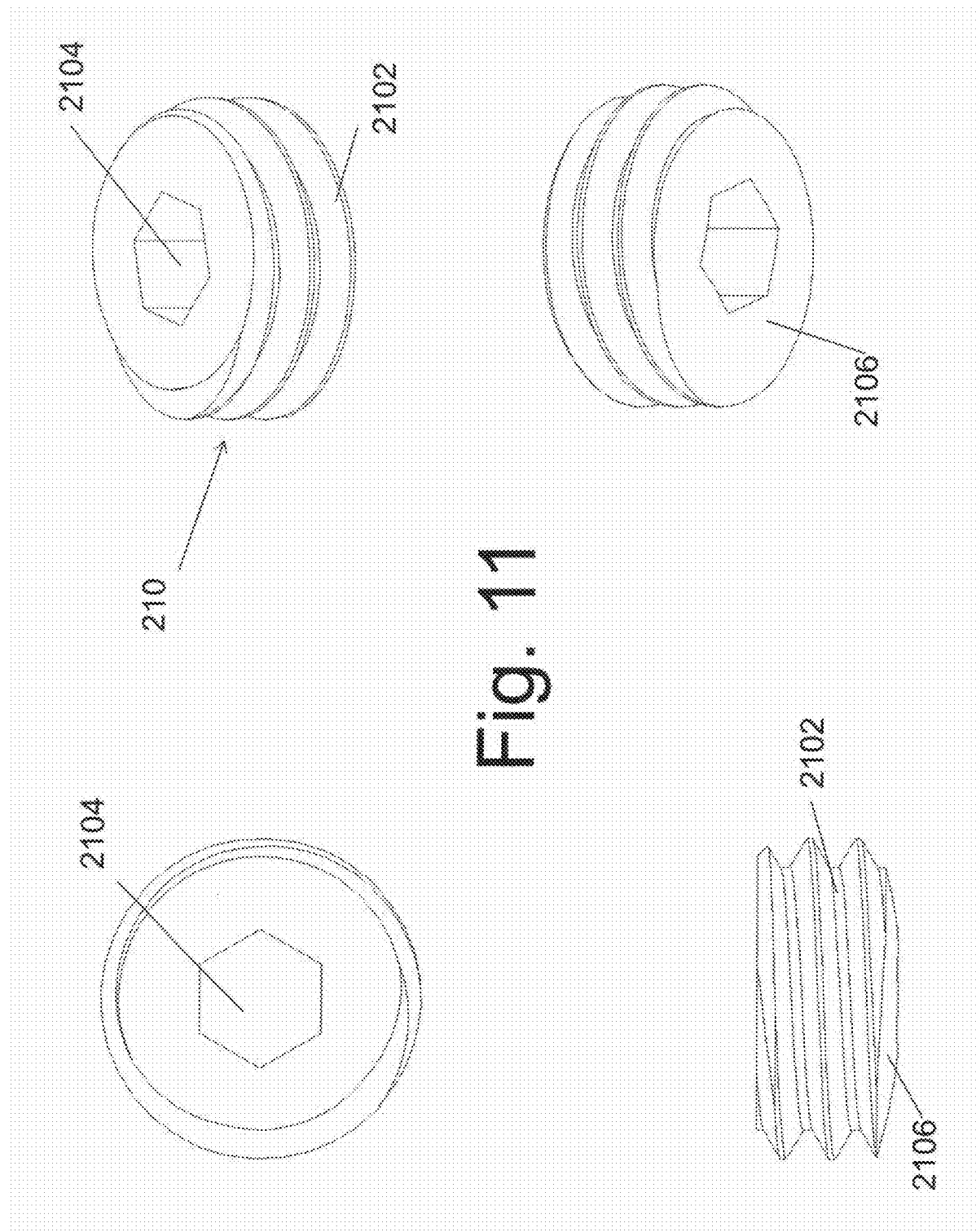
FIG. 11 illustrates side and perspective views of the locking nut of the fixation device of FIG. 1.

Locking nut 210 is shown in FIG. 11. Outer threads 2102 are adapted to interact with complimentary threads 1506 of member 150. An internal indentation 2104 (hex-shaped in the illustration, but may be any applicable geometric shape) receives a complimentary driver (not shown) that can impart a rotational force onto the locking nut. Preferably, but not necessarily, the undersurface 2106 of member 210 is convex (curvilinear) so as to permit movement of member 210 relative to plate member 120—as will be discussed below.

Figure 12:
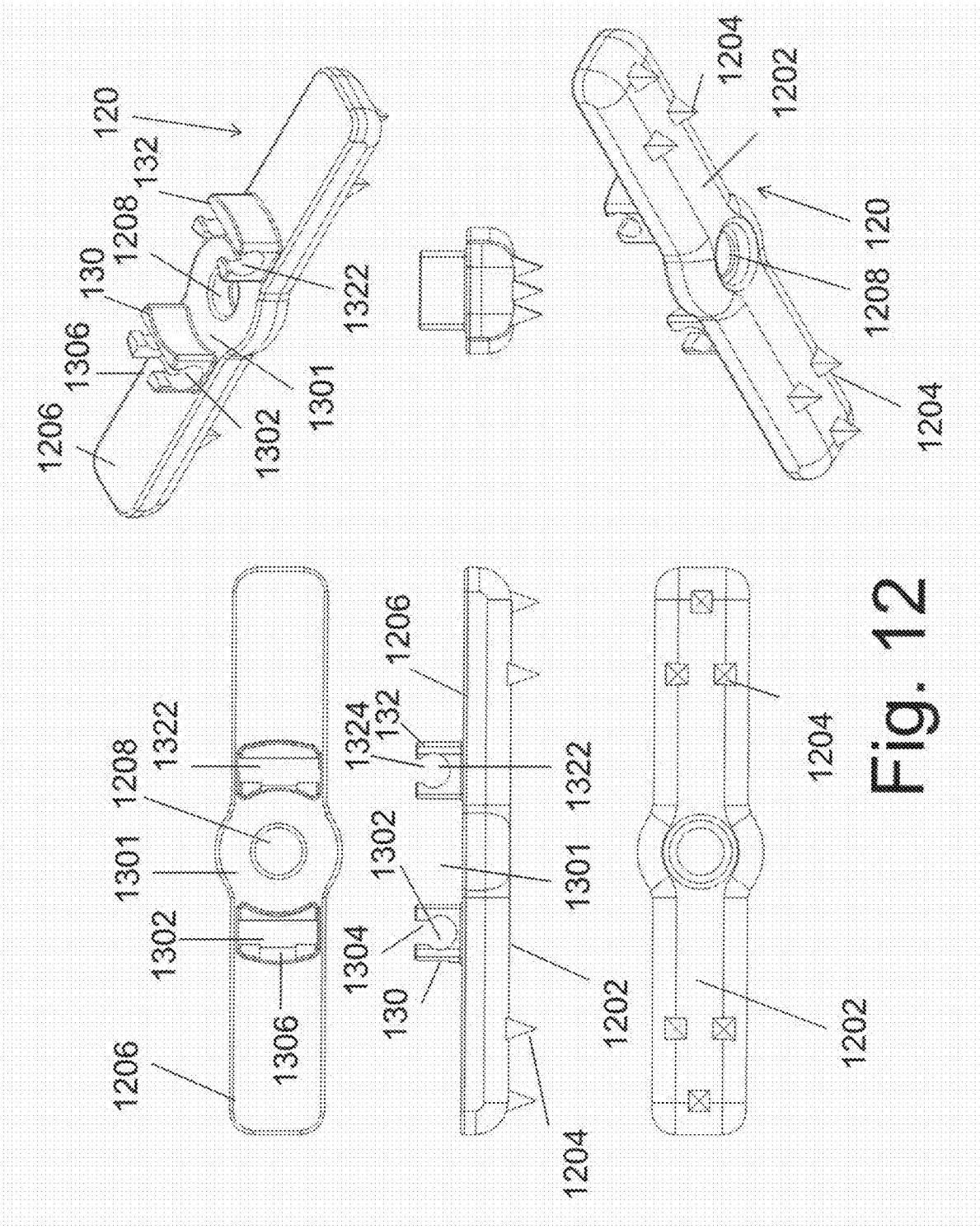
FIG. 12 illustrates side, top, and perspective views of the plate member of the fixation device of FIG. 1.

Bone plate 120 is shown in FIG. 12. The plate substantially has a first bone abutment surface 1202 and opposing second surface 1206. Projections 1204 extend from bone abutment surface 1202. Full thickness bore 1208 extends from surface 1206 to surface 1202. Projections 130 and 132 extend from surface 1206 and serve to attach member 120 to a holding and placement—as will be described below. Projections 130 and 132 define an internal circular space 1301 which will contain locking nut 210. In an embodiment, it will also house Belleville washers (or any other spring-like device or malleable member that functions as a spring).

Projection 130 has circular bore 1302 that extends from one side surface to the opposing side surface of projection 130. A top opening 1304 and side opening 1306 extend into bore 1302. Note that top opening 1304 is of smaller diameter than bore 1302. Projection 132 is similar to 130. It contains an internal bore 1322 with top and side openings. Note that, in a side view, bore 1302 of projection 130 is positioned closer to surface 1206 than bore 1322 of projection 132. This permits accommodation of the holding instrument as will be described below.

Figure 13:
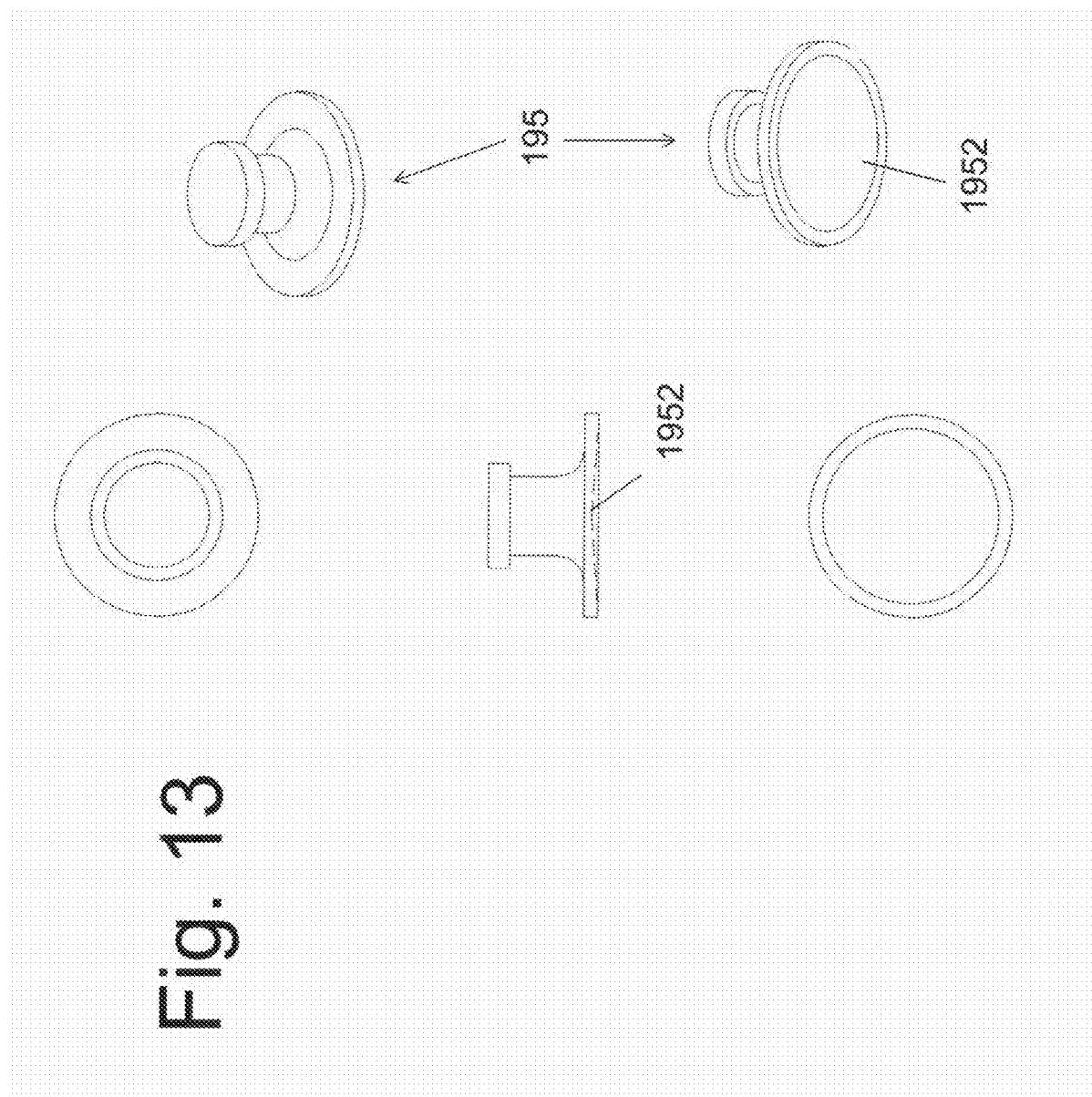
FIG. 13 illustrates side, top, bottom, and perspective views of the retaining member of the fixation device of FIG. 1.
Figure 14:
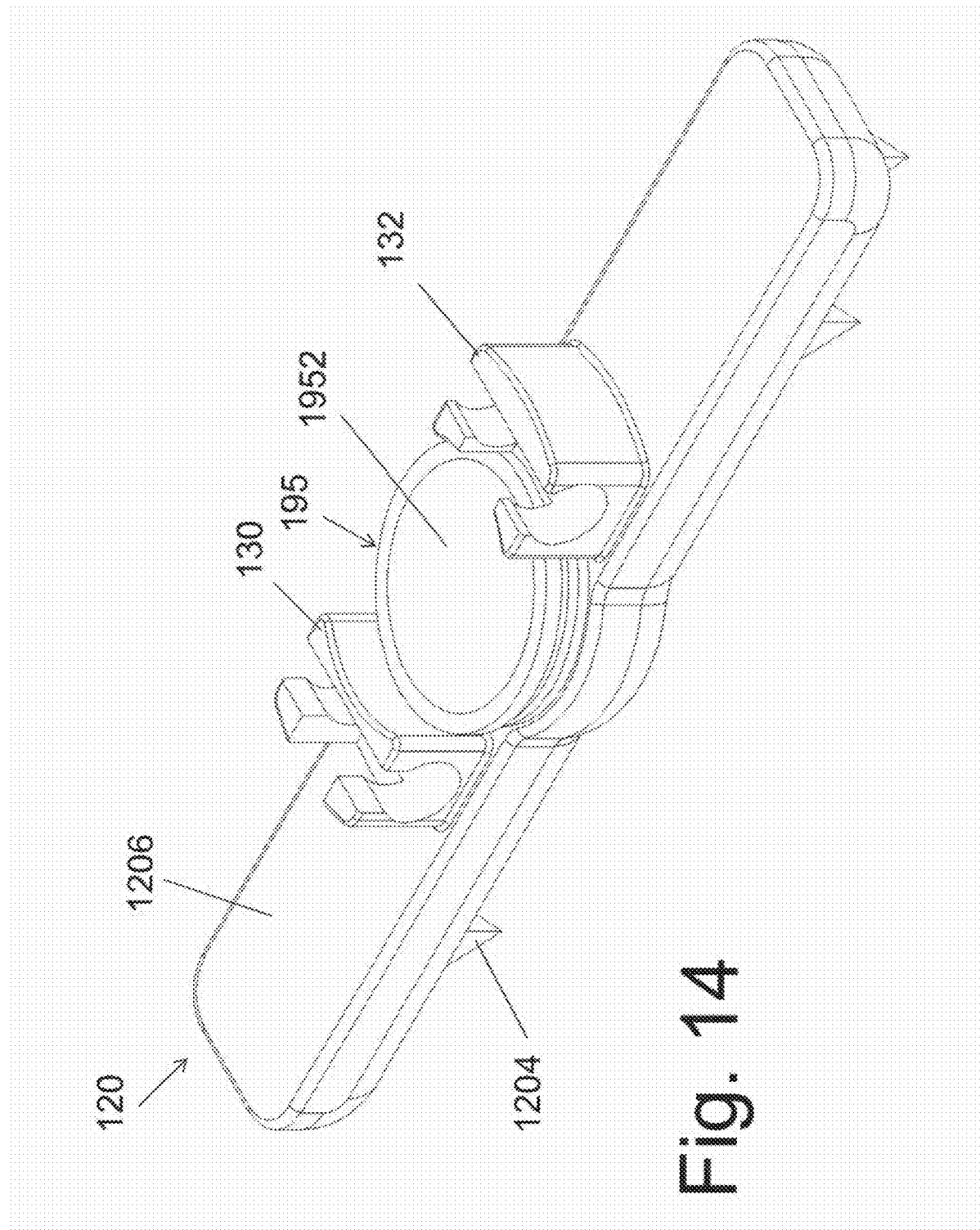
FIG. 14 is a perspective view of an assembly of the exemplary plate member of FIG. 12 and the retaining member of FIG. 13.
Figure 15:
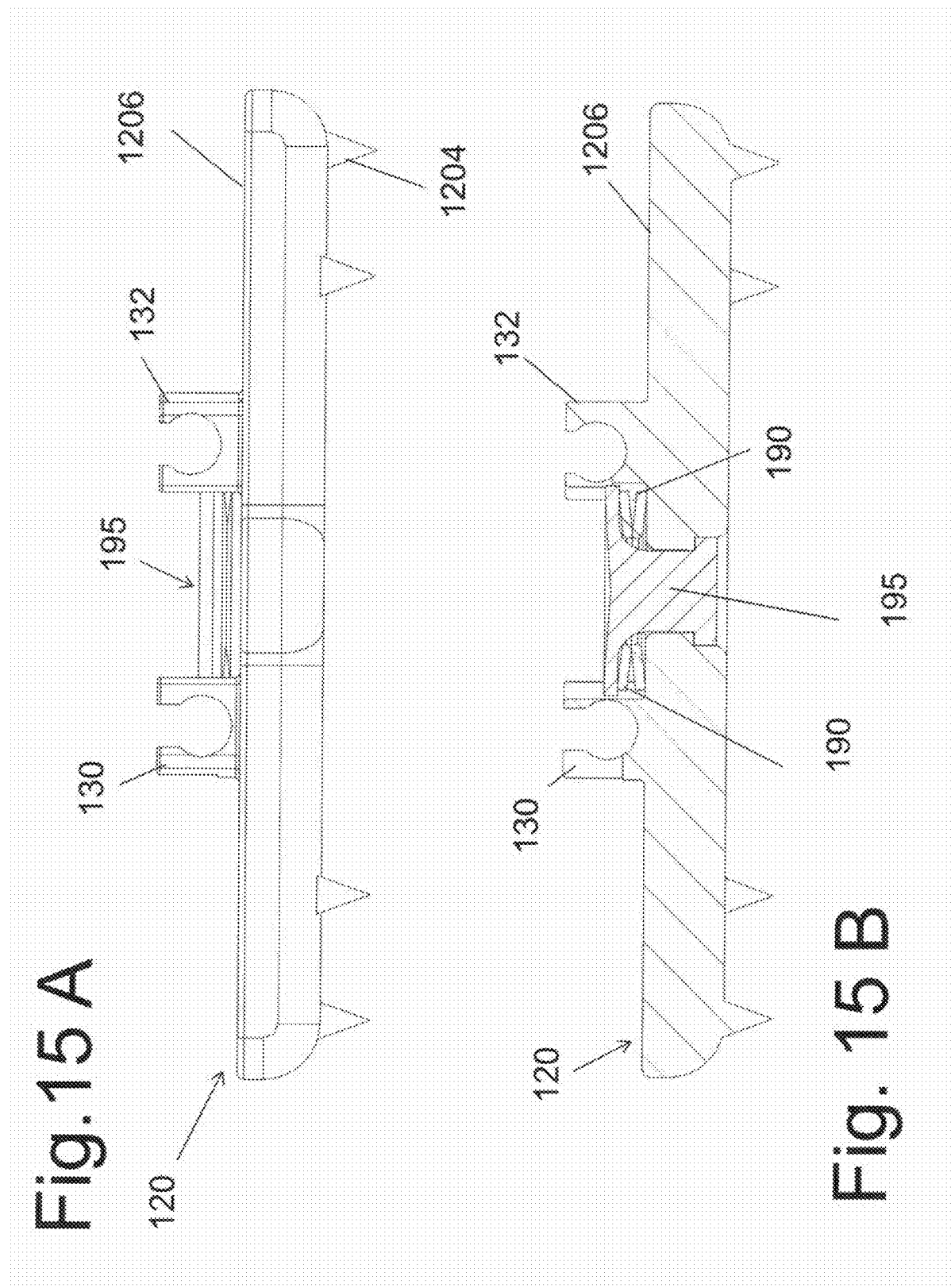
FIG. 15A is a side view of the assembly of FIG. 14.
FIG. 15B is a cross-sectional view of the assembly of FIG. 14.

FIG. 13 illustrates retaining member 195. In an embodiment wherein a spring member (such as, for example, a Belleville washer) is placed within internal circular space 1301 and beneath the locking nut 210, retaining member 195 functions to retain the spring member attached to plate 120. Surface 1952 rests against locking nut 210. The surface is curvilinear (concave) so as to cooperatively abut the curvilinear (convex) inferior surface 2106 of locking nut 210. FIG. 14 illustrates an example of the assembled embodiment with spring member (Belleville washers 190). An exploded view is shown in FIG. 2. Side views of plate with retaining member 195 and Belleville washers is shown in FIG. 15A, whereas a sectional view is shown in FIG. 15B.

Figure 16:
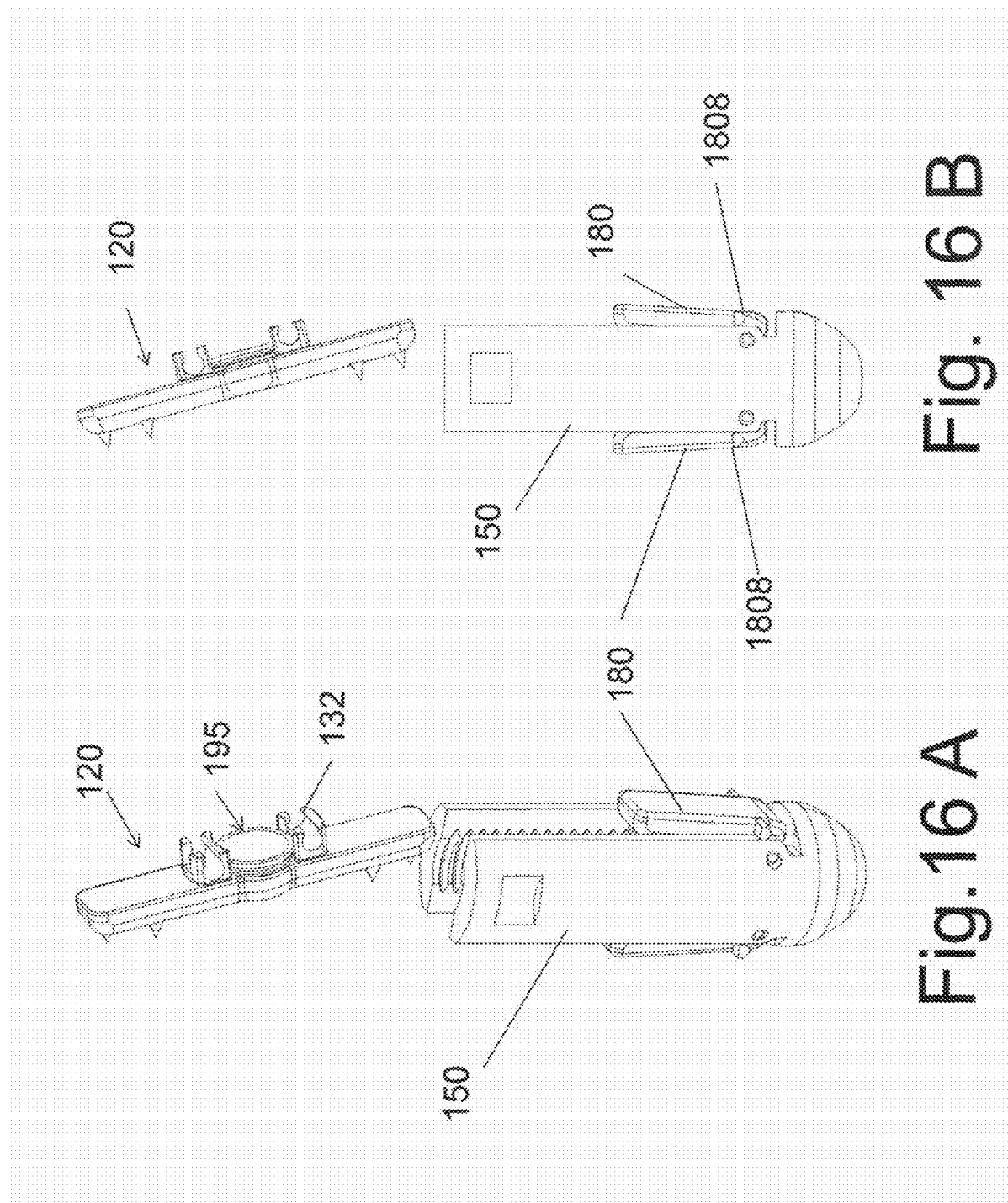
FIGS. 16A and 16B illustrate side and perspective views of the device of FIG. 1 with the plate assembly of FIG. 14 in the "closed" configuration.
Figure 17:
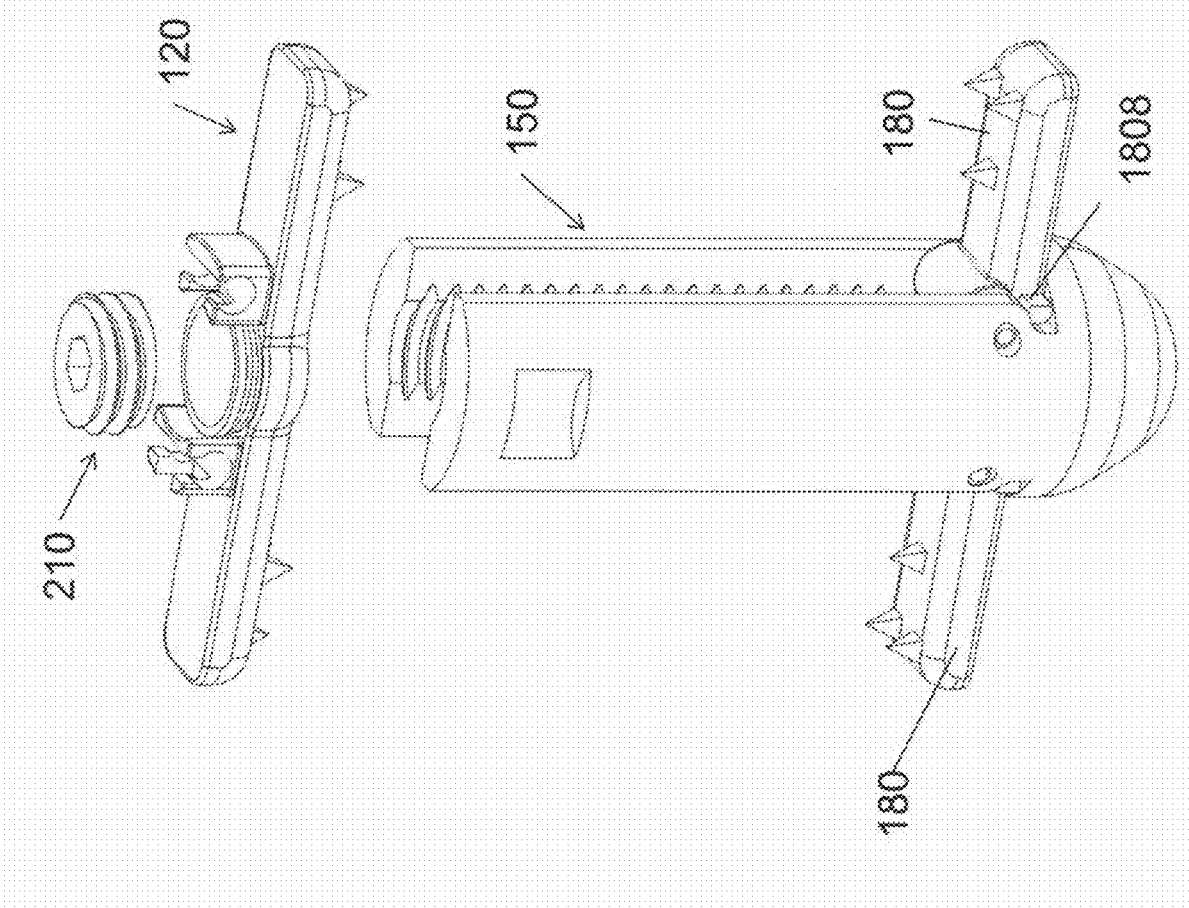
FIG. 17 illustrates a perspective view of the device of FIG. 1 with the plate assembly of FIG. 14 in the "open" configuration.

FIGS. 16A and 16B show the device during implantation with plate 120 and rotational members 180 in the "closed configuration", whereas FIG. 17 shows them in the "open configuration". Note that, during implantation, rotational members 180 are rotated into an "open" positioned so as to be substantially perpendicular to the longitudinal axis of member 150. Note that protrusion 1808 limits the extent of rotation of member 180 and abuts a surface of member 150 when member 180 is fully "closed" (FIGS. 16A and 16B) or fully "open" (FIG. 17). The instrument that actuates and rotates member 180 applies the force needed to produces rotation at protrusion 1808—as well be discussed further below.

Similarly, plate 120 is rotated so as to be substantially perpendicular to the longitudinal axis of member 150. Subsequent advancement of locking nut 210 relative to threads 1506 of member 150 moves the "open" plate 120 towards the open members 180 and forcibly captures the spinous processes of an adjacent first and second vertebral bone therebetween. This will be further illustrated below.

Note that the interaction of the curvilinear surface 2106 of locking nut 206 and the curvilinear surface 1952 of member 195 allow plate member 120 to assume a non-parallel trajectory relative to members 180. This features permits accommodation of the local anatomical variation between adjacent spinous processes. Further, note that the advanced locking nut 210 will place a compressive load on the Belleville washers 190 between it and plate 210. Since repeated movement between the spinous processes that are attached to the plate will cause at least some loosening of fixation protrusions 1804 and 1204 within the surrounding spinous process bone, the Belleville washers function to reload the bone/implant interface and maintain implant fixation. It should be understood that placement of loading springs between the locking nut and plate is not required for implant function, but is contemplated in an embodiment of the present disclosure. When present, the loading springs form an important feature of that embodiment—since they allow the implant to be self-tightening.

Figure 18:
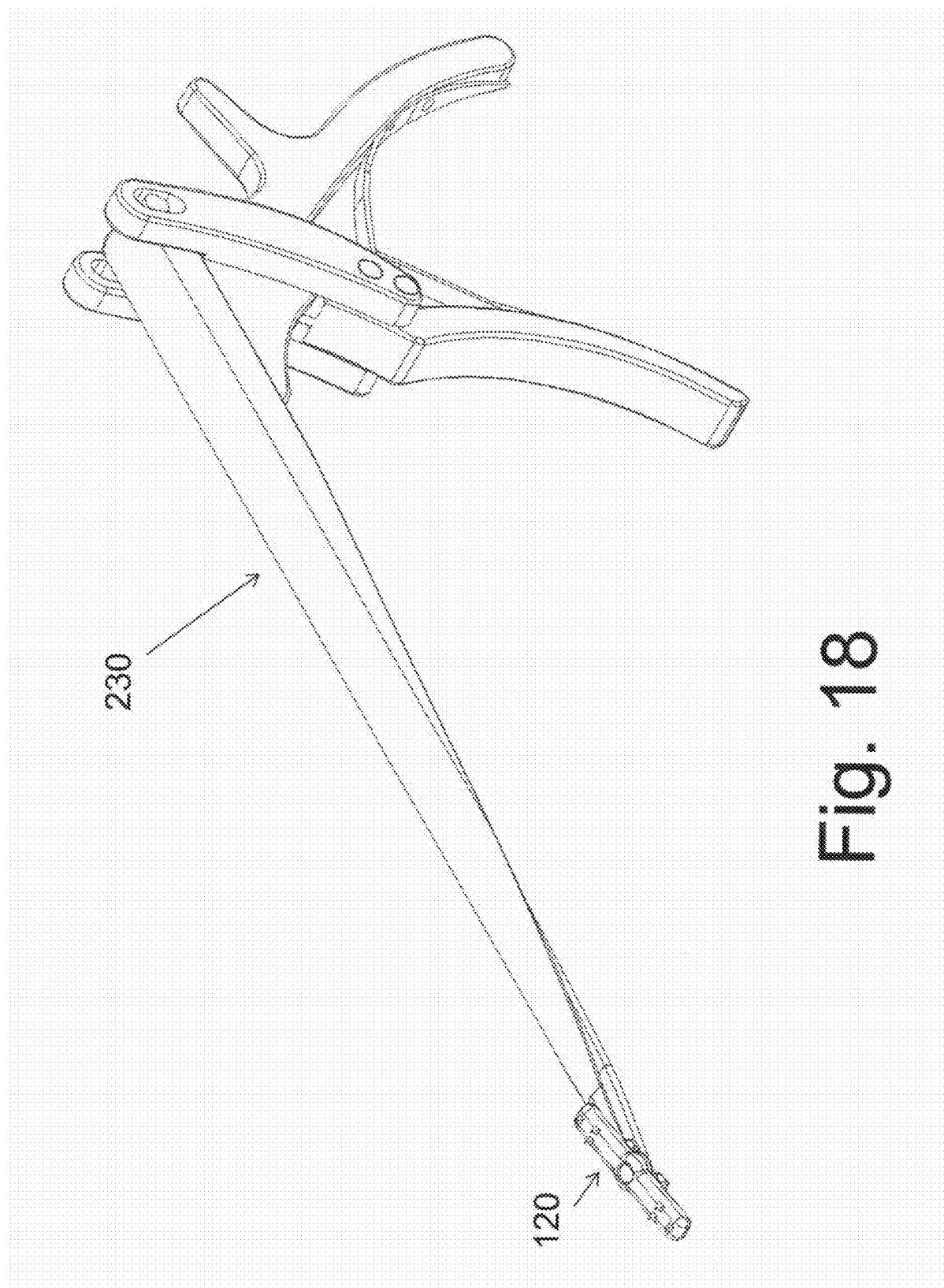
FIG. 18 is a perspective view of an exemplary instrument for reversibly rotating the plate assembly of FIG. 14 from the "open" to the "closed" configuration within the exemplary implant of FIG. 1.
Figure 19:
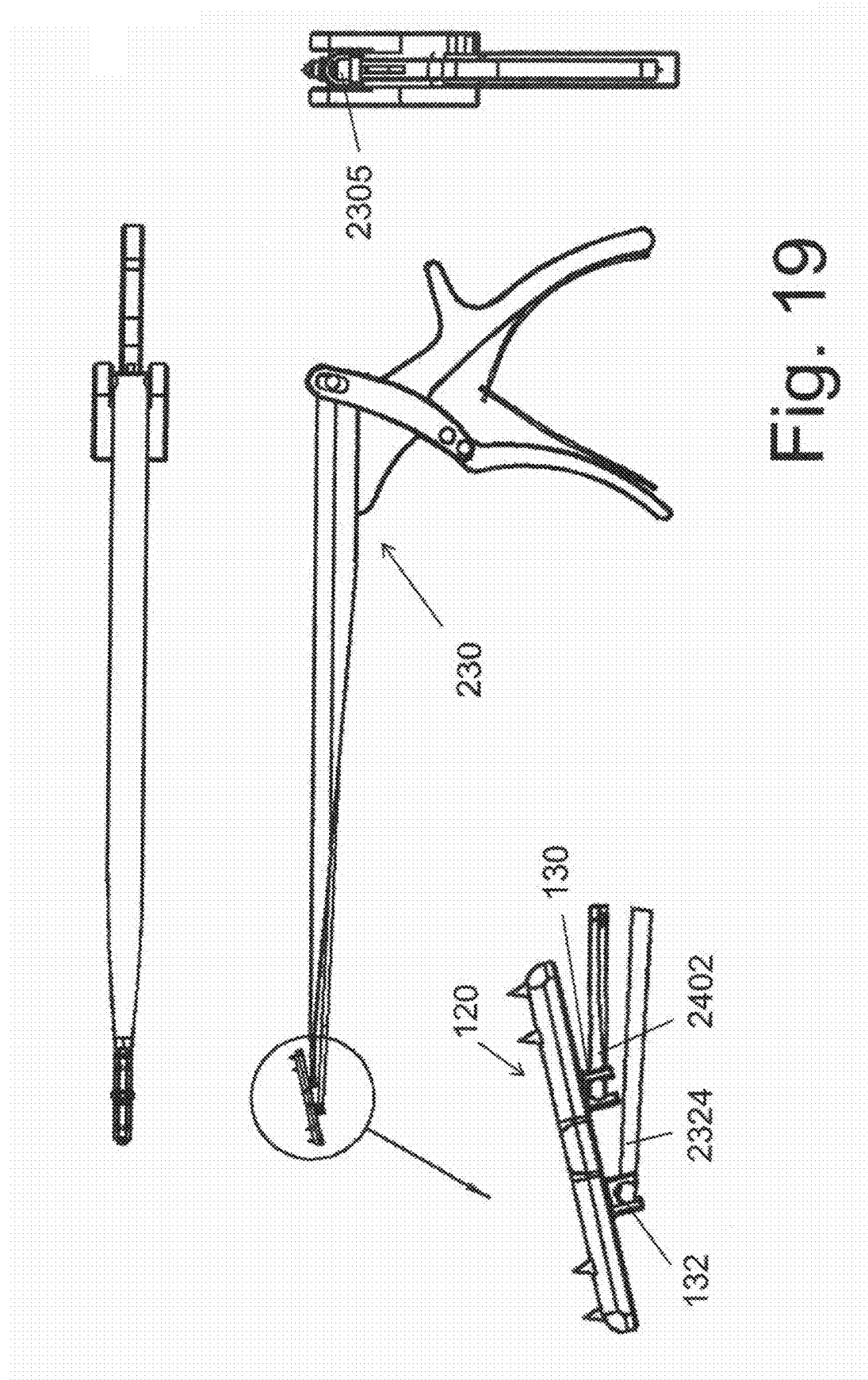
FIG. 19 is an orthogonal view of the exemplary instrument of FIG. 18.
Figure 20:
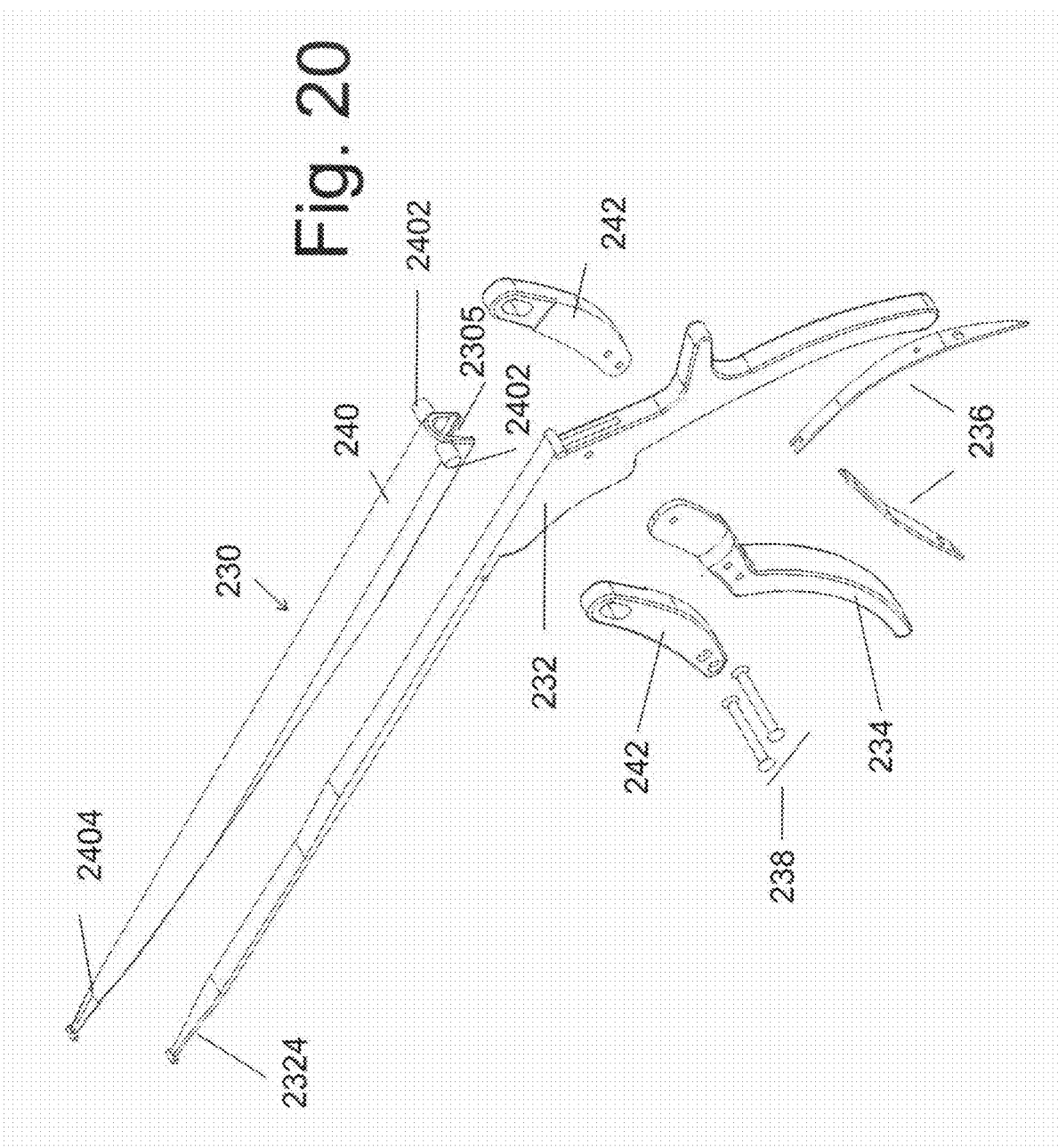
FIG. 20 is an exploded view of the exemplary instrument of FIG. 18.

Plate member 120 is actuated to reversibly rotate from the fully "closed" to the fully "open" position by the use of instrument 230. Instrument 230 is illustrative and it should be appreciated that any other instrument adapted to rotate member 120 may be alternatively used. The instrument 230 is a hand actuated device but may be alternatively configured to be mechanically drive, such as, for example by an attached drill. (See, for example, U.S. patent application Ser. No. 11/559,871, which is hereby incorporated by reference in its entirety.) Instrument 230 is shown in a perspective view in FIG. 18. FIG. 19 illustrates orthogonal views while FIG. 20 shows an exploded view. Instrument 230 is comprised of a grip 232, an articulating hand member 234, spring members 236 and rivets 238. Side connectors 242 connect the grip 232 to actuating member 240. Protrusions 2402 of member 240 attach to side connectors 242. Various pins may be used to hold different members together and are not necessarily shown in the exploded view.

Figure 23:
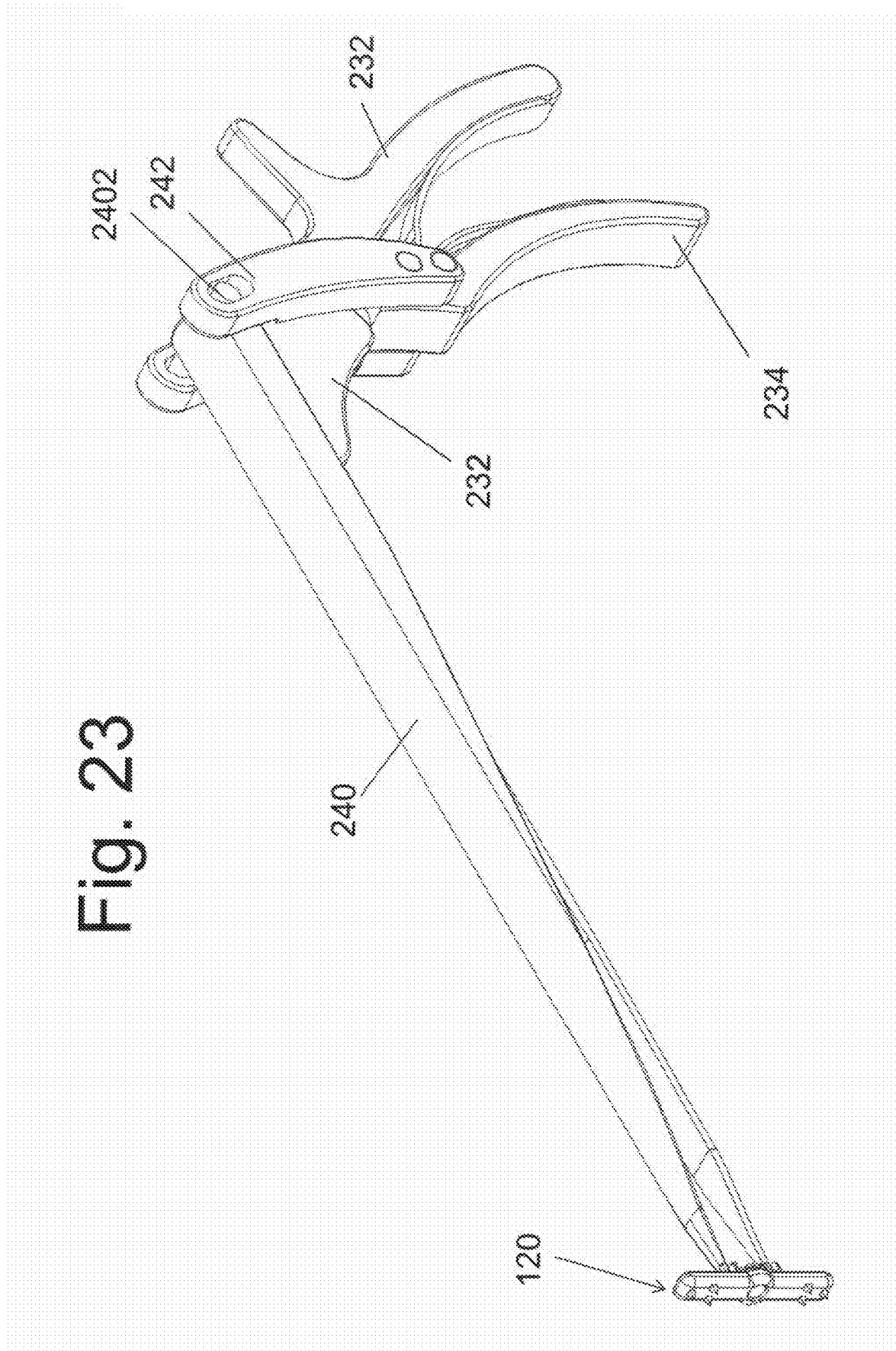
FIG. 23 is a perspective view of the actuated exemplary instrument of FIG. 18 with the rotated exemplary assembly of FIG. 14.
Figure 24:
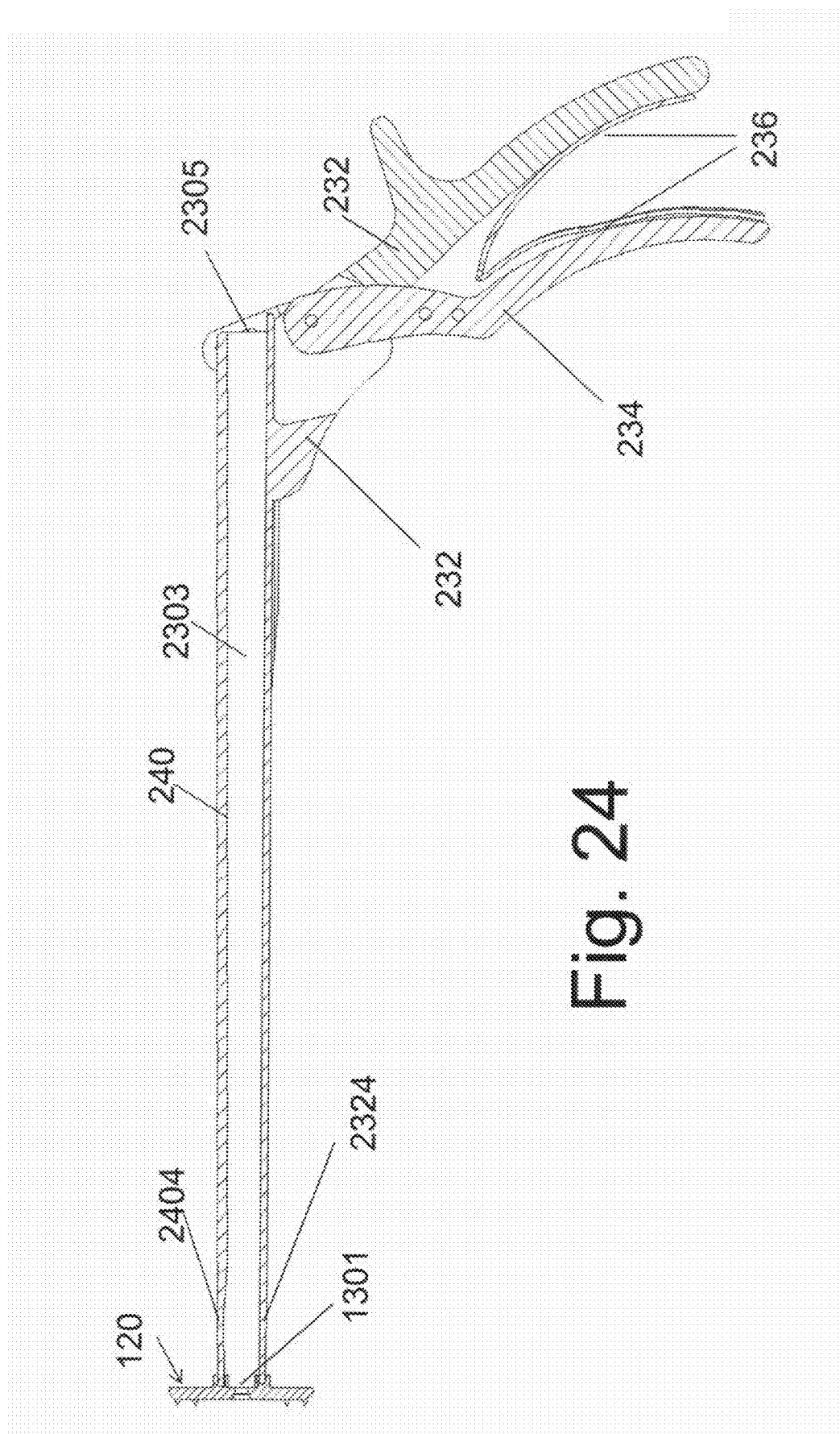
FIG. 24 is a cross-sectional view of the actuated exemplary instrument of FIG. 18 with the rotated exemplary assembly of FIG. 14.

Actuating member 240 has a "T" shaped distal end 2404 that is adapted to interact with segment 130 of plate 120. Grip 232 has a separate "T" shaped distal end 2324 that is adapted to interact with segment 132 of plate 120 (see FIG. 19). Squeezing grip 232 produces the translation of end 2402 relative to end 2324 and the rotation of member 120—as is shown in FIG. 25. A perspective view of the actuated instrument 230 with rotated plate member 120 is shown in FIG. 23 and a section view is shown in FIG. 24. Note that the actuated instrument 230 contains channel 2303 (FIG. 24) that extends from end opening 2305 (also, see FIGS. 19 and 20) to the internal circular space 1301 of plate member 120 (FIG. 12). Channel 2303 permits the passage of locking nut 210 (attached to a screw driver) into space 1301 (posterior to retaining member 195) after plate member 120 has been rotated into the "open" configuration.

Figure 21:
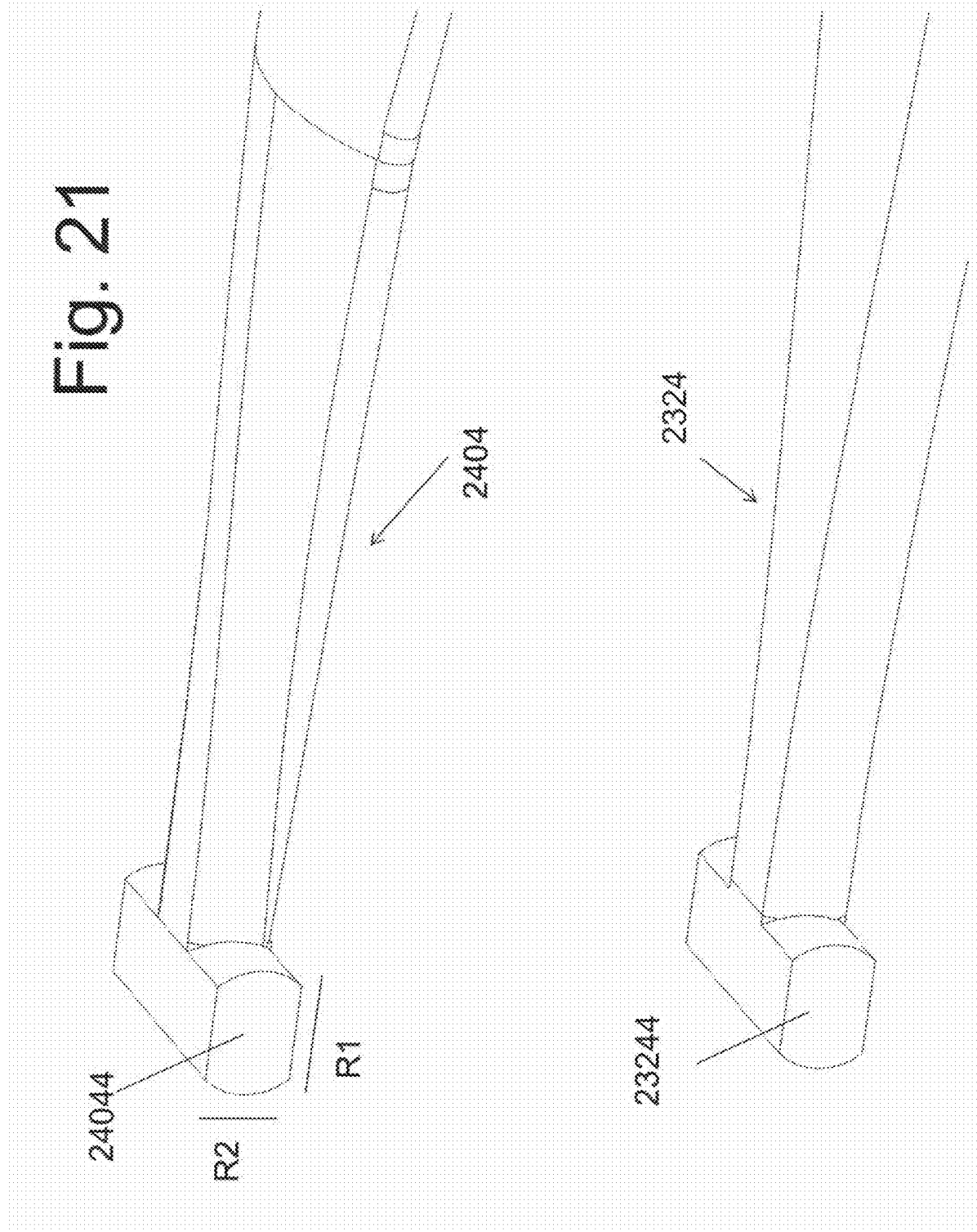
FIG. 21 is a close-up view of the end segments of the exemplary instrument of FIG. 18.
Figure 22:
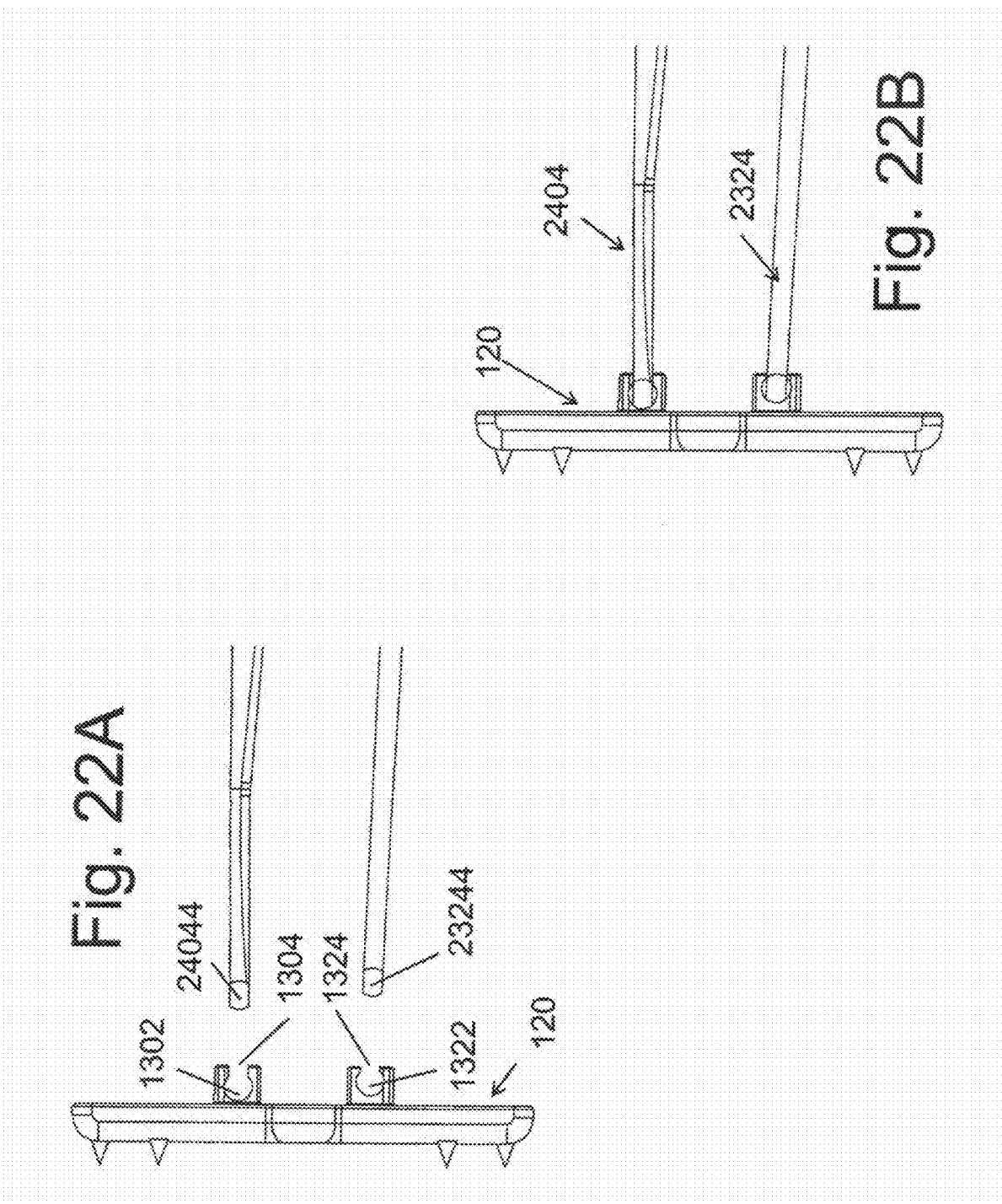
FIGS. 22A and 22B illustrate side views of the interaction of the exemplary instrument of FIG. 18 with an exemplary plate member of the assembly of FIG. 14.

FIG. 21 illustrates end segments 2402 and 2324. FIG. 22 show the end segments interacting with plate 120. Segment 2404 has bar 24044 that extends substantially perpendicular to the long axis of member 240. Bar 24044 has radius R1 that is slightly smaller than the radius of bore 1302 of member 130 of plate 120 but greater than the size of top opening 1304. Thickness R2 is slightly smaller than the size of top opening 1304. Segment 2324 has bar 23244 having similar size relationship with bore 1322 of member 132 of plate 120. In this way, when the plate 120 is rotated into the "open" configuration of FIG. 22 (wherein the long axis of plate 120 is substantially perpendicular to the long axis of segments 2402 and 2324-FIG. 23), bar 24044 can enter and exit bore 1302 freely through top opening 1304. Similarly, bar 23244 can enter and exit bore 1322 freely through top opening 1324. However, when plate 120 is in the "closed" configuration (wherein the long axis of plate 120 is substantially oblique to the long axis of segments 2402 and 2324—FIG. 18), bar 24044 is retained in bore 1302 and bar 2344 is retained within bore 1322 so that the plate 120 cannot be detached from instrument 230.

Deployment Tubes

Illustrated are instruments used to position implant 105 at the target interspinous space. FIG. 26A shows an exploded view of an outer member 302. Member 302 is an elongated tube that extends from a proximal end 3023 to a distal end 3027 and has an internal bore 3022. Distal protrusions 304 and 306 are positioned at the distal end whereas extension 308 is positioned at the proximal end. Full-thickness side cut 3024 and 3026 extend from the outer surface of member 302 to internal bore 3022 and contain side doors 314 and 316, respectively. Each door is attached onto outer member 302 with a pin 310. The assembled member 302 is shown in FIG. 26B with side doors 314 and 316 in the closed position. Each side door member 314 and 316 is adapted to open outwardly in reaction to an outward-directed force from within internal bore 3022. Each door may be spring loaded (spring(s) not shown) and biased toward the closed position of FIG. 26B. The assembled member 302 is shown in FIG. 26C with side doors 314 and 316 in the open position.

A cross-sectional view of member 302 is shown in FIG. 27A. Doors 314 and 316 are positioned in the open position. Internal bore 3022 contains an indentation 3021 that extends from ledge 3029 to cut-out 3025. FIG. 27B better illustrates distal protrusions 304 and 306. These protrusions are adapted to at least partially encircle the outer surface of member 150—when it is coupled to member 302. Ends 3042 and 3062 are each configured to engage and advance protrusion 1808 of member 180—so as to rotate each member 180 into the "open" position (FIG. 17).

FIG. 28B shows an oblique and section view of inner member 350. FIG. 29A shows orthogonal views of member 350, whereas FIG. 29B illustrates a section view through the device. Member 350 extends from top surface 3504 to distal end 3507 and has internal bore 352 that is configured and sized to permit the advancement of plate 120 therethrough when it is in the closed configuration and attached to placement instrument 230 (as shown FIGS. 18 & 19). The outer surface of member 350 has threads 358 and side openings 354 and 356. Side openings cuts 354 and 356 extend from the outer surface of member 350 to internal bore 352. The proximal aspect of member 350 has a "T" handle 360. The proximal aspect of member 350 is shown in an enlarged view in FIG. 28A. Top surface 3504 contains bores 3505 that are adapted to accept a locking member. Each bore 3505 is internally contained within the segment of member 350 that extends from top surface 3504 to the distal aspect of threads 358. However, each bore 3505 is partially open distal to the distal aspect of threads 358—see FIGS. 28A and 29B.

Each locking member 370 is adapted to be at least partially contained within each bore 3505. As can be seen in FIG. 30, locking member 370 contains an elongated member having a cylindrical body 372 that extends from a proximal end 3702 to a distal end. The distal end contains protrusion 374 which is sized and configured to fit within recess 204 of member 150. The interaction of the protrusion 374 and recess 204 will be discussed further in the following sections.

FIG. 30 illustrates each locking member 370 being positioned within each bore 3505. After advancement of member 370 through bore 3505, proximal end 3702 projects above top surface 3504 of member 350 as seen in FIG. 31. A Gear member 382 is attached onto proximal end 3702 and affixed using any known method for component fixation (such as, for example, brazing, adhesives, press fit, thermal techniques and the like). Member 390 is positioned onto top surface 3504, wherein member 390 has internal serrations that interact with each of gears 382 in a planetary gear-like arrangement. Member 390 is retained onto member 350 by pins 3902—which are retained within cut out 3904 of member 390 and function to also limit the extend of rotation of member 390. The assembled device is shown in FIG. 32. Note that the protrusion 374 of each member 370 extends inwards and towards internal bore 352 of member 350 when member 390 is in the illustrated position. (In contradistinction, protrusion 374 of each member 370 extends outward and away from internal bore 352 of member 350 when member 390 is in the position shown in FIG. 35.)

With protrusion 374 of each member 370 extending towards internal bore 352 of member 350, outer member 302 can be coupled with inner member 350 as shown in FIG. 33. Nut 402 has a knurled external surface and a central bore. The central bore has threads 4022 that are adapted to cooperatively engage threads 358 of member 350. When member 350 and 302 are coupled, rotation of nut 402 relative to threads 358 in a first direction will cause member 302 to travel along member 305 in a first longitudinal direction. Conversely, rotation of nut 402 relative to threads 358 in an opposite direction will cause member 302 to travel along member 305 in an opposite longitudinal direction. Note that cylindrical body 372 of locking member 370 is at least partially contained within indentation 3021 of member 302 and protrusion 374 is configured to fit within cut-out 3025 of member 302 (see FIG. 36).

FIGS. 34-37 illustrate the assembled outer member 302 and inner member 350. FIG. 37 shows sectional views. In FIGS. 34 and 36B, member 390 is rotated into a "locked" position, wherein protrusion 374 of each member 370 extends inwards and towards internal bore 352 of member 350. In FIGS. 35 and 36A, member 390 is rotated into an "unlocked" position, wherein protrusion 374 of each member 370 extends outward and away from internal bore 352 of member 350. Note that member 390 must be in the "unlocked" position in order to couple implant 105 to the assembly. Further, when member 390 is in the "unlocked" position, outer member 302 and member 350 are locked together and prevented from movement relative to one another along the longitudinal direction.

Method of Device Placement

The implantation of the fixation devices will now be described. As mentioned above, the devices perform a spacing function as well as the compression and fixation of adjacent spinous processes such that the spinous processes of the implanted vertebral bones are locked in position relative to one another. That is, the device enlarges the target interspinous space by increasing the distance from the inferior surface of the superior spinous process to the superior surface of the inferior spinous process, wherein the superior and inferior spinous processes are the spinous processes that border and define the target interspinous space.

It should be appreciated that the fixation device described herein may be used with any surgical approach to the posterior aspect of the spine and the disclosed fixation device can be positioned in the spine using any appropriate surgical method and/or surgical corridor. The fixation device described herein is particularly adapted to be placed through a lateral surgical approach to the spine that starts with a surgical incision in the posterior aspect of the patient's flank (i.e., side aspect of the abdominal cavity). The fixation device described herein is also particularly adapted for use in stabilizing the posterior aspect of a spinal segment when a second orthopedic implant is implanted into the disc space of that segment using a lateral, or flank, approach to the disc space. It must be noted that while the lateral approach is employed in one method of use, the implantation procedure of the device is by no means limited to a lateral approach to the interspinous space.

Figure 5:
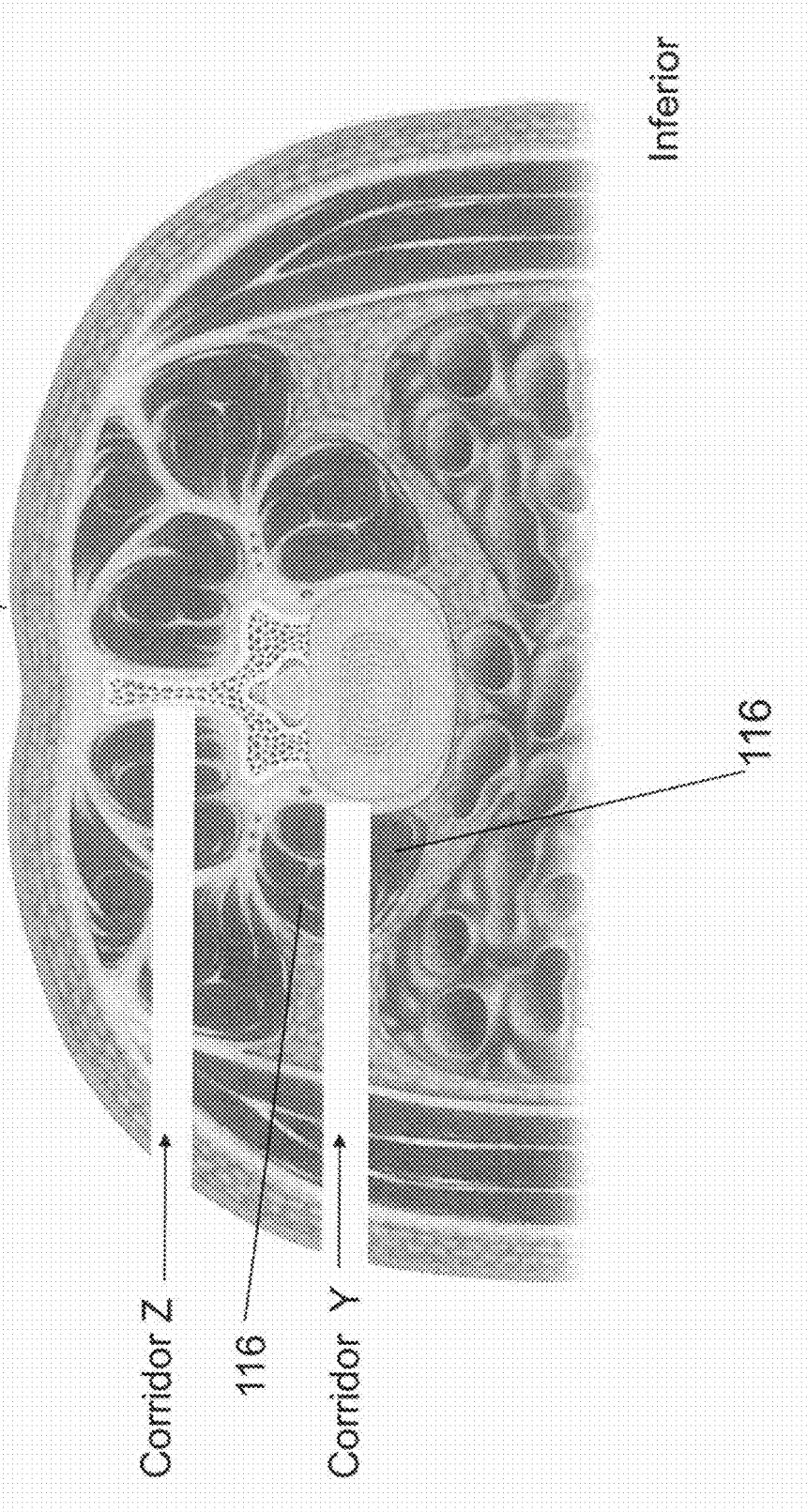
FIG. 5 is a cross sectional view of the torso at the level of the lumbar spine for use with the common flank approach.

In an embodiment, the fixation devices are implanted into the lumbar spine using a flank incision and a lateral approach—which is now described. The spinal level of desired device implantation can be localized under imaging guidance (such as, for example, using X-rays). Referring to FIG. 5, a skin incision can be placed in the flank at the approximate cephalad-caudal level of the implantation site on the spine. FIG. 5 illustrates a cross sectional view of the torso at the level of the lumbar spine. For clarity of illustration, the contents are represented schematically and those skilled in the art will appreciate that an actual cross section of the human torso may include anatomical details not shown in FIG. 5.

Figure 6:
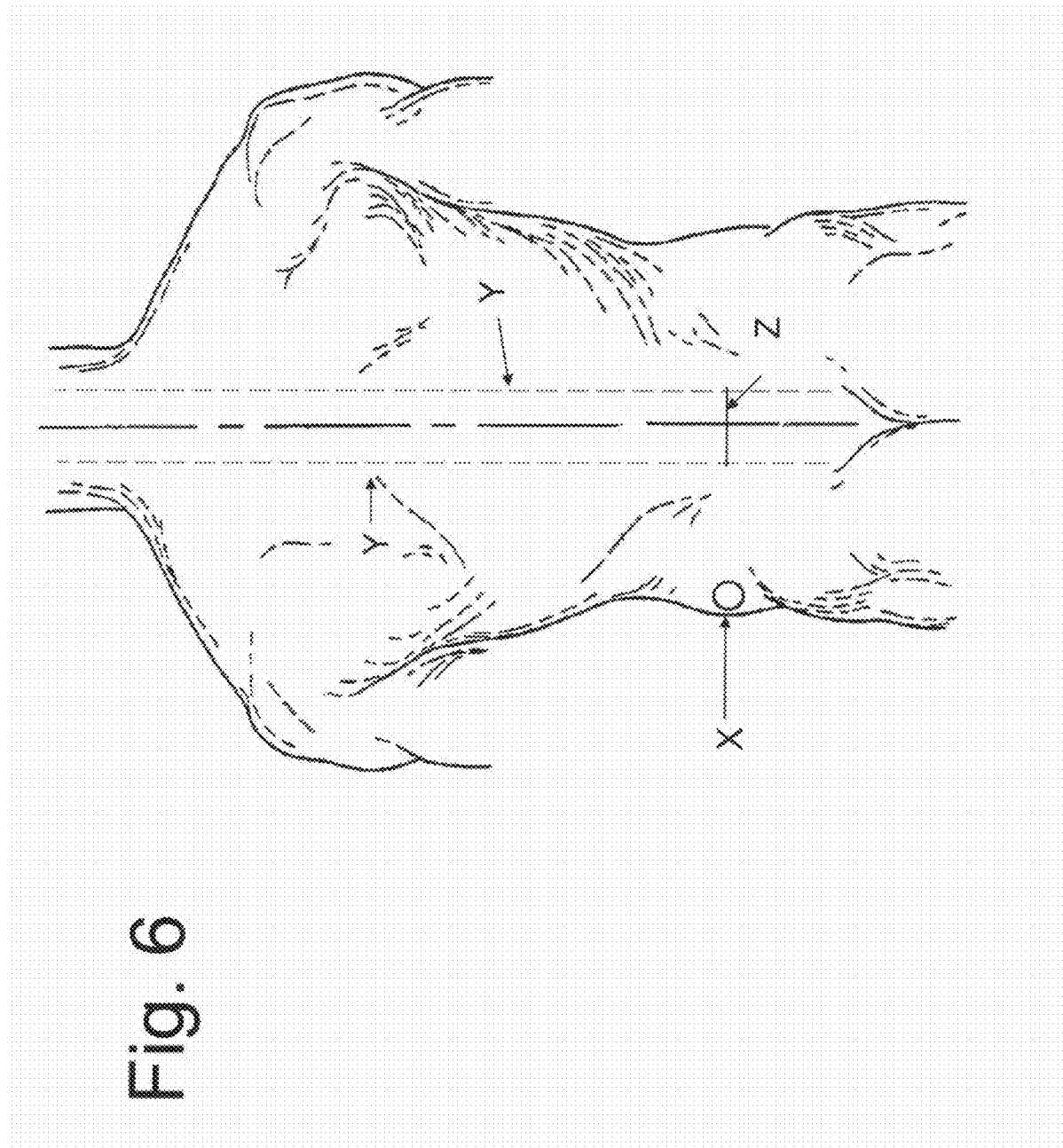
FIG. 6 is a schematic representation of the posterior aspect of a patient illustrating an XLIF incision location.

In preparation for percutaneous placement of the implant into a spinal level, the patient can be, but is not necessarily, placed in a prone or lateral decubitus position. The level of the spine that is to be implanted can be localized on X-ray in at least one plane. After the customary sterile preparation of the operative site, the surgeon can localize an incision point on the skin that is substantially directly lateral to the spinal segment that will be implanted. FIG. 6 shows a schematic representation of the posterior aspect of a patient. The skin overlying the back is shown. Lines Y show the lateral extent of the fact joints of the spinal column. Assuming that the spinal level to be accessed is at line Z, the surgeon can make an incision at or about circle X.

A lateral corridor "Y" (FIG. 5) can be made from the flank, through the psoas muscle 116 and onto the lateral aspect of the disc space at the spinal level to be implanted. An implant can be placed through the corridor Y and into disc space or onto the spine. The procedure is known to those skilled in the art and known as the "XLIF" procedure. (Once again, see "Extreme Lateral Interbody Fusion (XLIF): a novel surgical technique for anterior lumbar interbody fusion" by Ozgur, Aryan et al. in *Spine J.* 2006 July-August; 6(4):435-43, which is hereby incorporated by reference in its entirety.)

A second lateral corridor "Z" (FIG. 5) can be made from the flank, through the posterior tissues lateral to the spine and onto the lateral aspect of the spinous processes and interspinous ligament of the level to be implanted. While Corridor Y and Corridor Z are shown schematically as exiting the skin of the flank at two different sites, both corridors can be made through a single, common skin incision on the patient's flank. Once through the skin, the trajectory can be then varied so as to form an anatomically anterior Corridor Y and an anatomically posterior Corridor Z. The device disclosed herein can be implanted into the posterior aspect of a functional spinal unit using a Corridor Z and, at the same operation, an implant can be placed into or onto the anterior column (including disc space) of the same functional spinal unit using a Corridor Y.

The totality of the operation—from selection of the target level to implant to the final placement of implant—can be performed under image guidance. Further, the operation can be performed using percutaneous or minimally invasive surgical techniques with or without the aid of electrophysiological monitoring. The later include techniques such as electromyography (EMG) and are intended to alert the operating surgeon to the presence of nerves and other neural elements within the surgical corridor. EMG identification of nerves permits the surgeon to navigate the surgical site with increased safety and to lessen the possibility of nerve injury.

After placement of lateral/flank skin incision (at or about "X" of FIG. 6), cylindrical tissue dilator are advanced through the incision and used to create a corridor (such as, for example, corridor z of FIG. 5) to the interspinous space of the target segment. The tract is sequentially dilated to the desired size. The technique of expanding a tissue corridor by the sequential placement of progressively larger tubes is known in the art, and was also disclosed by Abdou in U.S. patent application Ser. No. 12/940,960 (which is hereby incorporated by reference in its entirety). After tract dilatation, the outer-most tube (or expandable tissue dilator, as shown in U.S. patent application Ser. No. 12/940,960) is retained whereas all the smaller-sized dilation tubes are removed. The internal aspect of the retained tube forms a corridor to the lateral aspect to the target interspinous space.

The target space is accessed and the interspinous ligament contained therein is cut and/or perforated. At least a segment of each of the two spinous processes that border the target interspinous space is decorticated (wherein the decorticated segments also form a border of the target interspinous space). The decortication step prepares the bone of each spinous process for the formation of a fusion mass with the spinous process. (For clarity of illustration, the vertebral bones are not illustrated in the accompanying drawings.)

The internal aspect of housing member 150 is filled with bone forming material. The bone forming material is placed to substantially fill the internal bore 1504 of member 150. With rotation members 180 in the "closed" position, the device is attached to the tube assembly of outer member 302 and member 350—as shown in FIGS. 38 and 39. Note that member 390 must be in the unlocked position in order to attach member 150 (FIG. 38). After member 150 is placed inside of the space between protrusions 304 and 306, member 390 is rotated to the "closed" position which rotates the protrusion 374 of each member 370 into a recess 204 of member 150 (FIG. 39). It should be noted that when member 150 is rigidly attached to the tube assembly, member 150 is positioned with end 1501 abutting distal end 3507 of member 350. Further, ends 3062 of protrusion 306 and ends 3042 of protrusion 304 are abutting projections 1808 of rotational members 180. Note that the engagement between the ends 3062 of protrusion 306 and the ends 3042 of protrusion 304 with the projections 1808 of the rotational members 180 are located on the external surface of member 150. That is, the engagement between the impartment placement device and the rotational members 180 in one embodiment comprises an abutment of the external surface (1500 and 1503) of member 150, and is not within the internal aspect of member 150. This feature permits maximization of the internal space for placement of the bone forming material.

In this embodiment, the direct external engagement between member 302 of the tube assembly and the rotational members 180 forcibly rotates members 180 at the time of implantation (as will be discussed below). In one variant, member(s) 180 is not rotated through a direct internal engagement mechanism between a segment of the implant placement devices (of the tube assembly) and the rotational members, nor through the use of a linkage that is wholly contained within the internal aspect of member 150.

The tube assembly and the attached implant are then advanced to the target interspinous space (through the cylindrical tube that forms corridor Z). "T" handle 360 permits the surgeon to control the implantation process. The distal end of the implant is advanced across the target interspinous space until the free end of each rotation member 180 is positioned on the contralateral side of the spinous processes that border the target interspinous space. (Note that the ipsilateral side of the spinous processes is on the same side of the sagittal midline of the subject as the site of the skin incision of device insertion. Conversely, the contralateral side of the spinous processes is on the opposite side of the sagittal midline of the subject as the site of the skin incision.) At the time of advancement across the target interspinous space, members 180 are purposely angled relative to member 150 so as to form an arrow-like configuration. In this way, the free end of each member 180 would be captured on the contralateral side of the spinous process and unable to return across the interspinous space.

After members 180 are positioned on the contralateral side of the spinous processes, knurled nut 402 is rotated. As member 302 is advanced relative to member 350, distal protrusions 304 and 306 of member 302 forcibly rotate rotation members 180—as shown in FIG. 40. Nut 402 is advanced further until each of the two spinous process that border the target interspinous space are captured between the rotated ("Open") rotation member 180 and the distal end 3021 of member 302 (see FIG. 41).

Figures 44A, 44B:
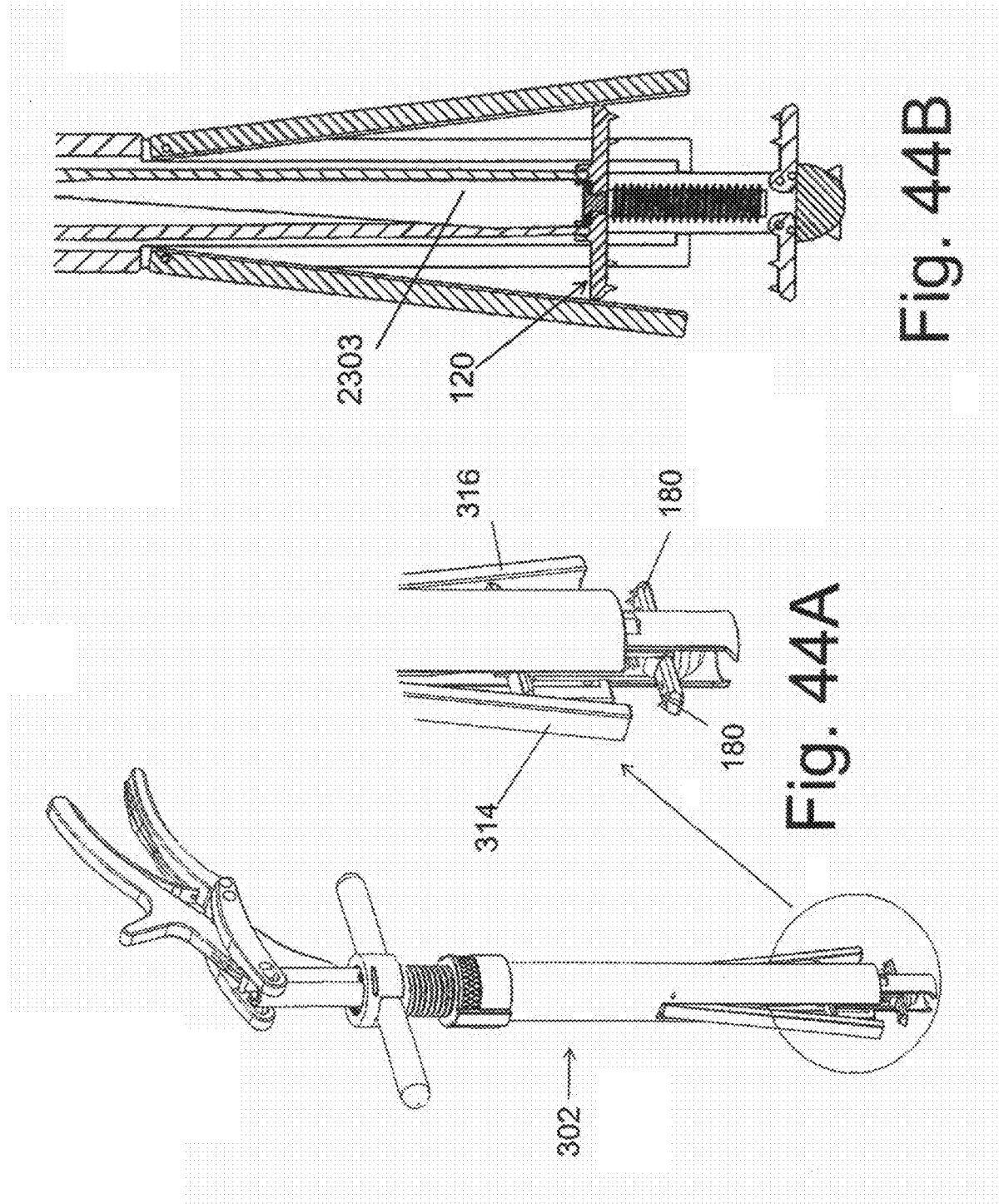
FIG. 44A is a perspective and close-up view of the actuation of the exemplary instrument of FIG. 18 to rotate the plate assembly of FIG. 14 attached thereto to be substantially parallel to the rotational members of the exemplary implant of FIG. 1.
FIG. 44B is a cross-sectional view of the actuation of the exemplary instrument of FIG. 18 to rotate the plate assembly of FIG. 14 attached thereto to be substantially parallel to the rotational members of the exemplary implant of FIG. 1.

Instrument 230 with attached plate 120 (in the "closed" position) is advanced into internal bore 352 of member 350. This is illustrated on FIGS. 42 and 43A. FIG. 43B shows a cross-sectional view with the instrument 230/plate 120 in place. Instrument 230 is actuated in order to rotate plate 120 and position it substantially parallel to the "open" rotation members 180. This is shown in FIG. 44A and in a cross-sectional view in FIG. 44B. Note that channel 2303 provides an open corridor for the placement of locking nut 210 therethrough. FIG. 45 illustrates locking nut 210 being attached to screw-driver 425 and then advanced into channel 2303 of instrument 230 through opening 2305. As locking member 210 engages threads 1506 on member 150, it is rotationally advanced relative to member 150 and it pushes the rotated plate 120 into the ipsilateral side of the captured spinous processes. Note that advancing plate 120 within central bore 1504 of member 150 also compacts the bone graft material contained therein and forces said graft material out of the open sides of central bore 1504 and into certain contact with the decorticated spinous process segments that border the implantation site. This is an important feature of the present disclosure and it functions to guarantee contact of the bone graft material with the adjacent spinous processes. Further, the compressive load placed on the bone graft material will improve the likelihood of bone fusion, since compressive load is a known stimulant of bone formation.

Figure 47:
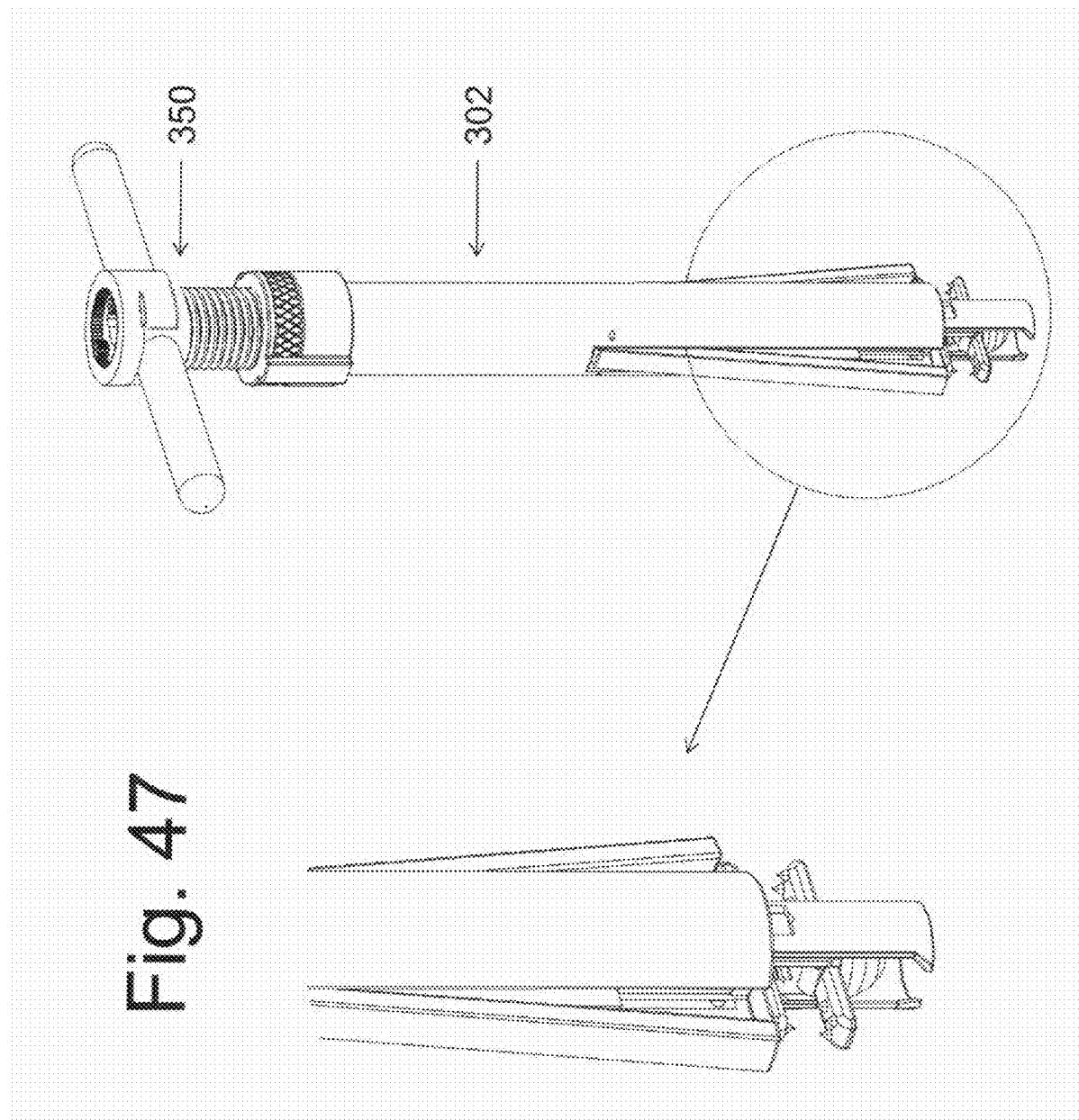
FIG. 47 illustrates a perspective and close-up view of the assembled implant within the exemplary instrument of FIG. 32 having the screw driver of FIG. 45 and the exemplary instrument of FIG. 18 removed.

Continued advancement of locking nut 210 forcibly drives the projections 1804 of member 180 and the projections 1204 of plate 120 into opposing sides of the captured spinous processes. FIG. 47 shows the implant with plate 120 having been advanced and screw driver 425 having been removed.

Figure 48:
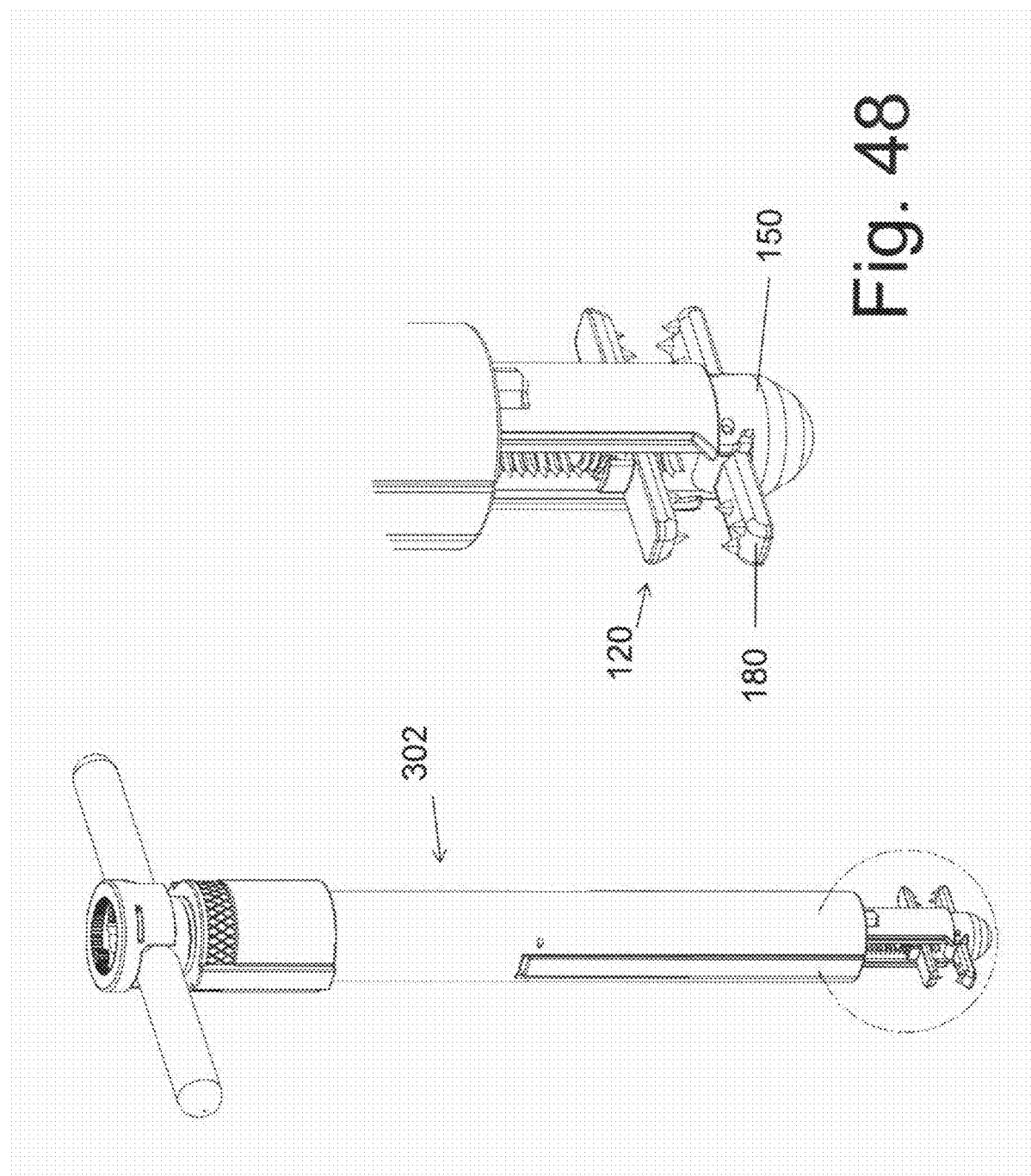
FIG. 48 illustrates a perspective and close-up view of the rotation of the exemplary instrument of FIG. 32 for removal thereof after implantation of the exemplary assembled implant of FIG. 1 at the target interspinous space.

In order to remove the tube assembly of member 302 and member 350, knurled nut 402 is rotated back fully relative to threads 358 (FIG. 48). Member 390 is then rotated into the "open" position so that protrusion 374 of each member 370 extends outward and away from internal bore 352 of member 350. In this way, protrusions 374 disengage from member 150. (Note that member 390 cannot be rotated into the "open" position until knurled nut 402 is rotated back fully relative to threads 358.)

Figure 49:
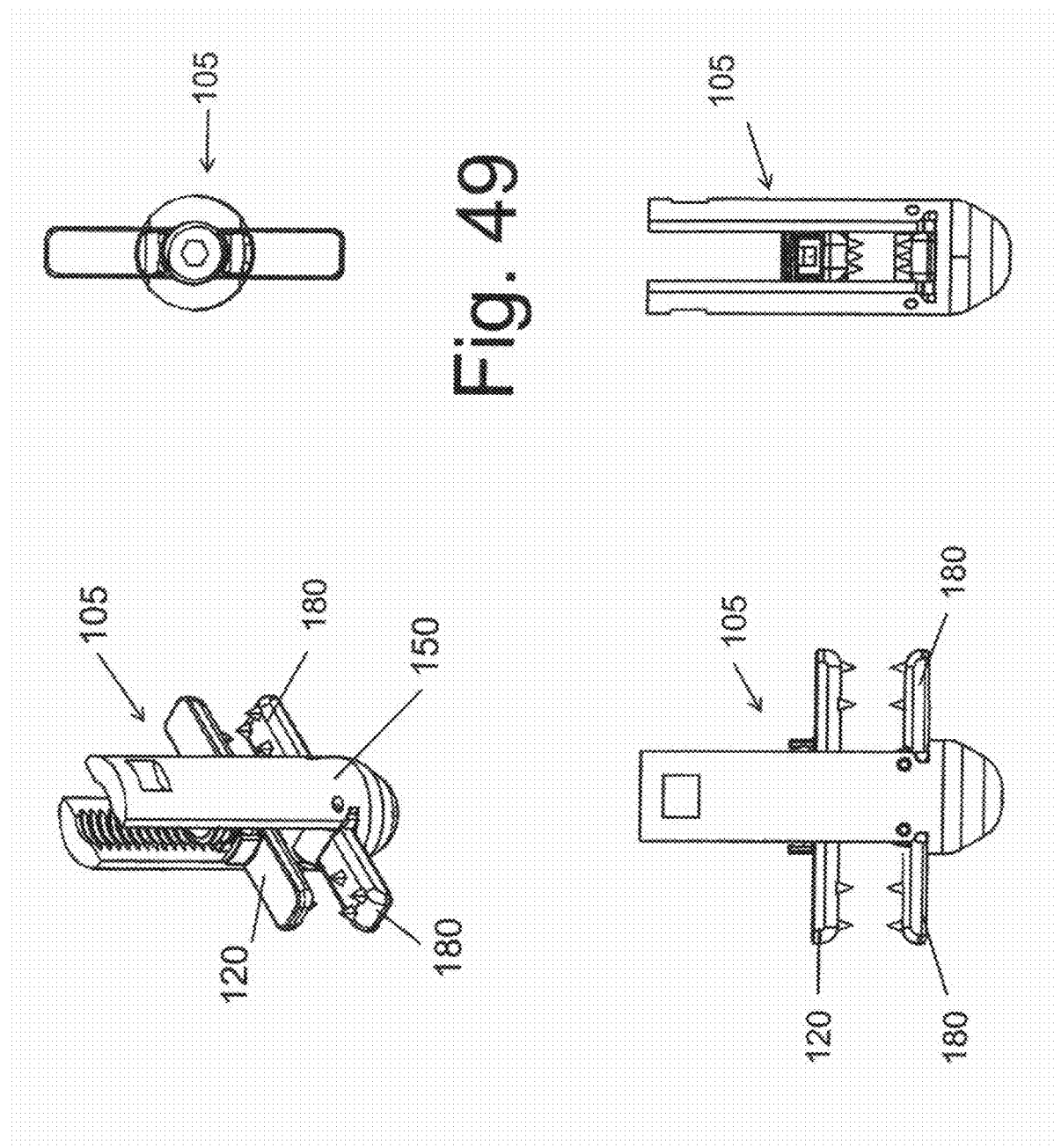
FIG. 49 illustrates top, side, and perspective views of the exemplary assembled implant of FIG. 1.

After removal of the tube assembly, the cylindrical tube used to form and maintain corridor Z is removed. Implant 105 (FIG. 49) is left at the target interspinous space.

Note that the implanted device 105 has a number of novel properties. The implant contains an internal cavity that is sized and configured to house a bone graft material and the enclosed material is able to contact the decorticated surfaces of both spinous processes that border the implanted interspinous space. That is, the spinous processes can fuse together and form a continuous bony bridge that extends from one side surface of the implant through the internal aspect of implant 105 and onto an opposing side surface of the implant. As noted, the internal cavity may in one embodiment be at least 20% of volume of the implant 105. Advancement of member 120 functions as a plunger that compacts the enclosed bone graft material and pushes it of the device and onto the prepared bony surface of the adjacent spinous processes. However, it should be noted that the device may be alternatively (or additionally) coated/made with osteo-conductive (such as demineralized bone matrix, hydroxyapatite, nanotube surface (such as Titanium Oxide) and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. In this way, a mineralized (bony) bond is made between the each of the two device-abutting spinous processes and the implant instead of (or in addition to) a direct mineralized bony fusion between the spinous processes.

An additional novel feature of the implant is use of the Belleville washers (or any appropriate spring/malleable member) to re-load the implant/bone interface in event of fixation member loosening. Finally, the implant accommodates individual variations in bone anatomy by permitting plate 120 to rest in a non-parallel trajectory relative to members 180. This is accomplished by the interaction of the curvilinear surface 2106 of member 210 (FIG. 11) and the curvilinear surface 1952 of retainer 195.

Figure 50:
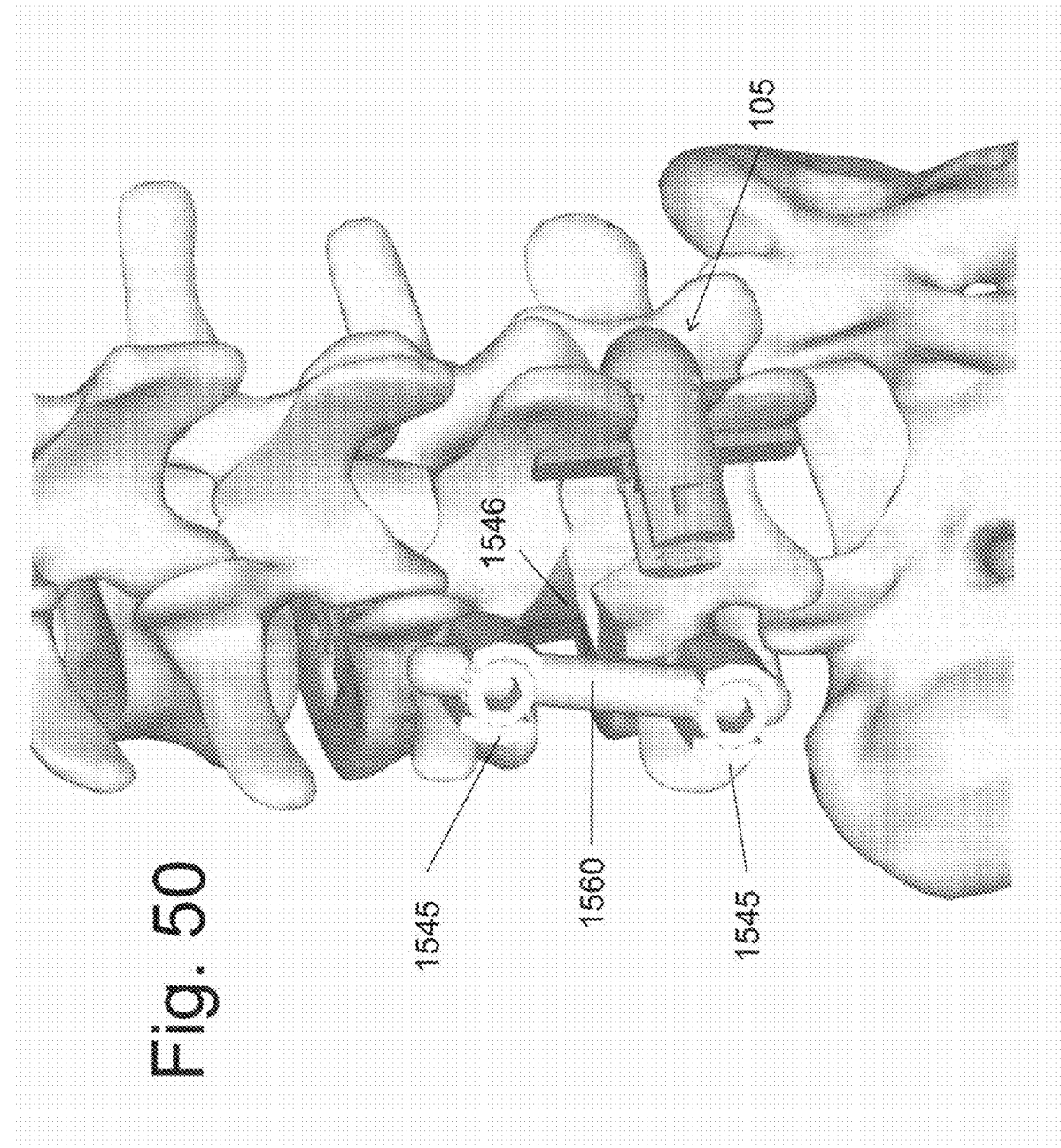
FIG. 50 is a perspective view of an exemplary implant using TLIF methods.

Another method of device use is shown in FIG. 50. In this embodiment, a portion of the facet joint is removed and a bone fusion implant is placed into the anterior column through the cavity created by the facet resection. This operation is known to those of ordinary skill in the art as a Trans-foraminal Lumbar Interbody Fusion (TLIF). A bone screw 1545 can be placed into the pedicle portion of bone at each of the upper (L4 level) and lower (L5 level) vertebral bones. A rod 1560 can be used to rigidly interconnect the screws 1545. The screws/rod can be placed on one side of the vertebral midline and a fixation device 105 can be used to supplement the uni-lateral screw/rod fixation. In one method of use, the implant 105 is implanted though the same (single) skin incision used to implant the screws 1545 and inter-connecting rod 1560.

FIG. 7A shows a schematic illustration of the approximate location of incision site "X" for the TLIF procedure. A soft tissue corridor "J, which extends from incision "X" to the underlying bone, is shown in FIG. 7B. In a first embodiment, all implants are placed ipsilateral to the skin incision "X", wherein an implant 1546 is positioned into the disc space of the anterior column, two screws 1545 and an interconnecting rod 1560, as well as interspinous implant 105 are collectively delivered though corridor "J". A separate contralateral skin incision is not needed, since placement of device 105 obviates the need to place bone screws on the contralateral side of the spinous process. However, it is further contemplated that a separate shin incision can be made on the contralateral side of the spinous processes and bone screws (or other orthopedic implants) may be placed into the vertebral bones on the contralateral side of the spinous process—if the surgeon so desires.

FIGS. 51-55 disclose an alternative embodiment to plate 120. Instead of the unitary plate 120 disclosed above, member 530 is comprised of multiple segments that include two rotatable door member 535 and interconnecting housing 538. Door members 535 are connected to housing 538 via pins 536. Housing 538 contains an internal cut out 5382 that is sized and configured to at least partially contain locking nut 545. Locking nut 545 has external threads that cooperatively engage complimentary threads 1506 of member 150. While cut out 5382 is shown containing locking nut 545 alone, it is contemplated that Belleville washers, spring member or any other appropriate malleable member may be additionally placed within cut out 5382—as was disclosed for plate 120. When Belleville washers are included, they are positioned to abut surface 53822 of cut out 5382 and to rest between locking nut 545 and said surface 5382. In this way, the Belleville washers would excerpt a force that retightens the device-bone interface between door member 535 (and spikes 5352) and the adjacent bone in the event of loosening. This feature was fully discussed for plate 120.

Figure 51:
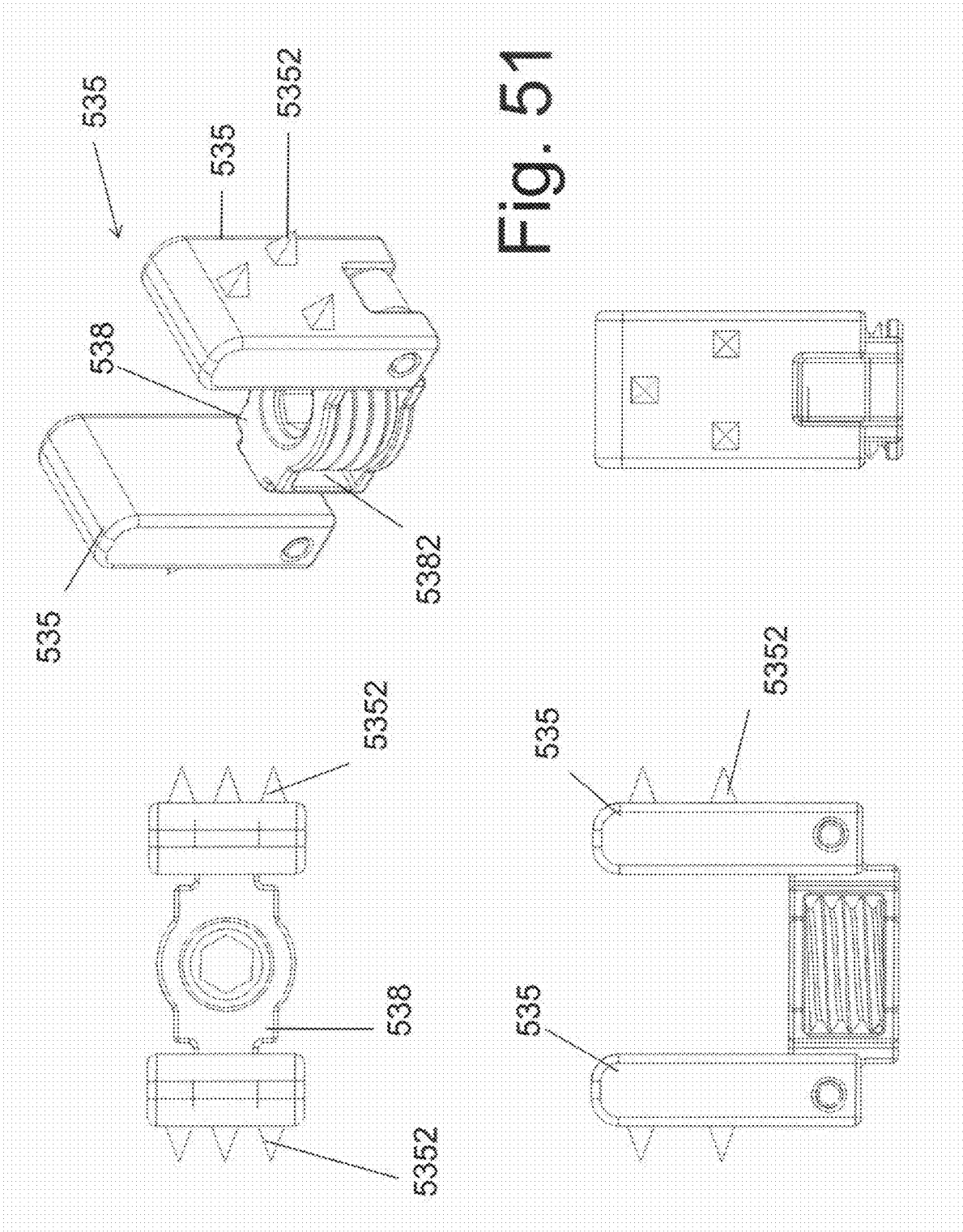
FIG. 51 illustrates side, top, and perspective views of an alternative plate member for use with the fixation device of FIG. 1 in a "closed" position.
Figure 52:
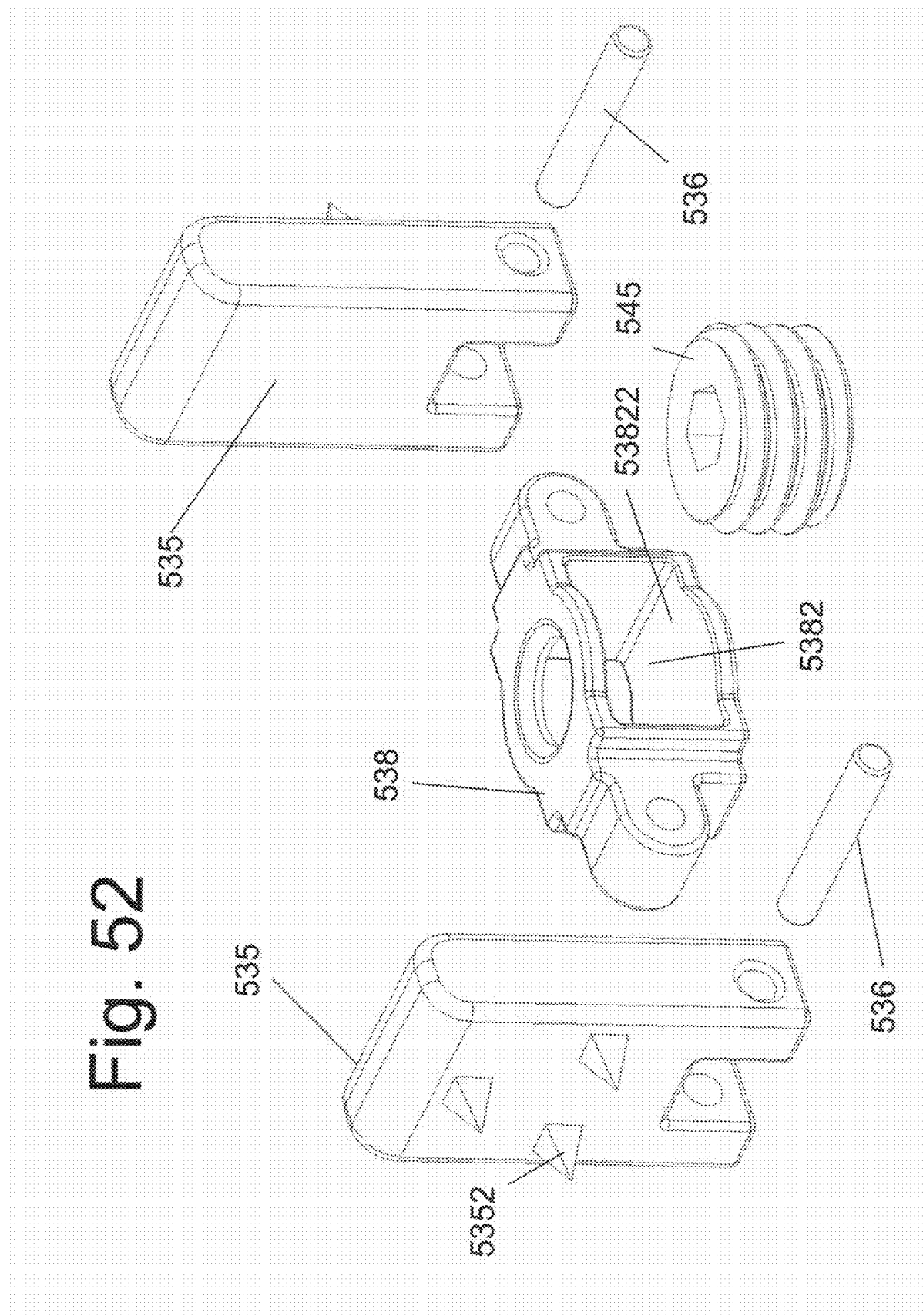
FIG. 52 illustrates an exploded view of the alternative plate member of FIG. 51.

FIG. 51 illustrates member 530 with door members 535 in the "closed" position, whereas FIG. 52 shows an exploded view. FIG. 53 shows member 530 with door member 535 in the "open" position.

Member 105 is advanced through the insertion corridor to the target interspinous space with member 530 attached to member 150—and with door members 535 in the "closed" position. This configuration is shown in FIG. 54 (the deployment tubes are not shown). Note that corner 5354 of door 535 overlaps end surface 1501 of member. It is this corner interaction and interference that produces door rotation into the "open" position.

After the device is positioned at the target interspinous space, locking nut 545 is rotationally advanced relative to threads 1506 of member 150. Doors 535 are forcible rotated by surface 150 so that member 530 is in the "open" position—as shown in FIG. 55. Note that side surfaces 1503 of member 150 retain member 530 in the "open" position. Close-up views of the "closed" to "open" door transition are shown in FIG. 56.

The disclosed devices or any of their components can be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like. Any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An implant adapted for spinal fusion, the implant comprising:
    an elongated housing that extends from a proximal end to a distal end along the direction of a longitudinal axis, and comprises an external perimeter surface, an internal bore and at least one side aperture that extend from said internal bore to the external perimeter, the internal bore being open onto at least a portion of the proximal end of the elongated housing;
    at least one distal bone abutment member configured for movable coupling to a distal segment of the elongated housing;
    at least one proximal bone abutment member configured for movable coupling to a proximal segment of the elongated housing, and comprising a first portion seated within the internal bore and at least a second portion that extends through the at least one side aperture;
    a first mechanism configured to advance the at least one proximal bone abutment member towards the at least one distal bone abutment member without producing concurrent movement of said at least one distal bone abutment member relative to the elongated housing; and
    a second mechanism configured to move said at least one distal bone abutment member relative to the elongated housing.

2. The implant of claim 1, wherein said internal bore of the elongated housing is devoid of the totality of the second mechanism.

3. The implant of claim 1, further comprising a non-implantable instrument having a distal segment configured to couple to said at least one distal bone abutment member, and to produce rotation thereof relative to said elongated housing member.

4. The implant of claim 3, wherein the coupling of said non-implantable instrument with the at least one distal bone abutment member is positioned external to said external perimeter surface of the elongated housing.

5. The implant of claim 1, wherein said first mechanism that advances the at least one proximal bone abutment member is configured to:
    i) upon a first actuation thereof, cause rotation of a longitudinal axis of the at least one proximal bone abutment member away from a parallel orientation with respect to said longitudinal axis of the elongated housing; and
    ii) upon a subsequent actuation thereof, cause translation of the at least one proximal bone abutment member toward the distal end of the elongated housing without further rotation thereof.

6. The implant of claim 1, wherein the at least one side aperture comprises two diametrically opposed side apertures.

7. The implant of claim 6, wherein the at least one distal bone abutment member comprises a first distal bone abutment member communicating at least in part with a first of the two diametrically opposed side apertures, and a second distal bone abutment member communicating at least in part with a second of the two diametrically opposed side apertures.

8. The implant of claim 6, wherein the at least one proximal bone abutment member comprises two extension arms.

9. The implant of claim 8, wherein each of said two extension arms extends through a respective one of the two diametrically opposed side apertures.

10. A kit to deploy an orthopedic implant within a spinal segment, comprising:
an orthopedic implant comprising:
an elongated housing that extends from a proximal end to a distal end along the direction of a longitudinal axis, and comprises an external perimeter surface, an internal bore, and at least one side aperture that extend from the internal bore to the external perimeter, the opening of the internal bore extending onto the proximal end of the elongated housing;
at least one distal bone abutment member configured for movable coupling to a distal segment of the elongated housing;
at least one proximal bone abutment member configured for movable coupling to a proximal segment of the elongated housing; and
a mechanism configured to advance the at least one proximal bone abutment member towards the at least one distal end of the elongated housing; and
a non-implantable instrument having a distal segment configured to (i) couple to said at least one distal bone abutment member, and (ii) produce rotation thereof relative to said elongated housing, said coupling being positioned external to said external perimeter surface of the elongated housing.

11. The kit of claim 10, wherein said mechanism is configured to advance the at least one proximal bone abutment member towards the distal end of the elongated housing without producing concurrent movement of said at least one distal bone abutment member relative to the elongated housing.

12. The kit of claim 10, wherein said rotation of the at least one distal bone abutment member by the non-implantable instrument is independent of movement of the at least one proximal bone abutment member relative to the elongated housing.

13. The kit of claim 10, wherein said internal bore is devoid of a mechanism capable of moving said at least one distal bone abutment member relative to the elongated housing.

14. The kit of claim 10, wherein said mechanism to advance the at least one proximal bone abutment member relative to the elongated housing is configured to:
i) upon a first actuation thereof, cause rotation of said longitudinal axis of the at least one proximal bone abutment member away from a parallel orientation with respect to said longitudinal axis of the elongated housing member, and
ii) upon a subsequent actuation thereof, cause translation of the at least one proximal bone abutment member toward the distal end of the elongated housing.

15. The kit of claim 10, wherein the at least one side aperture comprises two diametrically opposed side apertures.

16. The kit of claim 15, wherein the at least one distal bone abutment member comprises a first distal bone abutment member communicating at least in part with a first of the two diametrically opposed side apertures, and a second distal bone abutment member communicating at least in part with a second of the two diametrically opposed side apertures.

17. The kit of claim 15, wherein the at least one proximal bone abutment member comprises two extension arms.

18. The kit of claim 17, wherein each of said two extension arms extends through a respective one of the two diametrically opposed side apertures.

19. An implant for placement within a skeletal segment, comprising:
a housing member that extends from a proximal end to a distal end along the direction of a longitudinal axis, and comprises an external perimeter surface, an internal bore, and at least one side aperture that extends from the internal bore to the external perimeter;
at least one distal bone abutment member that is movably coupled to a distal segment of the housing member, the internal bore being devoid of a first mechanism needed to move said at least one distal bone abutment member relative to the housing member; and
at least one proximal bone abutment member that is movably coupled to a proximal segment of the housing member; and
a second mechanism that, upon actuation, causes advancement of the at least one proximal bone abutment member towards the distal end of the housing member;
wherein the implant is configured such that movement of the at least one distal bone abutment member relative to the housing member is independent of movement of the at least one proximal bone abutment member; and
wherein the implant is further configured to couple to a non-implantable instrument having a distal segment, the distal segment configured to couple to said at least one distal bone abutment member of the implant and to produce rotation thereof relative to said housing member.

20. The implant of claim 19, wherein the implant is configured such that coupling of said non-implantable instrument to the at least one distal bone abutment member occurs external to said an external perimeter surface of the housing member.

21. The implant of claim 20, wherein said second mechanism is further configured to:
i) upon a first actuation thereof, cause rotation of said longitudinal axis of the at least one proximal bone abutment member away from a parallel orientation with respect to said longitudinal axis of the elongated housing; and
ii) upon a subsequent actuation thereof, cause translation of the at least one proximal bone abutment member toward the distal end of the elongated housing.

22. The implant of claim 19, wherein the at least one side aperture comprises two diametrically opposed side apertures.

23. The implant of claim 22, wherein the at least one distal bone abutment member comprises a first distal bone abutment member communicating at least in part with a first of the two diametrically opposed side apertures, and a second distal bone abutment member communicating at least in part with a second of the two diametrically opposed side apertures.

24. The implant of claim 19, wherein the at least one proximal bone abutment member comprises two extension arms that are joined by a central member.

25. The implant of claim 24, wherein each of said two extension arms extends through a respective one of the two diametrically opposed side apertures.

26. The implant of claim 25, wherein the central member is positioned within said internal bore of the housing member.

27. The implant of claim 26, wherein the implant is further configured such that advancement of the at least one proximal bone abutment member towards the distal end of the housing member advances the central member within said internal bore, and places a compressive load on a bone forming material placed therein.

28. An orthopedic implant configured for placement within a skeletal segment, comprising:
 a housing member that extends from a proximal end to a distal end along the direction of a first longitudinal axis, and comprises an external perimeter surface, an internal bore, and at least one side aperture that extends from the internal bore to the external perimeter;
 at least one distal bone abutment member that is movably coupled to a distal segment of the housing member;
 at least one proximal bone abutment member that extends from a proximal end to a distal end along the direction of a second longitudinal axis, said at least one proximal bone abutment member movably coupled to a proximal segment of the housing member; and
 a first mechanism configured to:
  i) upon a first actuation thereof, cause a rotation of said second longitudinal axis of the at least one proximal bone abutment member away from a parallel orientation with respect to said first longitudinal axis of the housing member, and
  ii) upon a subsequent actuation thereof, cause translation of the at least one proximal bone abutment member toward the distal end of the housing member without an increase in said rotation of the at least one proximal bone abutment member.

29. The implant of claim 28, wherein said implant is configured to utilize a second mechanism to move said at least one distal bone abutment member relative to the housing member.

30. The implant of claim 29, wherein the internal bore is devoid of at least a portion of the second mechanism.

31. The implant of claim 29, wherein the second mechanism comprises a non-implantable instrument configured to couple to said at least one distal bone abutment member and to produce a rotation of a longitudinal axis of the at least one distal bone abutment member away from a parallel orientation with respect to said first longitudinal axis of the housing member.

32. The implant of claim 28, wherein the at least one side aperture comprises two opposing side apertures of the housing member; and
 the at least one proximal bone abutment member comprises two extension arms that are joined by a central member, each of said two extension arms configured to extend through a respective one of the two opposing side apertures of the housing member.

33. An implant adapted for spinal fusion, the implant comprising:
 an elongated housing that extends from a proximal end to a distal end along the direction of a longitudinal axis, and comprises an external perimeter surface, an internal bore and at least one side aperture that extend from said internal bore to the external perimeter, the internal bore being open onto at least a portion of the proximal end of the elongated housing;
 a distal bone abutment member configured for movable coupling to a distal segment of the elongated housing;
 a proximal bone abutment member configured for movable coupling to a proximal segment of the elongated housing, and comprising a first portion seated within the internal bore and at least a second portion that extends through the at least one side aperture;
 a mechanism configured to advance at least the proximal bone abutment member towards the distal bone abutment member without producing concurrent movement of said distal bone abutment member relative to the elongated housing; and
 a non-implantable instrument having a distal segment configured to couple to said distal bone abutment member, and to produce rotation thereof relative to said elongated housing member.

34. An implant adapted for spinal fusion, the implant comprising:
 an elongated housing that extends from a proximal end to a distal end along the direction of a longitudinal axis, and comprises an external perimeter surface, an internal bore and at least one side aperture that extend from said internal bore to the external perimeter, the internal bore being open onto at least a portion of the proximal end of the elongated housing;
 a distal bone abutment member configured for movable coupling to a distal segment of the elongated housing;
 a proximal bone abutment member configured for movable coupling to a proximal segment of the elongated housing, and comprising a first portion seated within the internal bore and at least a second portion that extends through the at least one side aperture; and
 a mechanism configured to advance the proximal bone abutment member towards the distal bone abutment member without producing concurrent movement of said distal bone abutment member relative to the elongated housing;
 wherein said mechanism that advances the proximal bone abutment member is configured to:
  i) upon a first actuation thereof, cause rotation of a longitudinal axis of the proximal bone abutment member away from a parallel orientation with respect to said longitudinal axis of the elongated housing; and
  ii) upon a subsequent actuation thereof, cause translation of the proximal bone abutment member toward the distal end of the elongated housing without further rotation thereof.

\* \* \* \* \*